US008247653B2

(12) United States Patent
Das et al.

(10) Patent No.: US 8,247,653 B2
(45) Date of Patent: Aug. 21, 2012

(54) DELTA-8 DESATURASE GENES, ENZYMES ENCODED THEREBY AND USES THEREOF

(75) Inventors: Tapas Das, Singapore (SG); Pradip Mukerji, Singapore (SG); Padmavathy Krishnan, Hilliard, OH (US); Suzette L. Pereira, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 306 days.

(21) Appl. No.: 12/574,160

(22) Filed: Oct. 6, 2009

(65) Prior Publication Data

US 2010/0154080 A1   Jun. 17, 2010

Related U.S. Application Data

(60) Provisional application No. 61/103,107, filed on Oct. 6, 2008.

(51) Int. Cl.
```
A01H 5/00      (2006.01)
C12N 15/82     (2006.01)
C12N 5/10      (2006.01)
C07H 21/04     (2006.01)
```

(52) U.S. Cl. ........ 800/298; 800/281; 435/410; 435/419; 536/23.2

(58) Field of Classification Search .................. None
See application file for complete search history.

(56) References Cited

U.S. PATENT DOCUMENTS

| | | | |
|---|---|---|---|
| 4,582,788 A | 4/1986 | Erlich | |
| 4,666,701 A | 5/1987 | Horrobin et al. | |
| 4,683,194 A | 7/1987 | Saiki et al. | |
| 4,683,202 A | 7/1987 | Mullis | |
| 4,758,592 A | 7/1988 | Horrobin et al. | |
| 4,826,877 A | 5/1989 | Stewart et al. | |
| 4,943,674 A | 7/1990 | Houck et al. | |
| 4,945,050 A | 7/1990 | Sanford et al. | |
| 5,004,863 A | 4/1991 | Umbeck | |
| 5,106,739 A | 4/1992 | Comai et al. | |
| 5,107,065 A | 4/1992 | Shewmaker et al. | |
| 5,116,871 A | 5/1992 | Horrobin et al. | |
| 5,159,135 A | 10/1992 | Umbeck | |
| 5,175,095 A | 12/1992 | Martineau et al. | |
| 5,188,958 A | 2/1993 | Moloney et al. | |
| 5,231,020 A | 7/1993 | Jorgensen et al. | |
| 5,416,011 A | 5/1995 | Hinchee et al. | |
| 5,420,034 A | 5/1995 | Kridl et al. | |
| 5,463,174 A | 10/1995 | Moloney et al. | |
| 5,518,908 A | 5/1996 | Corbin et al. | |
| 5,569,834 A | 10/1996 | Hinchee et al. | |
| 5,589,379 A | 12/1996 | Kridl et al. | |
| 5,631,152 A | 5/1997 | Fry et al. | |
| 5,700,671 A | 12/1997 | Prieto et al. | |
| 5,750,176 A | 5/1998 | Prieto et al. | |
| 5,912,120 A | 6/1999 | Goldstein et al. | |
| 7,678,560 B2 * | 3/2010 | Damude et al. | ......... 435/254.11 |
| 7,695,950 B2 * | 4/2010 | Damude et al. | ......... 435/254.11 |
| 2008/0214667 A1 | 9/2008 | Das et al. | |

FOREIGN PATENT DOCUMENTS

| | | |
|---|---|---|
| EP | 0050424 B1 | 4/1982 |
| EP | 0084796 B1 | 5/1990 |
| EP | 0237362 B2 | 3/1992 |
| EP | 0201184 B1 | 12/1992 |
| EP | 0258017 B1 | 6/1997 |
| WO | 9524494 A1 | 9/1995 |
| WO | 2007127381 A2 | 11/2007 |
| WO | WO2007127381 A | 11/2007 |

OTHER PUBLICATIONS

Broun et al, Science 282: 1315-1317, Nov. 13, 1996.*
van de Loo et al, PNAS, USA 92: 6743-6747, Jul. 1995.*
Doerks et al, TIG 14(6): 248-250, Jun. 1998.*
Brenner, S.E., TIG 15(4): 132-133, Apr. 1999.*
Bork et al, TIG 12(10): 425-427, Oct. 1996.*
Sayanova et al, Phytochem 65: 147-158, 2004.*
Sequence Accession GE153643, Lucas et al, Oct. 2, 2008.*
Wallis, James G et al, "The Delta-8 Desaturase of Euglena gracilis: An Alternate Pathway for Synthesis of 20-Carbon Polyunsaturated Fatty Acids," Biochemistry and Biophysics, vol. 365, No. 2, 1999, pp. 307-316.
Zhou, Xue-Rong et al, "Isolation and Characterization of Genes From the Marine Microalga Pavlova Salina Encoding Three Front-end Desaturases Involved in Docosahexaenoic Acid Biosynthesis," ScienceDirect, Photochemistry 68 (2007), pp. 785-796.
Bell, Michael V et al, "Lipid Composition During Growth of Motile and Coccolith Forms of *Emiliania huxleyi*," Photochemistry, vol. 41, No. 2, 1996, pp. 465-471.
Singh, Surinder P et al, "Metabolic Engineering of New Fatty Acids in Plants," Current Opinion in Plant Biology, 2005, 8, pp. 197-203.
Napier, Johnathan A., "The Production of Unusual Fatty Acids in Transgenic Plants," Annu. Rev. Plant Biol., 2007, 58, pp. 295-319.
Pereira, Suzette L et al, "Recent Advances in the Study of Fatty Acid Desaturases from Animals and Lower Eukaryotes," Prostaglandins, Leukotrienes and Essential Fatty Acids, 68, 2003, pp. 97-106.
Nakamura, Y., Gojobori, T. and Ikemura, T. (2000) Nucl. Acids Res. 28, 292.
Smith & Waterman, Appl. Math. 2:482 (1981).
Needleman & Wunsch, J. Mol. Biol. 48:443-453 (1970).
Pearson & Lipman, Proc. Natl. Acad. Sci. (USA) 85:2444-2448 (1988).
Higgins et al., CABIOS. 5L151-153 (1989).
Altschul et al., Nucleic Acids Research 25:3389-3402 (1997).
Ingelbrecht et al., (1989) Plant Cell 1:671-680.
Mullis et al, Cold Spring Harbor Symp. Quant. Biol. 51:263-273 (1986).
Marcotte et al., Nature 335:454 457 (1988).

(Continued)

*Primary Examiner* — Elizabeth McElwain

(57) ABSTRACT

The present invention is related to isolated polynucleotides encoding a delta-8 desaturase, delta-8 desaturases encoded by the isolated polynucleotides, expression vectors containing the isolated polynucleotides, host cells containing the expression vectors and methods for producing delta-8 desaturases and polyunsaturated fatty acids.

21 Claims, 13 Drawing Sheets

OTHER PUBLICATIONS

Vasil et al., Bio/Technology 10:667-674 (1992).
Wang et al., Bio/Technology 10:691-696 (1992).
Bower and Birch, Plant J. 2:409-416 (1992).
De la Pena et al., Nature 325:274-276 (1987).
Okamuro and Goldberg, (1989) Biochemistry of Plants 15:1-82.
Jones et al., (1985) EMBO J. 4:2411-2418.
De Almeida et al., (1989) Mol. Gen. Genetics 218:78-86.
Klein et al., (1987) Nature (London) 327:70-73.
Ishida Y. et al., (1996) Nature Biotech. 14:745-750.
Turner, R. and Foster, G. D. (1995) Molecular Biotechnology 3:225-236.
Napier JA et al. (2003) Prostaglandins Leukot Essent Fatty Acids. 68:135-43.
Sayanova O et al (1999) Plant Physiol. 121:641-646.
Guillou H. et al (2004) J Lipid Res. 45: 32-40.
Schnieke et al., Science 278:2130-2133 (1997).
Sayanova O et al. (2000) Biochem Soc Trans. 28:636-638.
McCabe et. al., Bio/Technology 6:923-926 (1988).
Christou et al., Plant Physiol. 87:671-674 (1988).
Cheng et al., Plant Cell Rep. 15:653-657 (1996).
McKently et al., Plant Cell Rep. 14:699-703 (1995).
Grant et al., Plant Cell Rep. 15:254-258, (1995).
Bytebier et al., Proc. Natl. Acad. Sci. (USA) 84:5345-5349, (1987).
Wan and Lemaux, Plant Physiol 104:37-48 (1994).
Rhodes et al., Science 240:204-207 (1988).
Gordon-Kamm et al., Plant Cell 2:603-618 (1990).
Fromm et al., Bio/Technology 8:833-839 (1990).
Koziel et al., Bio/Technology 11: 194-200, (1993).
Armstrong et al., Crop Science 35:550-557 (1995).
Somers et al., Bio/Technology 10:1589-1594 (1992).
Horn et al., Plant Cell Rep. 7:469-472 (1988).
Toriyama et al., Theor Appl. Genet. 73:16-19 (1986).
Park et al., Plant Mol. Biol. 32:1135 1148, (1996).
Abedinia et al., Aust. J. Plant Physiol. 24:133-141 (1997).
Zhang and Wu, Theor. Appl. Genet. 76:835-840 (1988).
Zhang et al. Plant Cell Rep. 7:379-384, (1988).
Battraw and Hall, Plant Sci. 86:191-202 (1992).
Christou et al., Bio/Technology 9:957-962 (1991).
Nielsen, N.C. et al. (1989) Characterization of the glycinin gene family in soybean. Plant Cell, 1, 313-328.
Clough, S.J. and Bent, A.F. (1998) Floral dip: a simplified method for Agrobacterium-mediated transformation of *Arabidopsis thaliana*. Plant J, 16, 735-743.
Cahoon, E.B. et al (2006) Conjugated fatty acids accumulate to high levels in phospholipids of metabolically engineered soybean and *Arabidopsis* seeds. Phytochemistry, 67, 1166-1176.
Pidkowich, M.S. et al (2007) Modulating seed beta-ketoacyl-acyl carrier protein synthase II level converts the composition of a temperate seed oil to that of a palm-like tropical oil. Proc Natl Acad Sci U S A, 104, 4742-4747.
Cahoon, E.B. and Shanklin, J. (2000) Substrate-dependent mutant complementation to select fatty acid desaturase variants for metabolic engineering of plant seed oils. Proc Natl Acad Sci U S A, 97, 12350-12355.
International Preliminary Report on Patentability for PCT/US2009/59689, dated Apr. 12, 2011.
Zhou et al., "Isolation and characterization of genes from marine microalga *Pavlova salina* encoding three front-end desaturases involved in docosahexaenoic acid biosynthesis," Phytochemistry 68(6): 785-96 (Feb. 8, 2007).
Database geneseq [Online] Jan. 24, 2008, "*Pavlova lutheri* delta-8 desaturase DNA SEQ ID No. 15." XP002566733 retrieved from EBI accession No. GSN: AOB 47292.
Bell, Michael V., and Pond, D., "Lipid composition during growth of motile and coccolith forms of *Emiliania huxleyi*," Phytochemistry 41(2): 465-471 (Feb. 1996).
Singh, S.P., et al., "Metabolic engineering of new fatty acids in plants," Curr. Opin. Plant Biol 8(2): 197-203 (Apr. 2005).
Napier, J.A., "The production of unusual fatty acids in transgenic plants," Ann. Rev. Plant Biol. 58: 295-319 (Jun. 2007).
Examination Report issued for Pakistani Patent Application No. Sep. 8, 2009.
McCarty et al., Plant Cell 1:523-532 (1989).
McCarty et al., Cell 66:895-905 (1991).
Hattori et al., Genes Dev. 6:609-618 (1992).
Goff et al., EMBO J. 9:2517-2522 (1990).
Sayanova O et al. (2001) J Exp Bot. 52:1581-1585.
Horrobin DF et al., (1993) Am. J. Clin. Nutr. vol. 57 (Suppl.) 732S-737S.
Okuley, et al. (1994) The Plant Cell 6: 147-158.
Brenner et al., (1976) Adv. Exp. Med. Biol. vol. 83, p. 85-101.
Examination Report for Pakistani Patent Application No. 908/2009 dated Feb. 13, 2012.
Written Opinion of the International Searching Authority for PCT/US2009/059689, dated Apr. 6, 2011.
Communication pursuant to Rules 161 and 162 EPC for European Application No. 09793321.2, dated Jul. 22, 2011.

* cited by examiner

FIGURE 2A

```
                                                                                            70
ED3-8        (1)  ------------MGKGGN---------------ANPRELKGGKAEQLTVYLHGKAVDVSKFAKL HPGGAKALRIFN
Pavlova-D8   (1)  ------------MGKGGDGGA----QAVSGTDASLAEVSSVDSKSVHVVLYGKRVDVTKFQKAH PGGSKVFRIFQ
P.salina-D8  (1)  ------------MGRGGDSSGQAHPAAELAVPSDRAEVSNADSKALHIVLYGKRVDTKFQRT HPGGSKVFRIFQ
Euglena-D8   (1)  ---------------------------------MKSKRQALSPLQLMEQTYDVVNFHPGGA EIIENYQ
Perkinsus-D8 (1)  MTTSTTTVQLQEDLSSGDQNAHPSPSRATPSVGDTKEDARVVIKLFGTWDVTAWLNDHPGGS KVLRAFN 71                                                                            140
ED3-8        (50)  NRDATEQFEMY HSPAA HKMMRAMSKSAPEAPRESEVAT-------SVVGTDFAKLTQTLHDV GCFDPHY
Pavlova-D8   (60)  ERDATEQFESY HSPKA KMMEGMLKKSEDAPASVPLPSR-------STMGTEFKEMIERHKRA GLYDPCP
P.salina-D8  (64)  DRDATEQFESY HSKRA KMMEGMLKKSEDAPADTPLPSQ-------SPMGKDFKAMIERHVAA GYYDPCP
Euglena-D8   (36)  GRDATDAFMVMH FQEAFDKLKRMPKINPSFELPPQAAV-------NEAQEDFRKLREELIAT GMFDASP
Perkinsus-D8 (71)  KKDAT DAVMAM H TDEA KRIIRFSNVVSSAPINASIGDVQVIEKSLSREQLMYYKLRTLARNQG WFQSNL 141                                                                           210
ED3-8        (112) PDEAFKL GLTLLPGFL GFYLLRSGMPALG--SFLIAFSYYMSGWT SHDYL LHGCLKGGQKQLVHWN NAVG
Pavlova-D8   (123) LDELFKL TIVLAPIFV GAYLVRSGVSPLAG-ALSMGFGFYLDGW LAHDYL LHAVFKGSVNTLVKAN NAMG
P.salina-D8  (127) LDELFKL SLVLLPTFAG MYMLKAGVGSPLCGALMVSFGWYLDGW LAHDYL LHHSVFKGSVARTVGWN NAAG
Euglena-D8   (98)  LWYSYKI STTLGLGVL GYFLMVQYQMYFIG-AVLLGMHYQQMGWL SHDIC HHQTFKNR------NWNN LVG
Perkinsus-D8 (141) LYEGV KAMIAFGLLLIG FATLYFDYGIWS--TALIGFAWFQLG WL GHD WSHH TALPKSTTNCAN YDYLG 211                                                                           280
ED3-8        (180) YAIG AWQG YAVGWWRARHNT THHL VTNEEGNDPDIMTAPV FVRNNPVIAAALN-AAQRWQQY YYVPAM
Pavlova-D8   (192) YALG FLQGY DVAAWWRARHNT THHV CTNEDGSDPDIKTAPL YVRENPSIAKRLN-FFQRWQQY YYVPTM
P.salina-D8  (197) YFLG FVQGY AVEWWRARHNT THHV CTNEDGSDPDIKTAPL YVRNKPSIAKRLN-AFQRYQQY YYVPVM
Euglena-D8   (162) LVFG NGLQGF SVTCWKDRHNA HSATN VQGHDPDIDNLPP AWSEDDVTRASPISRKLIQFQQY FLVIC
Perkinsus-D8 (209) WLTG LARG NTLLWVWKLRHN THHV LTNQYENDPDL TQPP HFFEFDFD-VG------NVNRYQAVY YLPML

```
                281
ED3-8      (248) SLMDMYWRFESMQYLAARP---------------------FNKVWASWALLALHYSFVGYMFHGQYQWLLLTMLVRG
Pavlova-D8 (260) AILDLYWRLESIAYVAVR-----------------------LPKMWMQAAALAAHYALLCWVFAAHLNLIPLMMVARG
P.salina-D8 (265) AILDLYWRLESIAYVAMR-----------------------LPKMLPQALALVAHYAIVAWFAGNYHLLPLVTVLRG
Euglena-D8 (232) ILLRFIWCFQCVLTVRSLKDRDNQFYRSQYKKEAIGLALHWTLKALFHLFFMPSILTSLLVFFVSELVGG
Perkinsus-D8 (272) TLLHLFWLYESVLVCLRQSKSINR-------YNRMHARRDTVALVLHILIVGIISYTSGKYLILLAYMLSG
                                                                                        350
                351                                                                     420
ED3-8      (304) FLTGIVVFSTHYGEEVIPGDH----GMTLVEQTAHTSRNITGGYLVNL-------LTGYISLQTEHHLWPMM
Pavlova-D8 (315) FATGIVFATHYGEDILDREHVEGMTLVEQTMTLVEQTAKTSRNITGGWLVNV----LTGFISLQTEHHLFPMM
P.salina-D8 (320) FGTGITVFATHYGEDILDADQVRHMTLVEQTALTSRNISGGWLVNV---------LTGFISLQTEHHLFPMM
Euglena-D8 (302) FGIAIVFMNHYPLEKIGDPVVWDGHGFSVGQIHETMNIRRGIITDW---------FFGGLNYQIEHHLWPTL
Perkinsus-D8 (337) FLTAVVFASHYNEPRVASGE--SLSLVRQTLLTTINIGSFSDTHWEKKLWFYLIGGLNMQIEHHLFPTM
                421                                475
ED3-8      (365) PTARLEAAQPYARAFFKKHGFVYRESNLVECVKYNIAALDITTRNGEWAEMPH-----
Pavlova-D8 (378) PTGNLMTIQPEVRDFFKKHGLEYREGNLFQCVHQNIKALAFEHLLH-----------
P.salina-D8 (383) PTGNLMTIQPEVRAFFKKHGLEYREGNLIECVRQNIRALAFEHLL------------
Euglena-D8 (365) PRHNLTAVSYQVEQLCQKHNLPYRNPLPHEGLVILLRYLAVFARMAEKQPAGKAL---
Perkinsus-D8 (405) PRHNLPKTTFLVKSLAQELGLPYKETNIVSLTKAAVTLHHNALRNIERLLAR------
```

FIGURE 3A

MKSKRQALSPLQLMEQTYDVVNFHPGGAEIIENYQGRDATDAFMVMHFQEAFDKLKR
MPKINPSFELPPQAAVNEAQEDFRKLREELIATGMFDASPLWYSYKISTTLGLGVLGYFL
MVQYQMYFIGAVLLGMHYQQMGWLSHDICHHQTFKNRNWNNLVGLVFGNGLQGFSV
TCWKDRHNAHHSATNVQGHDPDIDNLPPLAWSEDDVTRASPISRKLIQFQQYYFLVICIL
LRFIWCFQCVLTVRSLKDRDNQFYRSQYKKEAIGLALHWTLKALFHLFFMPSILTSLLVF
FVSELVGGFGIAIVVFMNHYPLEKIGDPVWDGHGFSVGQIHETMNIRRGIITDWFFGGLN
YQIEHHLWPTLPRHNLTAVSYQVEQLCQKHNLPYRNPLPHEGLVILLRYLAVFARMAEK
QPAGKAL*

FIGURE 3B

MGKGGDGGAQAVSGTDASLAEVSSVDSKSVHVVLYGKRVDVTKFQKAHPGGSKVFRI
FQERDATEQFESYHSPKAIKMMEGMLKKSEDAPASVPLPSRSTMGTEFKEMIERHKRAG
LYDPCPLDELFKLTIVLAPIFVGAYLVRSGVSPLAGALSMGFGFYLDGWLAHDYLHHAV
FKGSVNTLVKANNAMGYALGFLQGYDVAWWRARHNTHHVCTNEDGSDPDIKTAPLLI
YVRENPSIAKRLNFFQRWQQYYYVPTMAILDLYWRLESIAYVAVRLPKMWMQAAALA
AHYALLCWVFAAHLNLIPLMMVARGFATGIVVFATHYGEDILDREHVEGMTLVEQTAK
TSRNITGGWLVNVLTGFISLQTEHHLFPMMPTGNLMTIQPEVRDFFKKHGLEYREGNLF
QCVHQNIKALAFEHLLH*

FIGURE 4A

MGRGGDSSGQAHPAAELAVPSDRAEVSNADSKALHIVLYGKRVDVTKFQRTHPGGSK
VFRIFQDRDATEQFESYHSKRAIKMMEGMLKKSEDAPADTPLPSQSPMGKDFKAMIERH
VAAGYYDPCPLDELFKLSLVLLPTFAGMYMLKAGVGSPLCGALMVSFGWYLDGWLAH
DYLHHSVFKGSVARTVGWNNAAGYFLGFVQGYAVEWWRARHNTHHVCTNEDGSDPD
IKTAPLLIYVRNKPSIAKRLNAFQRYQQYYYVPVMAILDLYWRLESIAYVAMRLPKMLP
QALALVAHYAIVAWVFAGNYHLLPLVTVLRGFGTGITVFATHYGEDILDADQVRHMTL
VEQTALTSRNISGGWLVNVLTGFISLQTEHHLFPMMPTGNLMTIQPEVRAFFKKHGLEY
REGNLIECVRQNIRALAFEHLL*

FIGURE 4B

MTTSTTTVQLQEDLSSGDQNAHPSPSRATPSVGDTKEDARVVIKLFGTWVDVTAWLND
HPGGSKVLRAFNKKDATDAVMAMHTDEAIKRIIRFSNVVSSAPINASIGDVQVIEKSLSR
EQLMYYKLRTLARNQGWFQSNLLYEGVKAMIAFGLLIIGFATLYFDYGIWSTALIGFAW
FQLGWLGHDWSHHTALPKSTTNCANYNDYLGWLTGLARGNTLLWWKLRHNTHHVLT
NQYENDPDILTQPPLHFFEDFDVGNVNRYQAVYYLPMLTLLHLFWLYESVLVCLRQSKS
INRYNRMHARRDTVALVLHILIVGIISYTSGKYLLILLAYMLSGFLTAVVVFASHYNEPR
VASGESLSLVRQTLLTTINIGSFSDTHWEKKLWFYLTGGLNMQIEHHLFPTMPRHNLPKT
TFLVKSLAQELGLPYKETNIVSLTKAAVTTLHHNALRNIERLLAR*

FIGURE 4C

MVLTTPALNLKKERTSFTQEISKLWVLHGQVYDFTDFVKYHPAGSRAILLGRGRDCTVL
FESYHTVLPSDALDEKYRVSAPNAKLEESRSAKLFSFEEGSFYRTLKQRTREYFKTNNLS
TKATTMEVIYFVATILSIYFCTWAAFVQGSLIAAVLHGVGRAICIIQPIHATSHYAMFRSV
WLNQWAYRISMAVSGSSPAQWTTKHVINHHVETNLCPTDDDTNYPIKRILHEFPRIFFH
KYQHIYIWLVYPYTTILWHFSNLAKLALGAARGQMYEGIAKVSQETSGDVVETAMTLF
FFTFSRLLLPFLCLPFTTAAAVFLLSEWTCSTWFAIQFAVSHEVDECVEHEKSVLDTIKAN
EAKGIVNQGGLVDWGAHQVRASHNYSADSLLSLHFSGGLNLQIEHHLFPSVHYTHYPA
PSKLVQQTCKEFNLPCTLSPSMMGAVTKHYHQLKKMGAEN*

FIGURE 5

GCCCTTTGGAGGGTGCGCCATAACGCGCACCACGTGGGCAGCAACGAAGAAGGCAA
CGACCCCGACATCATGACCGCGCCTGTGCTCATCTTCGTGCGCAACAGCCCGGTGAT
CGCCGCTGCCCTCAACGCGGCGCAGCGGTGGCAGCAGTACTACTACGTGCCCGCGA
TGAGCCTCATGGACATGTACTGGCGCTTCGAGTCGATGCAGTACCTGGCCGCGCGGC
CCTTCAACAAGGTCTGGGCCTCGTGGGCGCTCCTCGCGCTGCACTACTCCTTTGTCG
GCTACATGTTCCACGGACAGTACCAGTGGCTGCTGCTGACGATGCTGGTGCGCGGCT
TCCTCACGGGCATCGTCGTCTTCTCGACGCATTATGGCGAGGAGGTCATCCCGGGCG
ACCACGGCATGACACTCGTCGAGCAGACGGCGCTCACCTCTCGCAACATCACCGGC
GGGTACCTCGTCAACCTGCTCACGGGCTACATCTCGCTGCAGACCGAGCATCACCTC
TTCCCCATGATGCCCAAGGGC

FIGURE 6

ALWRVRHNAHHVGSNEEGNDPDIMTAPVLIFVRNSPVIAAALNAAQRWQQYYYVPAM
SLMDMYWRFESMQYLAARPFNKVWASWALLALHYSFVGYMFHGQYQWLLLTMLVR
GFLTGIVVFSTHYGEEVIPGDHGMTLVEQTALTSRNITGGYLVNLLTGYISLQTEHHLFP
MMPKG

FIGURE 7A

ATGGGCAAGGGCGGCAACGCGAACCCGCGGGAGCTCAAAGGCGGCAAGGCCGAGC
AGCTGACAGTCTACCTGTATGGCAAGGCTGTCGACGTCTCGAAGTTCGCGAAGCTGC
ACCCGGGAGGCGCCAAGGCGCTGCGCATCTTCAACAACCGTGACGCCACCGAGCAG
TTCGAGATGTACCACTCGCCCGCCGCCCACAAGATGATGCGTGCGATGTCGAAGAG
CGCGCCGGAGGCCCCGAGGGAGAGCGAGGTCGCGACGTCGGTCGTTGGGACGGACT
TCGCCAAGCTGACGCAGACGCTGCACGACGTCGGATGCTTCGACCCTCACTACCCAG
ACGAGGCCTTCAAGCTCGGCCTCACGCTGCTGCCCGGATTCCTCGGCTTCTACCTGC
TGCGGAGCGGCATGCCGGCGCTCGGATCCTTCCTGATCGCTTTCTCGTACTACATGT
CTGGGTGGACCTCCCACGATTACTTGCACCACGGCTGCCTCAAGGGCGGCCAAAAG
CAGCTGGTGCACTGGAACAACGCCGTCGGCTACGCAATCGGCGCTTGGCAGGGCTA
CGCGGTCGNNTGGTGGCGAGCGCGCCACAACACGCACCACCTCGTCACGAACGAAG
AAGGCAACGACCCCGACATCATGACCGCGCCTGTGCTCATCTTCGTGCGCAAC

FIGURE 7B

MGKGGNANPRELKGGKAEQLTVYLYGKAVDVSKFAKLHPGGAKALRIFNNRDATEQF
EMYHSPAAHKMMRAMSKSAPEAPRESEVATSVVGTDFAKLTQTLHDVGCFDPHYPDE
AFKLGLTLLPGFLGFYLLRSGMPALGSFLIAFSYYMSGWTSHDYLHHGCLKGGQKQLV
HWNNAVGYAIGAWQGYAVXWWRARHNTHHLVTNEEGNDPDIMTAPVLIFVRN

FIGURE 8A

GTACCAGTGGCTGCTGCTGACGATGCTGGTGCGCGGCTTCCTCACGGGCATCGTCGT
CTTCTCGACGCATTATGGCGAGGAGGTCATCCCGGGCGACCACGGCATGACACTCGT
CGAGCAGACGGCGCTCACCTCTCGCAACATCACCGGCGGGTACCTCGTCAACCTGCT
CACGGGCTACATCTCGCTGCAGACGGAGCACCACCTCTGGCCGATGATGCCCACCG
CGCGCCTCGAGGCGGCGCAGCCCTACGCGCGCGCCTTCTTCAAGAAGCACGGCTTC
GTCTACCGCGAGTCGAACCTCGTCGAGTGCGTCAAGTACAACATCGCCGCCCTCGAC
ATCACCACGCGCAACGGCGAGTGGGCAGAGATGCCGCACTAGCCGGCGGGCTCCGC
CTCTCCAGGCCGGACGTGACCGCGCCGCGGGCGACAGCGACCGCGCGGGCCGCACG
GGCCACCTGTTGAGGGGAGCGGCGTCGCAACAGGCAGAGAGATAATAATAGAGAG
GCATGTGTGCTGGGACGCTATTGGCTATTTCGGTATATGGACAGGCAGGTAGCGCGC
AAAAAAAAAAAAAAAAAAAAAAAAAA

FIGURE 8B

YQWLLLTMLVRGFLTGIVVFSTHYGEEVIPGDHGMTLVEQTALTSRNITGGYLVNLLTG
YISLQTEHHLWPMMPTARLEAAQPYARAFFKKHGFVYRESNLVECVKYNIAALDITTRN
GEWAEMPH*PAGSASPGRT*PRRGRQRPRGPHGPPVEGSGVATGREIIIERHVCWDAIGY
FGIWTGR*RKKKKKKKKHMPLRSEG

FIGURE 9

```
ATGGGCAAGGGCGGCAACGCGAACCCGCGGGAGCTCAAAGGCGGCAAGGCCGAGC
AGCTGACAGTCTACCTGCATGGCAAGGCTGTCGACGTCTCGAAGTTCGCGAAGCTGC
ACCCGGGAGGCGCCAAGGCGCTGCGCATCTTCAACAACCGTGACGCCACCGAGCAG
TTCGAGATGTACCACTCGCCCGCCGCCCACAAGATGATGCGTGCGATGTCGAAGAG
CGCGCCGGAGGCCCCGAGGGAGAGCGAGGTCGCGACGTCGGTCGTTGGGACGGACT
TCGCCAAGCTGACGCAGACGCTGCACGACGTCGGATGCTTCGACCCTCACTACCCAG
ACGAGGCCTTCAAGCTCGGCCTCACGCTGCTGCCCGGATTCCTCGGCTTCTACCTGC
TGCGGAGCGGCATGCCGGCGCTCGGATCCTTCCTGATCGCTTTCTCGTACTACATGT
CTGGGTGGACCTCCCACGATTACTTGCACCACGGCTGCCTCAAGGGCGGCCAAAAG
CAGCTGGTGCACTGGAACAACGCCGTCGGCTACGCAATCGGCGCTTGGCAGGGCTA
CGCGGTCGGCTGGTGGCGAGCGCGCCACAACACGCACCACCTCGTCACGAACGAAG
AAGGCAACGACCCCGACATCATGACCGCGCCTGTGCTCATCTTCGTGCGCAACAACC
CGGTGATCGCCGCTGCCCTCAACGCGGCGCAGCGGTGGCAGCAGTACTACTACGTG
CCCGCGATGAGCCTCATGGACATGTACTGGCGCTTCGAGTCGATGCAGTACCTGGCC
GCGCGGCCCTTCAACAAGGTCTGGGCCTCGTGGGCGCTCCTCGCGCTGCACTACTCC
TTTGTCGGCTACATGTTCCACGGACAGTACCAGTGGCTGCTGCTGACGATGCTGGTG
CGCGGCTTCCTCACGGGCATCGTCGTCTTCTCGACGCATTATGGCGAGGAGGTCATC
CCGGGCGACCACGGCATGACACTCGTCGAGCAGACGGCGCACACCTCTCGCAACAT
CACCGGCGGGTACCTCGTCAACCTGCTCACGGGCTACATCTCGCTGCAGACGGAGC
ACCACCTCTGGCCGATGATGCCCACCGCGCGCCTCGAGGCGGCGCAGCCCTACGCG
CGCGCCTTCTTCAAGAAGCACGGCTTCGTCTACCGCGAGTCGAACCTCGTCGAGTGC
GTCAAGTACAACATCGCCGCCCTCGACATCACCACGCGCAACGGCGAGTGGGCAGA
GATGCCGCACTAG
```

FIGURE 10

EMYHSPAAHKMMRAMSKSAPEAPRESEVATSVVGTDFAKLTQTLHDVGCFDPHYPDE
AFKLGLTLLPGFLGFYLLRSGMPALGSFLIAFSYYMSGWTSHDYLHHGCLKGGQKQLV
HWNNAVGYAIGAWQGYAVGWWRARHNTHHLVTNEEGNDPDIMTAPVLIFVRNNPVI
AAALNAAQRWQQYYYVPAMSLMDMYWRFESMQYLAARPFNKVWASWALLALHYSF
VGYMFHGQYQWLLLTMLVRGFLTGIVVFSTHYGEEVIPGDHGMTLVEQTAHTSRNITG
GYLVNLLTGYISLQTEHHLWPMMPTARLEAAQPYARAFFKKHGFVYRESNLVECVKYN
IAALDITTRNGEWAEMPH*

FIGURE 11

AAAATGGGTAAAGGTGGTAATGCTAATCCAAGAGAATTGAAAGGTGGTAAAGCTGA
ACAATTGACTGTTTATTTGCATGGTAAAGCTGTTGATGTTTCTAAATTTGCTAAATTG
CATCCAGGTGGTGCTAAAGCATTGAGAATTTTTAATAATAGAGATGCTACTGAACAA
TTTGAAATGTATCATTCTCCAGCTGCTCATAAAATGATGAGAGCTATGTCTAAATCT
GCTCCAGAAGCTCCAAGAGAATCTGAAGTTGCTACTTCTGTTGTTGGTACTGATTTT
GCTAAATTGACTCAAACTTTGCATGATGTTGGTTGTTTTGATCCACATTATCCAGATG
AAGCATTTAAATTGGGTTTGACTTTGTTGCCAGGTTTTTTGGGTTTTTATTTGTTGAG
ATCTGGTATGCCAGCTTTGGGTTCTTTTTTGATTGCTTTTTCTTATTATATGTCTGGTT
GGACTTCTCATGATTATTTGCATCATGGTTGTTTGAAAGGTGGTCAAAAACAATTGG
TTCATTGGAATAATGCTGTTGGTTATGCTATTGGTGCTTGGCAAGGTTATGCTGTTGG
TTGGTGGAGAGCTAGACATAATACTCATCATTTGGTTACTAATGAAGAAGGTAATGA
TCCAGATATTATGACTGCTCCAGTTTTGATTTTTGTTAGAAATAATCCAGTTATTGCT
GCTGCTTTGAATGCTGCTCAAAGATGGCAACAATATTATTATGTTCCAGCTATGTCTT
TGATGGATATGTATTGGAGATTTGAATCTATGCAATATTTGGCTGCTAGACCATTTA
ATAAAGTTTGGGCTTCTTGGGCTTTGTTGGCTTTGCATTATTCTTTTGTTGGTTATATG
TTTCATGGTCAATATCAATGGTTGTTGTTGACTATGTTGGTTAGAGGTTTTTTGACTG
GTATTGTTGTTTTTCTACTCATTATGGTGAAGAAGTTATTCCAGGTGATCATGGTAT
GACTTTGGTTGAACAAACTGCTCATACTTCTAGAAATATTACTGGTGGTTATTTGGTT
AATTTGTTGACTGGTTATATTTCTTTGCAAACTGAACATCATTTGTGGCCAATGATGC
CAACTGCTAGATTGGAAGCTGCTCAACCATATGCTAGAGCTTTTTTTAAAAAACATG
GTTTTGTTTATAGAGAATCTAATTTGGTTGAATGTGTTAAATATAATATTGCTGCTTT
GGATATTACTACTAGAAATGGTGAATGGGCTGAAATGCCACATTAA

FIGURE 12

ATGGCCCTCGCAAACGACGCGGGAGAGCGCATCTGGGCGGCTGTGACCGACC
CGGAAATCCTCATTGGCACCTTCTCGTACTTGCTACTCAAACCGCTGCTCCGCAATTC
CGGGCTGGTGGATGAGAAGAAGGGCGCATACAGGACGTCCATGATCTGGTACAACG
TTCTGCTGGCGCTCTTCTCTGCGCTGAGCTTCTACGTGACGGCGACCGCCCTCGGCTG
GGACTATGGTACGGGCGCGTGGCTGCGCAGGCAAACCGGCGACACACCGCAGCCGC
TCTTCCAGTGCCCGTCCCGGTTTGGGACTCGAAGCTCTTCACATGGACCGCCAAGG
CATTCTATTACTCCAAGTACGTGGAGTACCTCGACACGGCCTGGCTGGTGCTCAAGG
GCAAGAGGGTCTCCTTTCTCCAGGCCTTCCACCACTTTGGCGCGCCGTGGGATGTGT
ACCTCGGCATTCGGCTGCACAACGAGGGCGTATGGATCTTCATGTTTTTCAACTCGT
TCATTCACACCATCATGTACACCTACTACGGCCTCACCGCCGCCGGGTATAAGTTCA
AGGCCAAGCCGCTCATCACCGCGATGCAGATCTGCCAGTTCGTGGGCGGCTTCCTGT
TGGTCTGGGACTACATCAACGTCCCCTGCTTCAACTCGGACAAAGGGAAGTTGTTCA
GCTGGGCTTTCAACTATGCATACGTCGGCTCGGTCTTCTTGCTCTTCTGCCACTTTTT
CTACCAGGACAACTTGGCAACGAAGAAATCGGCCAAGGCGGGCAAGCAGCTCTAG

DELTA-8 DESATURASE GENES, ENZYMES ENCODED THEREBY AND USES THEREOF

RELATED APPLICATION INFORMATION

This application is a nonprovisional application of U.S. Provisional Application Ser. No. 61/103,107, filed Oct. 6, 2008, the entirety of which is hereby incorporated by reference.

FIELD OF THE INVENTION

The present invention is related to isolated polynucleotides encoding a delta-8 desaturase, delta-8 desaturases encoded by the isolated polynucleotides, expression vectors containing the isolated polynucleotides, host cells containing the expression vectors and methods for producing delta-8 desaturases and polyunsaturated fatty acids.

BACKGROUND

Polyunsaturated fatty acids (PUFAs) play many roles in the proper functioning of all life forms. For example, PUFAs are important components of the plasma membrane of a cell, where they are found in the form of phospholipids. PUFAs are necessary for the proper development of the infant brain, as well as for tissue formation and repair in mature mammals.

A number of enzymes, most notably desaturases and elongases, are involved in PUFA biosynthesis (See, FIG. 1). Desaturases catalyze the introduction of unsaturations (e.g., double bonds) between carbon atoms within the fatty acid alkyl chain of the substrate. Elongases catalyze the addition of a 2-carbon unit to a fatty acid substrate. For example, linoleic acid (LA, 18:2n-6) is produced from oleic acid (OA, 18:1n-9) by a Δ12-desaturase. Eicosadienoic acid (EDA, 20:2n-6) is produced from LA by a Δ9-elongase. Dihomo-γ-linolenic acid (DGLA, 20:3n-6) is produced from EDA by a Δ8-desaturase (See, FIG. 1). Arachidonic acid (ARA, 20:4n-6) is produced from DGLA by a Δ5-desaturase (See, FIG. 1).

A number of important long-chain PUFAs are known in the art. For example, one of the most important long-chain PUFAs is eicosapentaenoic acid (EPA). EPA is found in fungi and in marine oils. A second important long-chain PUFA is docosahexaenoic acid (DHA). DHA is most often found in fish oil and can also be purified from mammalian brain tissue. A third important long-chain PUFA is ARA. ARA is found in filamentous fungi and can also be purified from mammalian tissues including the liver and the adrenal glands.

ARA, EPA and/or DHA, can be produced via either the alternate Δ8-desaturase/Δ9-elongase pathway or the conventional Δ6-desaturase pathway (See, FIG. 1). Elongases active on substrate fatty acids in the conventional Δ6 pathway for the production of long-chain PUFAs, particularly ARA, EPA and DHA, have previously been identified. The conventional Δ6-desaturase pathway for converting LA to DGLA and alpha-linolenic acid (ALA) to ω3-eicosatetraenoic acid (ω3-ETA) utilizes the Δ6-desaturase enzyme to convert LA to gamma-linolenic acid (GLA) and ALA to stearidonic acid (SDA); and a C18-elongase enzyme to convert GLA to DGLA and SDA to ω3-ETA. However, in certain instances, the alternate Δ8-desaturase/Δ9-elongase may be preferred over the conventional Δ6-desaturase pathway. For example, if particular residual omega-6 or omega-3 fatty acid intermediates, such as GLA or SDA, are not desired during production of DGLA, ARA, ω3-ETA, EPA, ω3-docosapentaenoic acid (DPA) and/or DHA, the alternate Δ8-desaturase/Δ9-elongase pathway may be used as an alternative to the conventional Δ6-desaturase pathway to bypass GLA and SDA formation. Δ8-desaturases are useful in this pathway because they desaturate a fatty acid between the eighth and ninth carbon atom (numbered from the carboxyl-terminal end of the molecule) and can, for example, catalyze the conversion of ω6-eicosadienoic acid (EDA) to DGLA and/or ω3-eicosatrienoic acid (ω3-ETrA) to ω3-ETA. Therefore, there is a need in the art for new sources of Δ8-desaturases that can be used in the production of long-chain PUFAs.

SUMMARY OF THE INVENTION

In one aspect, the present invention relates to an isolated nucleotide acid or fragment thereof comprising or complementary to a nucleotide sequence encoding a polypeptide having desaturase activity, wherein the amino acid sequence of the polypeptide has at least 55% sequence identity to the amino acid sequence comprising SEQ ID NO:29. The isolated nucleic acid or fragment thereof encodes a functionally active Δ8-desaturase enzyme which utilizes ω6-eicosadienoic acid or ω3-eicosatrienoic acid as a substrate. This isolated nucleic acid sequence can be derived from *Emiliana huxleyi*, preferably, *Emiliana huxleyi* CCMP 378.

In another aspect, the present invention relates to an isolated nucleotide sequence or fragment thereof comprising or complementary to at least 55% of the nucleotide sequence selected from the group consisting of SEQ ID NO:28 and SEQ ID NO:30. The isolated nucleotide sequence or fragment thereof encodes a functionally active Δ8-desaturase enzyme which utilizes ω6-eicosadienoic acid or ω3-eicosatrienoic acid as a substrate. The isolated nucleotide sequence can have a sequence of SEQ ID NO:28. Alternatively, the isolated nucleotide sequence can have a sequence of SEQ ID NO:30. This isolated nucleotide sequence can be derived from *Emiliana huxleyi*, preferably, *Emiliana huxleyi* CCMP 378.

In another aspect, the present invention relates to an expression vector. The expression vector of the present invention comprises a nucleotide sequence operably linked to a regulatory sequence, wherein the nucleotide sequence is comprising or complementary to at least 55% of the nucleotide sequence selected from the group consisting of SEQ ID NO:28 and SEQ ID NO:30.

In yet a further aspect, the present invention relates to a host cell comprising the above described expression vector. The host cell can be an eukaryotic cell. Specifically, the eukaryotic cell is selected from the group consisting of: a mammalian cell, an insect cell, a plant cell and a fungal cell. Examples of fungal cells that can be used are fungal cells selected from the group consisting of: *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. Examples of plant cells that can be used are selected from the group consisting of: soybean, *Brassica* species, safflower, sunflower, maize, cotton and flax.

In yet another aspect, the present invention relates to a plant cell, plant seed, plant or plant tissue comprising the above-described expression vector, wherein expression of the nucleotide sequence of the vector results in production of at least one polyunsaturated fatty acid by the plant cell, plant seed, plant or plant tissue. The polyunsaturated fatty acid produced by said expression vector is selected from the group consisting of: arachidonic acid (ARA), eicosapentaenoic acid (EPA), docosahexaenoic acid (DHA), dihomo-gamma-linolenic acid (DGLA) or ω3-eicosatetraenoic acid (ω3-ETA) and combinations thereof.

In still yet another aspect, the present invention relates to one or more plant oils or fatty acids produced by the plant cell, plant seed, plant or plant tissue described above.

In still yet another aspect, the present invention relates to a purified polypeptide encoded by a nucleotide sequence comprising or complementary to at least 55% of the nucleotide sequence selected from the group consisting of: SEQ ID NO:28 and SEQ ID NO:30.

In still yet another aspect, the present invention relates to purified polypeptide which desaturates a 20-carbon long polyunsaturated fatty acid (C20-PUFA) substrate between carbon atom 8 and carbon atom 9 of the substrate and wherein the polypeptide has at least 55% amino acid identity to an amino acid sequence comprising SEQ ID NO:29.

In still another embodiment, the present invention relates to a purified polypeptide having an amino acid sequence of SEQ ID NO:29.

In still yet another embodiment, the present invention relates to a method of producing an Δ8-desaturase enzyme. The method comprises the steps of:
 a) isolating a nucleotide sequence comprising or complementary to at least 55% of the nucleotide sequence selected from the group consisting of: SEQ ID NO:28 and SEQ ID NO:30;
 b) constructing an expression vector comprising the isolated nucleotide sequence from step a) operably linked to a regulatory sequence; and
 c) introducing the expression vector into a host cell for a time and under conditions sufficient for production of the Δ8-desaturase enzyme.

In the above described method, the host cell is an eukaryotic cell. Specifically, the eukaryotic cell is selected from the group consisting of: a mammalian cell, an insect cell, a plant cell and a fungal cell. Examples of fungal cells that can be used are fungal cells selected from the group consisting of: *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. Examples of plant cells that can be used are selected from the group consisting of: soybean, *Brassica* species, safflower, sunflower, maize, cotton and flax.

In still yet another embodiment, the present invention relates to a method for producing a polyunsaturated fatty acid comprising the steps of:
 a) isolating a nucleotide sequence comprising or complementary to at least 55% of the nucleotide sequence selected from the group consisting of: SEQ ID NO:28 and SEQ ID NO:30;
 b) constructing an expression vector comprising the isolated nucleotide sequence from step a) operably linked to a regulatory sequence;
 c) introducing the expression vector into a host cell for a time and under conditions sufficient for production of an Δ8-desaturase enzyme; and
 d) exposing the expressed Δ8-desaturase enzyme to a substrate selected from the group consisting of: ω6-eicosadienoic acid, ω3-eicosatrienoic acid and combinations thereof in order to convert the substrate to a product polyunsaturated fatty acid.

In the above method, the product polyunsaturated fatty acid is dihomo-gamma-linolenic acid (DGLA), ω3-eicosatetraenoic acid (ω3-ETA) or any combinations thereof.

Additionally, the above described method can further comprise the step of:
 exposing the product polyunsaturated fatty acid to at least one additional desaturase or to an elongase in order to convert the product polyunsaturated fatty acid to another or additional polyunsaturated fatty acid. The product polyunsaturated fatty acid produced is arachidonic acid (ARA), eicosapentaenoic acid (EPA), docosapentaenoic acid (DPA) or docosahexaenoic acid (DHA) or any combinations thereof.

In still another aspect, the present invention relates to a method for producing a polyunsaturated fatty acid in a host cell comprising the steps of:
 a) isolating a nucleotide sequence comprising or complementary to at least 55% of the nucleotide sequence selected from the group consisting of: SEQ ID NO:28 and SEQ ID NO:30;
 b) constructing an expression vector comprising the isolated nucleotide sequence from step a) operably linked to a regulatory sequence;
 c) introducing the expression vector from b) and at least one additional recombinant DNA construct comprising an isolated nucleotide sequence operably linked to at least one regulatory sequence encoding a delta-9 elongase into a host cell;
 d) exposing the expressed Δ8-desaturase enzyme and delta-9 elongase to a substrate selected from the group consisting of: linoleic acid (LA), alpha-linolenic acid (ALA) and combinations thereof in order to convert the substrate to a product polyunsaturated fatty acid.

In the above method, the product polyunsaturated fatty acid is dihomo-gamma-linolenic acid (DGLA) or ω3-eicosatetraenoic acid (ω3-ETA) or any combinations thereof.

The above method can further comprise the step of:
 exposing the product polyunsaturated fatty acid to at least one additional desaturase or to an elongase in order to convert the product polyunsaturated fatty acid to another or additional polyunsaturated fatty acid. The product polyunsaturated fatty acid produced is arachidonic acid (ARA), eicosapentaenoic acid (EPA), docosapentaenoic acid (DPA), docosahexaenoic acid (DHA) or any combinations thereof.

In the above described method, the host cell is an eukaryotic cell. Specifically, the eukaryotic cell is selected from the group consisting of: a mammalian cell, an insect cell, a plant cell and a fungal cell. Examples of fungal cells that can be used are fungal cells selected from the group consisting of: *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. Examples of plant cells that can be used are selected from the group consisting of: soybean, *Brassica* species, safflower, sunflower, maize, cotton and flax.

BRIEF DESCRIPTION OF THE FIGURES

FIGS. 2A and 2B show alignment of amino acid sequence encoded by ED3-8 (SEQ ID NO:29) with known Δ8-desaturases from *Pavlova lutheri* CCMP 459 (SEQ ID NO:2), *Pavlova salina* (SEQ ID NO:3), *Euglena gracialis* (SEQ ID NO:1) and *Perkinsus* (SEQ ID NO:4). Identical residues are highlighted, conserved histidine-boxes are underlined, conserved region in cytochrome b5 domain is underlined (double line).

FIG. 3A shows the Δ8-desaturase amino acid sequences from *Euglena gracialis* (Accession # AF139720, SEQ ID NO:1).

FIG. 3B shows the Δ8-desaturase amino acid sequences from *Pavlova lutheri* CCMP 459 (SEQ ID NO:2).

FIG. 4A shows the Δ8-desaturase amino acid sequences from *Pavlova salina* (Accession # DQ995518, SEQ ID NO:3).

FIG. 4B shows the Δ8-desaturase amino acid sequences from *Perkinsus marinus* (Accession # DQ508730, SEQ ID NO:4).

FIG. 4C shows the Δ8-desaturase amino acid sequences from *Acanthamoenba castellani* (Accession # CS608483, SEQ ID NO:5).

FIG. 5 shows the DNA sequence (SEQ ID NO:11) of clone ED3-8 obtained as described in Example 2.

FIG. 6 shows the deduced amino acid sequence (SEQ ID NO:12) of clone ED3-8 obtained as described in Example 2.

FIG. 7A shows the DNA sequence (SEQ ID NO:15) of clone PK15 obtained as described in Example 2.

FIG. 7B shows the amino acid sequence (SEQ ID NO:16) of clone PK15 obtained as described in Example 2.

FIG. 8A shows the DNA sequence (SEQ ID NO:24) of a clone ED3-8 putative 3'-end obtained as described in Example 2.

FIG. 8B shows the amino acid sequence (SEQ ID NOS:25 and 44-46, respectively, in order of appearance) of a clone ED3-8 putative 3'-end obtained as described in Example 2.

FIG. 9 shows the 1254 base pair gene sequence of the putative Δ8-desaturase from *Emiliana huxleyi* CCMP 378 (SEQ ID NO:28).

FIG. 10 shows the 417 amino acid protein (SEQ ID NO:29) encoded by the 1254 base pair gene sequence (SEQ ID NO:28) of the putative Δ8-desaturase from *Emiliana huxleyi* CCMP 378.

FIG. 11 shows the codon optimized gene sequence of the putative Δ8-desaturase from *Emiliana huxleyi* CCMP 378 (SEQ ID NO:30), designated 'ED3-8-EP2-5-SC'. ED3-8-EP2-5-SC shares 66.98% sequence identity with the original ED3-8 gene sequence (SEQ ID NO:28; FIG. 9). None of the modifications in the codon-optimized gene changed the amino acid sequence of the encoded protein (SEQ ID NO:29; FIG. 10).

FIG. 12 shows the gene sequence of Δ9-elongase derived from *Isochrysis galbana* (IsoD9) (Accession No. CQ831422, SEQ ID NO:31).

DETAILED DESCRIPTION OF THE INVENTION

Figure 1:
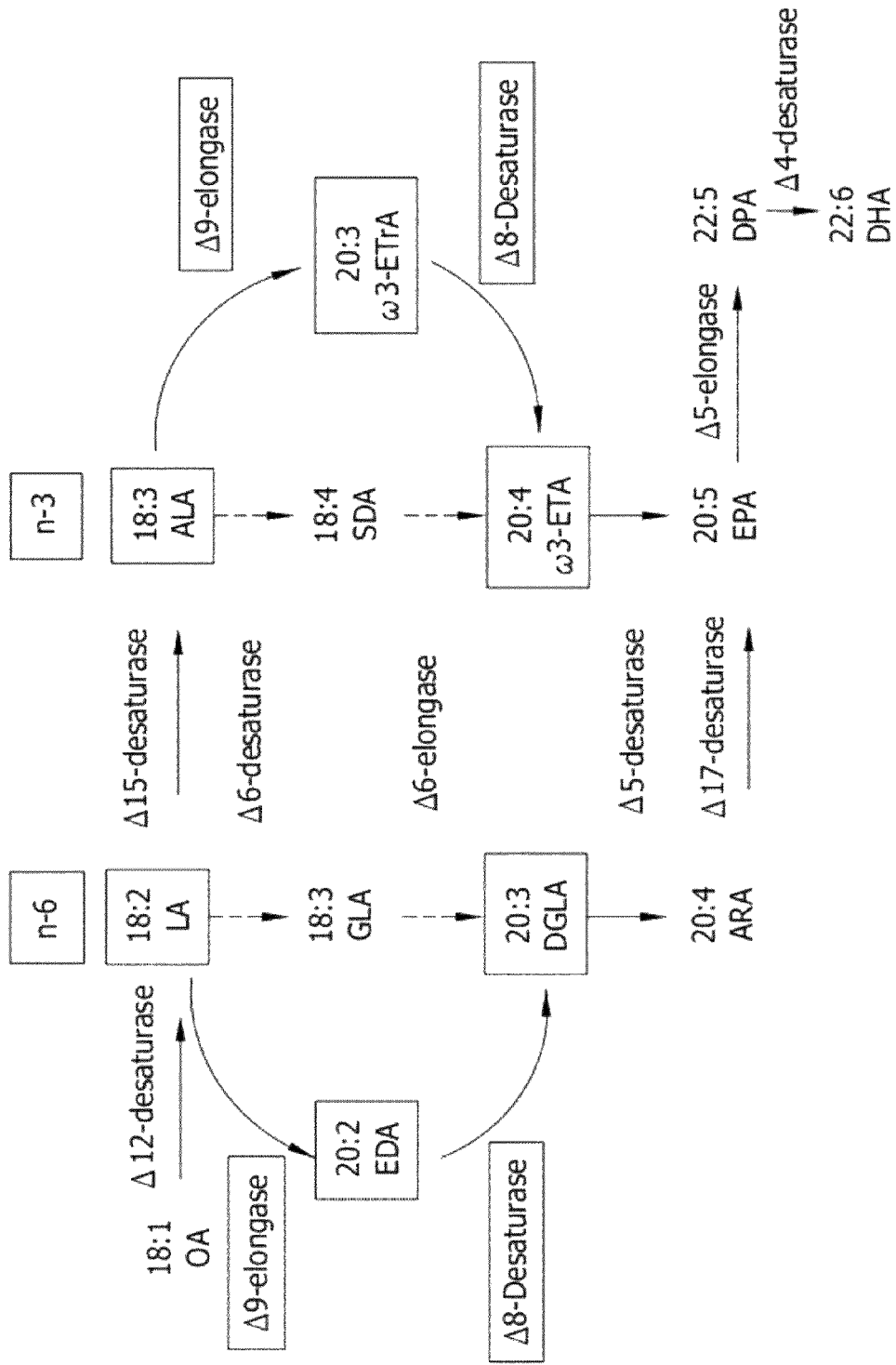
FIG. 1 shows the fatty acid biosynthetic pathway and the role of Δ8-desaturase in this pathway.

The present invention relates to the nucleotide (e.g., gene) and translated amino acid sequences of a Δ8-desaturase gene from *Emiliana* sp., for example, *Emiliana huxley*, specifically, *Emiliana huxley* CCMP 378. Furthermore, the present invention includes uses of the gene and of the enzyme encoded by this gene. For example, the nucleotide and corresponding enzyme may be used in the production of polyunsaturated fatty acids such as, for example, DGLA, ARA, EPA, ω3-ETA DPA and DHA or any combinations thereof which can be added to pharmaceutical compositions, nutritional compositions and to other valuable products.

A. DEFINITIONS

As used herein, the singular forms "a" "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) *Brassica* Species

As used herein, the phrase "*Brassica* species" refers to any plants of *Brassica juncea, Brassica napus, Brassica carinata, Brassica oleracea, Brassica nigra* and *Brassica campestris*.

b) Chimeric Construct

As used herein, the phrase "chimeric construct" refers to a combination of nucleic acid molecules that are not normally found together in nature. Accordingly, a chimeric construct may comprise regulatory sequences and coding sequences that are derived from different sources, or regulatory sequences and coding sequences derived from the same source, but arranged in a manner different than that normally found in nature.

c) Coding Sequence

As used herein, the term "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

d) Codon-Optimized

A "codon-optimized" when used in connection with a gene or nucleic acid molecule refers to a gene or nucleic acid molecule having its frequency of codon usage designed to mimic the frequency of preferred codon usage of the host cell.

e) Complementarity

As used herein, the term "complementarity" refers to the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

f) Encoded by, Hybridization and Stringent Conditions

As used herein, the phrase, "encoded by" refers to a nucleic acid sequence which codes for a polypeptide sequence, wherein the polypeptide sequence or a portion thereof contains an amino acid sequence of at least 3 consecutive amino acids, more preferably at least 8 consecutive amino acids, and even more preferably at least 15 consecutive amino acids from a polypeptide encoded by the nucleic acid sequence.

The present invention also encompasses an isolated nucleotide sequence which encodes for an enzyme having PUFA desaturase activity and that is hybridizable, under stringent conditions, to a nucleic acid having a nucleotide sequence comprising or complementary to the nucleotide sequence comprising SEQ ID NO:28 or SEQ ID NO:30 (See, FIGS. 9 and 11). A nucleic acid molecule is "hybridizable" to another nucleic acid molecule when a single-stranded form of the nucleic acid molecule can anneal to the other nucleic acid molecule under the appropriate conditions of temperature and ionic strength (See, Sambrook et al., *Molecular Cloning: A Laboratory Manual*, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known to those skilled in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (See, Sambrook et al., supra). For hybridization with shorter nucleic acids, the position of mismatches becomes more important, and the length of the oligonucleotide determines its specificity (See, Sambrook et al., supra).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. An example of low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. An example of moderate stringency conditions include hybridization in 40 to 45% formamide, 1 M NaCl, 1% SDS at 37° C., and a wash in 0.5× to 1×SSC at 55 to 60° C. An example of high stringency conditions include hybridization in 50% formamide, 1 M NaCl, 1% SDS at 37° C., and a wash in 0.1×SSC at 60 to 65° C.

g) Exon

As used herein, the term "exon" refers to a portion of the sequence of a gene that is transcribed and is found in the mature messenger RNA derived from the gene, but is not necessarily a part of the sequence that encodes the final gene product.

h) Expression, Antisense Inhibition and Co-suppression

As used herein, the term "expression", refers to the production of a functional end-product. Expression of a gene involves transcription of the gene and translation of the mRNA into a precursor or mature protein.

As used herein, the phrase "antisense inhibition" refers to the production of antisense RNA transcripts capable of suppressing the expression of the target protein.

As used herein, the term "co-suppression" refers to the production of sense RNA transcripts capable of suppressing the expression of identical or substantially similar foreign or endogenous genes (See, U.S. Pat. No. 5,231,020).

i) Fragment or Subfragment that is Functionally Equivalent

The terms "fragment or subfragment that is functionally equivalent" and "functionally equivalent fragment or subfragment", used interchangeably herein refer to a portion or subsequence of an isolated nucleic acid molecule in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense inhibition by linking a nucleic acid fragment or subfragment thereof, whether or not it encodes an active enzyme, in the appropriate orientation relative to a plant promoter sequence.

j) Gene, Native Gene and Transgene

As used herein, the term "gene" refers to a nucleic acid molecule that expresses a specific protein, including regulatory sequences preceding (5' non-coding sequences) and following (3' non-coding sequences) the coding sequence.

As used herein, the phrase "native gene" refers to a gene as found in nature with its own regulatory sequences.

As used herein, the term "transgene" refers to gene that has been introduced into the genome by a transformation procedure.

k) *Gossypium* Species

As used herein, the phrase "*Gossypium* species" refers to any plants of *Gossypium arboreum*, *Gossypium barbadense*, *Gossypium herbaceum*, *Gossypium hirsutum*, *Gossypium hirsutum* var *hirsutum*, *Gossypium hirsutum* var *marie-galante*, *Gossypium lapideum*, *Gossypium sturtianum*, *Gossypium thuberi*, *Gossypium thurberi*, *Gossypium tomentosum* or *Gossypium tormentosum*.

l) Homology

The terms "homology", "homologous", "substantially similar" and "corresponding substantially" are used interchangeably herein and refer to nucleic acid molecules wherein changes in one or more nucleotide bases does not affect the ability of the nucleic acid molecule to mediate gene expression or produce a certain phenotype. These terms also refer to modifications of the nucleic acid molecules of the instant invention such as a deletion or insertion of one or more nucleotides that do not substantially alter the functional properties of the resulting nucleic acid molecule relative to the initial, unmodified molecule. It is therefore understood, as those skilled in the art will appreciate, that the invention encompasses more than the specific exemplary sequences.

m) Host Cell

As used herein, the phrase "host cell" is meant a cell, which comprises an isolated nucleic acid sequence or fragment thereof of the present invention. Host cells may be prokaryotic cells (e.g. such as *Escherichia coli*, cyanobacteria and *Bacillus subtilis*), or eukaryotic cells (e.g. such as fungal, insect, plant or mammalian cells).

Examples of fungal cells that can be used are *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. A particularly preferred fungal cell is *Saccharomyces cerevisiae*.

Plant cells can be monocotyledonous or dicotyledonous plant cells. Particularly preferred plant cells are from *Glycine max* (e.g., soybean), a *Brassica* species, *Carthamus tinctorius* L. (e.g., safflower), *Helianthus annuus* (e.g., sunflower), *Zea mays* (e.g., maize), a *Gossypium species* and *Linum usitatissimum* (e.g, flax).

n) Identity, Sequence Identity and Percentage of Sequence Identity (% Identity)

As used herein, the terms "identity" or "sequence identity" as used interchangeably herein, when used in the context of nucleotide or polypeptide sequences refer to the nucleic acid bases or amino acid residues in two sequences that are the same when aligned for maximum correspondence over a specified comparison window. Thus, identity is defined as the degree of sameness, correspondence or equivalence between the same strands (either sense or antisense) of two DNA or polypeptide segments.

"Percentage of sequence identity" or "% identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, *Appl. Math.* 2:482 (1981), by the algorithm of Needleman & Wunsch, *J. Mol. Biol.* 48:443 (1970), by the method of Pearson & Lipman, *Proc. Natl. Acad. Sci.* (USA) 85:2444 (1988) and by computer programs which implement the relevant algorithms (e.g., Higgins et al., *CABIOS.* 5L151-153 (1989)), FASTDB (Intelligenetics), BLAST (National Center for Biomedical Information; Altschul et al., *Nucleic Acids Research* 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See, U.S. Pat. No. 5,912,120). Useful examples of percent sequence identities include, but are not limited to, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. These identities can be determined using any of the programs described herein.

o) Indirectly or Directly

As used herein, the term "indirectly" when used in connection with the use of a gene and its corresponding enzyme in the production of polyunsaturated fatty acids, encompasses the situation where a first acid is converted to a second acid (i.e., a pathway intermediate) by a first enzyme (e.g., LA to EDA, by, for example a Δ9-elongase) and then the second acid is converted to a third acid by use of a second enzyme (e.g., EDA to DGLA by, for example, Δ8-desaturase).

As used herein, the term "directly" when used in connection with the use of a gene and its corresponding enzyme in the production of polyunsaturated fatty acids encompasses the situation where the enzyme directly converts a first acid to a second acid, wherein the second acid is then utilized in a composition (e.g., the conversion of LA to EDA by, for example a Δ9-elongase or ω3-ETra to ω3-ETA by, for example a Δ8-desaturasae).

p) Intron

As used herein, the term "intron" refers to an intervening sequence in a gene that does not encode a portion of the protein sequence. Thus, such sequences are transcribed into RNA but are then excised and are not translated. The term is also used for the excised RNA sequences.

q) Isolated

As used herein, the term "isolated" refers to a nucleic acid molecule (DNA or RNA) or a protein or a biologically active portion thereof that is removed from its naturally occurring environment or source using routine techniques known in the art (e.g., from bacteria, algae, fungi, plants, vertebrates, mammals, etc.). Isolated nucleic acid molecules or proteins are substantially or essentially free from components that normally accompany or interact with the nucleic acid molecules or proteins in their naturally occurring environment.

r) Isolated Nucleic Acid Fragment or Isolated Nucleic Acid Sequence

As used herein, the phrase "isolated nucleic acid fragment" or "isolated nucleic acid sequence" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately, at least about 10 consecutive nucleotides, at least about 15 consecutive nucleotides, at least about 20 consecutive nucleotides, etc., identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

s) Mature and Precursor

As used herein, the term, "mature" when used in connection with the term "protein" refers to a post-translationally processed polypeptide; i.e., one from which any pre- or propeptides present in the primary translation product have been removed.

As used herein, the term "precursor" when used in connection with the term "protein" refers to the primary product of translation of mRNA; i.e., with pre- and propeptides still present. Pre- and propeptides may be, but are not limited to, intracellular localization signals.

t) 3' Non-Coding Sequences

As used herein, the phrase "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

u) Non-Naturally Occurring

As used herein, the phrase, "non-naturally occurring" refers to something that is artificial, not consistent with what is normally found in nature.

v) Operably Linked

As used herein, the phrase "operably linked" refers to the association of nucleic acid sequences on a single nucleic acid molecule so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

w) Plant

As used herein, the term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

x) Polymerase Chain Reaction or PCR

As used herein, the phrase "Polymerase Chain Reaction" or "PCR" refers to a technique for the synthesis of large quantities of specific DNA segments, consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a cycle.

PCR is a powerful technique used to amplify DNA millions of fold, by repeated replication of a template, in a short period of time (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase. The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

y) Promoter and Enhancer

As used herein, the term "promoter" refers to a DNA sequence capable of controlling the expression of a coding sequence or functional RNA. The promoter sequence consists of proximal and more distal upstream elements, the latter elements are often referred to as enhancers.

As used herein, the term "enhancer" refers to a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters." New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA molecules of some variation may have identical promoter activity.

z) Recombinant

As used herein, the term "recombinant" refers to an artificial combination of two otherwise separated segments of sequence, e.g., by chemical synthesis or by the manipulation of isolated segments of nucleic acids by genetic engineering techniques.

aa) Recombinant Construct, Expression Construct and Recombinant Expression Construct The phrases "recombinant construct", "expression construct" and "recombinant expression construct" are used interchangeably herein and refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid molecules of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

bb) RNA Transcript, Messenger RNA, cDNA, Functional RNA and Endogenous RNA

As used herein, the phrase, "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

As used herein, the phrase "messenger RNA (mRNA)" refers to the RNA that is without introns and that can be translated into protein by the cell.

As used herein, the term "cDNA" refers to a DNA that is complementary to and synthesized from a mRNA template using the enzyme reverse transcriptase. The cDNA can be single-stranded or converted into the double-stranded form using the Klenow molecule of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence.

As used herein, the phrase, "functional RNA" refers to antisense RNA, ribozyme RNA, or other RNA that may not be translated but yet has an effect on cellular processes.

The terms "complement" and "reverse complement" are used interchangeably herein with respect to mRNA transcripts, and are meant to define the antisense RNA of the message.

As used herein, the phrase "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

cc) Similarity

As used herein, the term "similarity" when used when referring to the "similarity" between two amino acid sequences, proteins or polypeptides refers to the presence of a series of identical as well as conserved amino acid residues in both sequences. The higher the degree of similarity between two amino acid sequences, the higher the correspondence, sameness or equivalence of the two sequences.

dd) Stable Transformation, Transient Transformation and Transformation

As used herein, the phrase "stable transformation" refers to the transfer of a nucleic acid molecule into a genome of a host organism, including both nuclear and organellar genomes, resulting in genetically stable inheritance.

In contrast, as used herein, the phrase "transient transformation" refers to the transfer of a nucleic acid molecule into the nucleus, or DNA-containing organelle, of a host organism resulting in gene expression without integration or stable inheritance. Host organisms containing the transformed nucleic acid molecules are referred to as "transgenic" organisms. The preferred method of cell transformation of rice, corn and other monocots is the use of particle-accelerated or "gene gun" transformation technology (Klein et al., (1987) *Nature* (London) 327:70-73; U.S. Pat. No. 4,945,050), or an *Agrobacterium*-mediated method using an appropriate Ti plasmid containing the transgene (Ishida Y. et al., (1996) *Nature Biotech.* 14:745-750).

As used herein, the term "transformation" refers to both stable transformation and transient transformation.

ee) Translation Leader Sequence

As used herein, the phrase "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

All patents, patent publications and priority documents cited herein are hereby incorporated by reference in their entirety.

B. The Δ8-Desaturase Gene and Enzyme Encoded Thereby

The enzyme encoded by the Δ8-desaturase gene of the present invention is essential in the production of polyunsaturated fatty acids (PUFAs) having at least two unsaturations (double bonds) and an overall length of 20 carbon atoms or longer. Specifically, the enzyme of the present invention is functionally active (e.g. has Δ8-desaturase activity), meaning that it adds a double-bond between carbon atom number 8 ($C_8$) and carbon atom 9 ($C_9$) of a PUFA that is at least 20-carbon atoms in length and has pre-existing double bonds at position Δ9, Δ12 and/or Δ15. As shown in FIG. 1, the enzyme encoded by the Δ8-desaturase gene of the present invention produces PUFAs having a length of 20 carbon atoms or longer via the alternate Δ8-desaturase/Δ9-elongase pathway. The substrates, ω6-eicosadienoic acid, ω3-eicosatrienoic acid or both ω6-eicosadienoic acid and ω3-eicosatrienoic acid, are utilized by the Δ8-desaturase of the present invention in this pathway.

The Δ8-desaturase gene of the present invention was isolated from *Emiliana* sp., namely, *Emiliana huxleyi*, specifically, *Emiliana huxleyi* CCMP 378. The nucleotide sequence of the isolated Δ8-desaturase gene from *Emiliana huxleyi* CCMP 378 is shown in FIG. 9 and SEQ ID NO:28. An isolated codon optimized nucleotide sequence of the putative nucleotide sequence is shown in FIG. 11 and SEQ ID NO:30. The isolated or purified amino acid sequence, encoded by both SEQ ID NO:28 and SEQ ID NO:30, is shown in FIG. 10 and SEQ ID NO:29.

The conversion of LA to DGLA and ALA to ω3-ETA using a Δ9-elongase enzyme and a Δ8-desaturase enzyme is referred to as the alternate Δ8-desaturase/Δ9-elongase pathway. The conventional Δ6 pathway for converting LA to DGLA and ALA to ω3-ETA utilizes a Δ6-desaturase enzyme to convert LA to GLA and ALA to SDA, and a Δ6-elongase gene to convert GLA to DGLA, and SDA to ω3-ETA, respectively. In either pathway, the production of ARA or EPA is then catalyzed by, for example, a Δ5-desaturase. DHA, for example, may be produced upon the conversion of EPA to ω3-docosapentaenoic acid (DPA), and ω3-docosapentaenoic acid to DHA, utilizing, for example, a C20-elongase and a Δ4-desaturase, respectively.

Although, for example, DGLA, ARA, ω3-ETrA, ω3-ETA, EPA, DPA and/or DHA can be produced via either the alternate Δ8-desaturase/Δ9-elongase pathway or the conventional 46 pathway, in certain instances, the alternate Δ8-desaturase/Δ9-elongase pathway may be preferred over the conventional Δ6 pathway. For example, if particular residual omega-6 or omega-3 fatty acid intermediates, such as GLA or SDA, are not desired during production of DGLA, ARA, ω3-ETrA, ω3-ETA, EPA, DPA and/or DHA, the alternate Δ8-desaturase/Δ9-elongase pathway may be used as an alternative to the conventional Δ6 pathway, to bypass GLA and SDA formation.

As discussed above, Δ8-desaturase is a necessary enzyme in the alternate Δ8-desaturase/Δ9-elongase pathway. EPA, for example, cannot be synthesized via the alternate Δ8-desaturase/Δ9-elongase pathway without the Δ8-desaturase gene and enzyme encoded thereby. As shown in FIG. 1, the isolated Δ8-desaturase enzyme of the present invention converts, for example, EDA to DGLA and ω3-ETrA to ω3-ETA. The production of ω3-ETA from ω3-ETrA, and EPA from ω3-ETA, is then catalyzed by, for example, a Δ8-desaturase and a Δ5-desaturase, respectively. As a result of using the alternate Δ8-desaturase/Δ9-elongase pathway, the intermediate GLA and SDA fatty acids are bypassed.

The present invention also comprises isolated or purified nucleotide sequences (and the corresponding encoded proteins) having sequences comprising, consisting of or complementary to at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in sequence (i.e., having sequence identity to) SEQ ID NO:28 (the isolated Δ8-desaturase nucleotide sequence from *Emiliana huxleyi* CCMP 378) or SEQ ID NO:30 (the isolated codon optimized nucleotide sequence from *Emiliana huxleyi* CCMP 378). Such sequences may be from human sources as well as other non-human sources (e.g., *C. elegans* or mouse).

Additionally, the present invention also encompasses fragments and derivatives comprising or consisting of the nucleotide sequence of SEQ ID NO:28 or SEQ ID NO:30. Fragments derived from SEQ ID NO:28 or SEQ ID NO:30 can have a length comprising or consisting of 10 to 1250 nucleotides, 10 to 1000 nucleotides, 10 to 750 nucleotides, 10 to 500 nucleotides, 10 to 250 nucleotides, 10 to about 100 nucleotides or 10 to about 50 nucleotides or 15 to 40 nucleotides. In one aspect, the fragments of SEQ ID NO:28 and SEQ ID NO:30 encode a polypeptide having Δ8-desaturase activity. In another aspect, fragments of the SEQ ID NO:28 and SEQ ID NO:30 can be used as primers and probes. Methods of making primers and probes are well known to those skilled in the art. Such primers and probes can have a length of 10 to 50 nucleotides, preferably from 15 to 40 nucleotides.

Variants of the nucleotide sequence of SEQ ID NO:28 and SEQ ID NO:30 are also contemplated herein. Such variants may contain one or more base pair additions, substitutions or deletions, provided that such additions, substitutions or deletions do not occur in any of the three (3) highly conserved "histidine-box" regions or in the cytochrome $b_5$-like domain found at the 5' end of SEQ ID NO:29 (See, FIG. 2). The "histidine-box" regions and cytochrome $b_5$-like domain are discussed in more detail herein in connection with variants of the amino acid of SEQ ID NO:29. Examples of nucleotide variants encompassed by the present invention are shown in Table A below.

TABLE A

| Sequence/Codon Substitution (SEQ ID NO: 28) |
| --- |
| $C_{73} \Rightarrow T_{73}$/CAT $\Rightarrow$ TAT |
| $A_{674} \Rightarrow G_{674}$/AAC $\Rightarrow$ AGC |
| $A_{1001} \Rightarrow T_{1001}$/CAC $\Rightarrow$ CTC |
| $C_{1230} \Rightarrow T_{1230}$/GGC $\Rightarrow$ GGT |
| $T_{65} \Rightarrow C_{65}$/GTC $\Rightarrow$ GCC |
| $C_{73} \Rightarrow T_{73}$/CAT $\Rightarrow$ TAT |
| $A_{674} \Rightarrow G_{674}$/AAC $\Rightarrow$ AGC |
| $A_{1001} \Rightarrow T_{1001}$/CAC $\Rightarrow$ CTC |
| $A_{1037} \Rightarrow G_{1037}$/AAC $\Rightarrow$ AGC |
| $C_{73} \Rightarrow T_{73}$/CAT $\Rightarrow$ TAT |
| $T_{84} \Rightarrow C_{84}$/GCT $\Rightarrow$ GCC |
| $A_{674} \Rightarrow G_{674}$/AAC $\Rightarrow$ AGC |
| $A_{698} \Rightarrow G_{698}$/AAC $\Rightarrow$ AGC |
| $A_{1001} \Rightarrow T_{1001}$/CAC $\Rightarrow$ CTC |
| $G_{1059} \Rightarrow A_{1059}$/TCG $\Rightarrow$ TCA |
| $C_{73} \Rightarrow T_{73}$/CAT $\Rightarrow$ TAT |
| $A_{674} \Rightarrow G_{674}$/AAC $\Rightarrow$ AGC |
| $T_{851} \Rightarrow C_{851}$/GTC $\Rightarrow$ GCC |
| $A_{1001} \Rightarrow T_{1001}$/CAC $\Rightarrow$ CTC |

The present invention also encompasses nucleotide sequences from other sources, and having the above-described complementarity or correspondence to SEQ ID NO:28 or SEQ ID NO:30. Functional equivalents of the SEQ ID NO:28 or SEQ ID NO:30 (i.e., sequences having Δ8-desaturase) are also encompassed by the present invention.

The present invention also encompasses nucleotide sequences or fragments thereof encoding a polypeptide having Δ8-desaturase activity, wherein the amino acid sequence of said polypeptide has at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence comprising SEQ ID NO:29. Such sequences may be from human sources as well as other non-human sources (e.g., *C. elegans* or mouse).

The invention also includes an isolated and/or purified polypeptide which desaturates a polyunsaturated fatty acid through the addition of a double bond between carbon atom number 8 and carbon atom 9 (meaning that it has Δ8-desaturase activity) of a fatty acid that is at least 20 carbon atoms in length and contains an unsaturation at the carbon 9 position and has at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% similarity or identity to the amino acid sequence of SEQ ID NO:29 (shown in FIG. 10). Specifically, the present invention includes a purified polypeptide having an amino acid sequence of SEQ ID NO:29.

Fragments of the polypeptide having the sequence of SEQ ID NO:29 are also contemplated herein. Such fragments can have a length of 10-400 consecutive amino acids, 10-300 consecutive amino acids, 10-200 consecutive amino acids, 10-100 consecutive amino acids, 10-50 consecutive amino acids, 10-40 consecutive amino acids or 10-30 consecutive amino acids, 10-20 amino acids. Such fragments can be used, for example as immunogens in the preparation of antibodies. Alternatively, such fragments can be used as a specific binding partner in one or more immunoassays.

Variants of the polypeptide having the sequence of SEQ ID NO:29 are also contemplated herein. Such variants may contain one or more amino acid additions, substitutions or deletions, provided that such additions, substitutions or deletions do not occur in any of the three (3) highly conserved "histidine-box" regions or in the cytochrome $b_5$-like domain found at the 5' end of SEQ ID NO:29 (See, FIG. 2). The histidine-boxes are found at amino acid positions 155-160 (HDYLH (SEQ ID NO:32)), 197-201 (HNTHH (SEQ ID NO:33)), and 355-359 (QTEHH (SEQ ID NO:34)) of SEQ ID NO:29 (See, FIG. 2). The cytochrome $b_5$-like domain at the 5'-end has a conserved Heme-binding HPGG motif (amino acid position 38-41 of SEQ ID NO:29) (See, FIG. 2). This cytochrome $b_5$-like domain is found in a number of 'front-end' membrane-bound desaturase enzymes such as the Δ6-Δ5- and Δ4-desaturases involved in long chain PUFA production (See, Napier J A et al. (2003) *Prostaglandins Leukot Essent Fatty Acids.* 68:135-43). Cytochrome $b_5$ is believed to function as an electron donor in these enzymes during the process of desaturation reaction, and disruption of this region can result in loss or changes in enzymatic activity (See, Sayanova O et al (1999) *Plant Physiol.* 121:641-646; Guillou H. et al (2004) *J Lipid Res.* 45: 32-40). Examples of amino acid variants encompassed by the present invention are shown in Table B, below.

TABLE B

| Amino Acid Substitution (SEQ ID NO: 29) |
| --- |
| $H_{25} \Rightarrow Y_{25}$ |
| $N_{224} \Rightarrow S_{224}$ |
| $H_{334} \Rightarrow L_{334}$ |
| $V_{22} \Rightarrow A_{22}$ |
| $H_{25} \Rightarrow Y_{25}$ |
| $N_{224} \Rightarrow S_{224}$ |
| $H_{334} \Rightarrow L_{334}$ |
| $N_{346} \Rightarrow S_{346}$ |
| $H_{25} \Rightarrow Y_{25}$ |
| $N_{224} \Rightarrow S_{224}$ |
| $N_{233} \Rightarrow S_{233}$ |
| $H_{334} \Rightarrow L_{334}$ |
| $H_{25} \Rightarrow Y_{25}$ |
| $N_{224} \Rightarrow S_{224}$ |
| $V_{284} \Rightarrow A_{284}$ |
| $H_{334} \Rightarrow L_{334}$ |

C. Production of the Δ8-Desaturase Enzyme

Once the nucleic acid sequence (e.g., gene) encoding a Δ8-desaturase enzyme has been isolated and/or purified, it can then be introduced into either a prokaryotic or eukaryotic host cell through the use of a vector or construct. The vector, for example, a bacteriophage, cosmid, or plasmid, may comprise the nucleotide sequence encoding the Δ8-desaturase enzyme, as well as any regulatory sequence (e.g., promoter) which is functional in the host cell and is able to elicit expression of the Δ8-desaturase encoded by the nucleotide sequence. The regulatory sequence is in operable association with or operably linked to the nucleotide sequence. (A regulatory sequence is said to be "operably linked" with a coding sequence if the regulatory sequence affects transcription or expression of the coding sequence.) Examples of suitable promoters include, but are not limited to, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, enzymes (e.g., a Δ9-elongase), oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (See, *Molecular Cloning: A Laboratory Manual, 2$^{nd}$* ed., Vol. 1-3, ed. Sambrook et al., Cold Spring Harbor Laboratory Press (1989)). The host cell is then cultured under suitable conditions permitting expression of the genes leading to the production of the desired PUFA, which is then recovered and purified using routine techniques known in the art.

Examples of suitable prokaryotic host cells include, but are not limited to, bacteria such as *Escherichia coli, Bacillus subtilis* as well as cyanobacteria such as *Spirulina* spp. (i.e., blue-green algae). The eukaryotic cell includes, but is not limited to, a mammalian cell, an insect cell, a plant cell or a fungal cell. The fungal cell includes, but is not limited to, *Saccharomyces* spp., *Candida* spp., *Lipomyces* spp., *Yarrowia* spp., *Aspergillus* spp., *Penicillium* spp., *Neurospora* spp., *Kluyveromyces* spp., *Hansenula* spp., *Trichoderma* spp., or *Pichia* spp. In particular, the fungal cell may be a yeast cell, including, but not limited to, *Saccharomyces* spp., *Candida* spp., *Hansenula* spp. and *Pichia* spp. The yeast cell can also be *Saccharomyces cerevisiae*. The plant cell includes, but is not limited to, *Glycine max* (e.g., soybean), a *Brassica* species, *Carthamus tinctorius* L. (e.g., safflower), *Helianthus annuus* (e.g., sunflower), *Zea mays* (e.g., maize), a *Gossypium species* and *Linum usitatissimum* (e.g, flax).

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the Δ8-desaturase enzyme and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130-2133 (1997)). Gestation and birth are then permitted (See, e.g., U.S. Pat. No. 5,750,176 and U.S. Pat. No. 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be for example, a mouse, a rat, a rabbit, a pig, a goat, a sheep, a horse and a cow. However, any mammal may be used provided it has the ability to incorporate DNA encoding the enzyme of interest into its genome.

For expression of a Δ8-desaturase polypeptide, functional transcriptional and translational initiation and termination regions are operably linked to the DNA encoding the desaturase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379.

Alternatively, the expressed protein can be an enzyme which produces a product which may be incorporated, either directly or upon further modifications, into a fluid fraction from the host plant. Expression of a Δ8-desaturase gene, or antisense Δ8-desaturase transcripts, can alter the levels of specific PUFAs, or derivatives thereof, found in plant parts and/or plant tissues.

The Δ8-desaturase polypeptide coding region may be expressed either by itself or with other genes (e.g., a gene encoding a Δ9-elongase, a gene encoding a Δ5-desaturase, a gene encoding a Δ17-desaturase, a gene encoding a Δ5-elongase and/or a gene encoding a Δ4-desaturase), in order to produce tissues and/or plant parts containing higher proportions of desired PUFAs or in which the PUFA composition more closely resembles that of human breast milk (See, WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* or *Brassica napus* (canola)) or plant tissue may also be utilized as a host or host cell, respectively, for expression of the Δ8-desaturase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the Δ8-desaturase gene, as well as elongase genes (e.g., Δ9-elongase, Δ5-elongase, etc.) and other desaturase genes (e.g., Δ5-desaturase, Δ17-desaturase, Δ4-desaturase, etc.), in order to provide seed oils that can be added to nutritional compositions, pharmaceutical compositions, animal feeds and cosmetics. Once again, a vector which comprises a DNA sequence encoding the Δ8-desaturase operably linked to a promoter, will be introduced into the plant tissue or plant for a time and under conditions sufficient for expression of the Δ8-desaturase gene. The vector may also comprise one or more genes that encode other enzymes, for example, Δ4-desaturase, Δ5-desaturase, Δ6-desaturase, Δ10-desaturase, Δ12-desaturase, Δ15-desaturase, Δ17-desaturase, Δ19-desaturase, Δ9-elongase, Δ6-elongase and/or Δ5-elongase. The plant tissue or plant may produce the relevant substrate upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: *Methods for Plant Molecular Biology*, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *Bio/Technology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603-618 (1990), Fromm et al., *Bio/Technology* 8:833 (1990), Koziel et al., *Bio/Technology* 11: 194, (1993), Armstrong et al., *Crop Science* 35:550-557 (1995)); oat (Somers et al., *Bio/Technology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect gene constructs (See, generally, Maliga et al., *Methods in Plant Molecular Biology*, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (See, Sambrook et al., *Molecular Cloning: A Laboratory Manual*, Cold Spring Harbor Press (1989); Maliga et al., *Methods in Plant Molecular Biology*, Cold Spring Harbor Press (1995); Birren et al., *Genome Analysis: Detecting Genes,* 1, Cold Spring Harbor, N.Y. (1998); Birren et al., *Genome Analysis: Analyzing DNA,* 2, Cold Spring Harbor, N.Y. (1998); *Plant Molecular Biology: A Laboratory Manual*, eds. Clark, Springer, N.Y. (1997)).

In view of the above, the present invention also encompasses methods of producing a Δ8-desaturase enzyme. Such methods comprise the steps of: 1) isolating a nucleotide sequence comprising or complementary to at least 55% of the nucleotide sequence selected from the group consisting of: SEQ ID NO:28 and SEQ ID NO:30; 2) constructing a vector comprising said nucleotide sequence; and 3) introducing said vector into a host cell under time and conditions sufficient for the production of the Δ8-desaturase enzyme.

The present invention also encompasses methods of producing polyunsaturated fatty acids. In one aspect, the method involves: 1) isolating a nucleotide sequence comprising or complementary to at least 55% of the nucleotide sequence selected from the group consisting of: SEQ ID NO:28 and SEQ ID NO:30; 2) constructing an expression vector comprising the isolated nucleotide sequence from step 1) operably linked to a regulatory sequence; 3) introducing the expression vector into a host cell for a time and under conditions sufficient for production of an Δ8-desaturase enzyme;

and 4) exposing the expressed Δ8-desaturase enzyme to a substrate selected from the group consisting of: ω6-eicosadienoic acid, ω3-eicosatrienoic acid or both ω6-eicosadienoic acid and ω3-eicosatrienoic acid in order to convert the substrate to a first product polyunsaturated fatty acid. Examples of a first product polyunsaturated fatty acid that can be produced by this method are DGLA, ω3-ETA or both DGLA and ω3-ETA. Furthermore, the method can further involve the step(s) of exposing the first product polyunsaturated fatty acid to at least one desaturase or at least one elongase and, optionally, repeating this step (namely, exposing the second or subsequent product polyunsaturated fatty acid to a desaturase or elongase (which can be the same or different from any desaturase or elongase used previously)) to convert the first product polyunsaturated fatty acid (e.g., DGLA and/or ω3-ETA) to a second or subsequent (e.g., third, fourth, fifth, sixth, etc.) product polyunsaturated fatty acid. This step can be repeated as many times as necessary until the desired product polyunsaturated fatty acid is obtained. For example, if the first product polyunsaturated fatty acid is DGLA, the method can further comprise exposing DGLA to a Δ5-desaturase to produce ARA (a second product polyunsaturated fatty acid). Optionally, ARA can then be exposed to a Δ17-desaturase to produce EPA (a third product polyunsaturated fatty acid). Still further optionally, the EPA can be exposed to a Δ5-elongase to produce DPA (a fourth product polyunsaturated fatty acid). Still further optionally, the DPA can be exposed to a Δ4-desaturase to produce DHA (a fifth product polyunsaturated fatty acid).

In another aspect, the method involves: 1) isolating a nucleotide sequence comprising or complementary to at least 55% of the nucleotide sequence selected from the group consisting of: SEQ ID NO:28 and SEQ ID NO:30; 2) constructing an expression vector comprising the isolated nucleotide sequence from step 1) operably linked to a regulatory sequence; 3) introducing the expression vector from 2) and at least one additional recombinant DNA construct comprising an isolated nucleotide sequence operably linked to at least one regulatory sequence encoding a Δ9-elongase (See, for example, U.S. Patent Publication No. 2008/0214667 which describes an isolated nucleotide sequence that encodes a Δ9-elongase) into a host cell; and 4) exposing the expressed Δ8-desaturase enzyme and Δ9-elongase to a substrates selected from the group consisting of: LA, ALA or LA and ALA in order to convert the substrate to a first product polyunsaturated fatty acid. Examples of first product polyunsaturated fatty acids that can be produced by this method are DGLA, ω3-ETA or both DGLA and ω3-ETA. Furthermore, the method can further involve the step(s) of exposing the first product polyunsaturated fatty acid to at least one desaturase or at least one elongase and, optionally, repeating this step (namely, exposing the second or subsequent product polyunsaturated fatty acid to a desaturase or elongase (which can be the same or different from any desaturase or elongase used previously)) to convert the first product polyunsaturated fatty acid (e.g., DGLA and/or ω3-ETA) to a second or subsequent (e.g., third, fourth, fifth, sixth, etc.) product polyunsaturated fatty acid. This step can be repeated as many times as necessary until the desired product polyunsaturated fatty acid is obtained. For example, if the first product polyunsaturated fatty acid is DGLA, the method can further comprise exposing DGLA to a Δ5-desaturase to produce ARA (a second product polyunsaturated fatty acid). Optionally, ARA can then be exposed to a Δ17-desaturase to produce EPA (a third product polyunsaturated fatty acid). Still further optionally, the EPA can be exposed to a Δ5-elongase to produce DPA (a fourth product polyunsaturated fatty acid). Still further optionally, the DPA can be exposed to a Δ4-desaturase to produce DHA (a fifth product polyunsaturated fatty acid).

Thus, as exemplified by the above description, the Δ8-desaturase of the present invention may be used in the production of product polyunsaturated fatty acids which may be used, in turn, for particular beneficial purposes, or may be used in the production of other polyunsaturated fatty acids.

D. Uses of the Δ8-Desaturase Gene

As noted above, the isolated Δ8-desaturase gene and the Δ8-desaturase enzyme encoded thereby have many uses. For example, the gene and corresponding enzyme may be used indirectly or directly in the production of polyunsaturated fatty acids, for example, Δ8-desaturase may be used in the production of DGLA, ARA, EPA, ω3-ETrA, ω3-ETA, DPA and/or DHA. These polyunsaturated fatty acids (i.e., those produced either directly or indirectly by activity of the Δ8-desaturase enzyme) may be added to, for example, nutritional compositions, pharmaceutical compositions, cosmetics, and animal feeds, all of which are encompassed by the present invention. These uses are described, in detail, below.

E. Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced directly or indirectly by use of the Δ8-desaturase gene described herein, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialty infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art.

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substances boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. Thus, fatty acids such as ARA, EPA and/or DHA, produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of ARA, EPA, DGLA, and DHA. More preferably, the oil will comprise from about 0.3 to 30% ARA, and from about 0.2 to 30% DGLA.

Parenteral nutritional compositions comprising from about 2 to about 30 weight percent fatty acids calculated as triglycerides are encompassed by the present invention. Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of ARA and DGLA can be adapted for a particular given end use. When formulated as a breast milk supplement or substitute, a composition which comprises one or more of ARA, DGLA and GLA will be provided in a ratio of about 1:19:30 to about 6:1:0.2, respectively. For example, the breast milk of animals can vary in ratios of ARA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as EDA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of desaturase expression, as well as the expression of elongases (such as, but not limited to, a 49 elongase) and other desaturases, can be used to modulate PUFA levels and ratios. The PUFAs/acids produced in accordance with the present invention (e.g., ARA and EPA) may then be combined with other PUFAs/acids (e.g., DGLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Examples of some of the nutritional supplements, infant formulations, nutritional substitutes and other nutritional solutions that employ the polyunsaturated fatty acids produced pursuant to the present invention are described below.

I. Infant Formulations

A. Isomil® Soy Formula with Iron:

Usage: As a beverage for infants, children and adults with an allergy or sensitivity to cow's milk. A feeding for patients with disorders for which lactose should be avoided: including lactase deficiency, lactose intolerance and galactosemia.

Features:

Soy protein isolate to avoid symptoms of cow's-milk-protein allergy or sensitivity.

Lactose-free formulation to avoid lactose-associated diarrhea.

Low osmolality (200 mOs/kg water).

Dual carbohydrates (corn syrup and sucrose) designed to maximize absorption and minimize risk of malabsorption.

Ingredients: 43.2% Corn Syrup Solids, 14.6% Soy Protein Isolate, 11.5% High Oleic Safflower Oil, 10.3% Sugar (Sucrose), 8.4% Soy Oil, 8.1% Coconut Oil: Less Than 2% Of: Calcium Phosphate, Potassium Citrate, Potassium Chloride, Magnesium Chloride, Sodium Chloride, Ascorbic Acid, Choline Chloride, L-Methionine, Taurine, Ascorbyl Palmitate, Ferrous Sulfate, m-Inositol, Mixed Tocopherols, Zinc Sulfate, d-Alpha-Tocopheryl Acetate, L-Carnitine, Niacinamide, Calcium Pantothenate, Cupric Sulfate, Thiamine Chloride Hydrochloride, Vitamin A Palmitate, Riboflavin, Pyridoxine Hydrochloride, Folic Acid, Potassium Iodide, Potassium Hydroxide, Phylloquinone, Biotin, Sodium Selenate, Beta-Carotene, Vitamin D3 and Cyanocobalamin.

B. Isomil® DF Soy Formula For Diarrhea:

Usage: For the dietary management of diarrhea in infants and toddlers.

Features:

First infant formula to contain added dietary fiber from soy fiber specifically for diarrhea management.

Clinically shown to reduce the duration of loose, watery stools during mild to severe diarrhea in infants.

Lactose-free formulation to avoid lactose-associated diarrhea.

Low osmolality (240 mOsm/kg water) to reduce the risk of osmotic diarrhea.

Ingredients: 85.7% water, 4.8% corn syrup, 2.6% sugar (sucrose), 2.1% soy oil, 2.0% soy protein isolate, 1.4% coconut oil, 0.77% soy fiber, calcium citrate, potassium citrate, calcium phosphate, potassium phosphate, potassium chloride, mono and diglycerides, soy lecithin, magnesium chloride, carrageenan, ascorbic acid, L-methionine, sodium chloride, choline chloride, taurine, ferrous sulfate, m-inositol, d-alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® Advance® Soy Formula with Iron:

Usage: As a beverage for infants, children and adults with an allergy or sensitivity to cow's milk. A feeding for patients with disorders for which lactose should be avoided: including lactase deficiency, lactose intolerance and galactosemia.

Features:

Contains DHA and ARA, two nutrients found in breast milk important for mental and visual development.

Soy protein isolate to avoid symptoms of cow's-milk-protein allergy or sensitivity.

Lactose-free formulation to avoid lactose-associated diarrhea.

Low osmolality (200 mOs/kg water).

Dual carbohydrates (corn syrup and sucrose) designed to maximize absorption and minimize risk of malabsorption.

Ingredients: 43.2% Corn Syrup Solids, 14.6% Soy Protein Isolate, 11.5% High Oleic Safflower Oil, 10.3% Sugar (Sucrose), 8.4% Soy Oil, 7.7% Coconut Oil, *C. cohnii* Oil, *M. alpina* Oil, Calcium Phosphate, Potassium Citrate, Potassium Chloride, Magnesium Chloride, Sodium Chloride, Ascorbic Acid, Choline Chloride, L-Methionine, Taurine, Ascorbyl Palmitate, Ferrous Sulfate, m-Inositol, Mixed Tocopherols, Zinc Sulfate, d-Alpha-Tocopheryl Acetate, L-Carnitine, Niacinamide, Calcium Pantothenate, Cupric Sulfate, Thiamine Chloride Hydrochloride, Vitamin A Palmitate, Riboflavin, Pyridoxine Hydrochloride, Folic Acid, Potassium Iodide, Potassium Hydroxide, Phylloquinone, Biotin, Sodium Selenate, Beta-Carotene, Vitamin D3 and Cyanocobalamin.

D. Isomil® Advance® 20 Soy Formula with Iron Ready to Feed, 20 Cal/Fl Oz.:

Usage: When a soy feeding is desired.

Ingredients: 85.9% water, 6.7% corn syrup, 1.9% soy protein isolate, 1.4% high oleic safflower oil, 1.3% sugar (sucrose), 1.1% soy oil, 1.0% coconut oil, *C. cohnii* oil, *M. alpina* oil, calcium citrate, calcium phosphate, potassium citrate, potassium chloride, mono- and diglycerides, soy lecithin, carrageenan, ascorbic acid, L-methionine, magnesium chloride, potassium phosphate, sodium chloride, choline chloride, taurine, ferrous sulfate, m-inositol, d-alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:

Usage: When an infant formula is needed: if the decision is made to discontinue breastfeeding before age 1 year, if a supplement to breastfeeding is needed or as a routine feeding if breastfeeding is not adopted. Powder, Concentrated Liquid and Ready To Feed forms.

Ingredients: Water, nonfat milk, lactose, high oleic safflower oil, soy oil, coconut oil, whey protein concentrate, potassium citrate, calcium carbonate, ascorbic acid, soy lecithin, monoglycerides, carrageenan, potassium chloride, magnesium chloride, ferrous sulfate, choline chloride, choline bitartrate, taurine, m-inositol, zinc sulfate, niacinamide, d-alpha-tocopheryl acetate, calcium pantothenate, l-carnitine, vitamin A palmitate, riboflavin, cupric sulfate, thiamine chloride hydrochloride, pyridoxine hydrochloride, folic acid, manganese sulfate, phylloquinone, biotin, beta-carotene, sodium selenite, vitamin D3, cyanocobalamin, calcium phosphate, potassium phosphate, sodium chloride, potassium hydroxide and nucleotides (adenosine 5'-monophosphate, cytidine 5'-monophosphate, disodium guanosine 5'-monophosphate, disodium uridine 5'-monophosphate).

F. Similac® Advance® Infant Formula with Iron:

Usage: For use as a supplement or alternative to breastfeeding. Powder, Concentrated Liquid and Ready To Feed forms.

Ingredients: Water, nonfat milk, lactose, high oleic safflower oil, soy oil, coconut oil, whey protein concentrate, *C. cohnii* oil, *M. alpina* oil, potassium citrate, calcium carbonate, ascorbic acid, soy lecithin, monoglycerides, carrageenan, potassium chloride, magnesium chloride, ferrous sulfate, choline chloride, choline bitartrate, taurine, m-inositol, zinc sulfate, niacinamide, d-alpha-tocopheryl acetate, calcium pantothenate, l-carnitine, vitamin A palmitate, riboflavin, cupric sulfate, thiamine chloride hydrochloride, pyridoxine hydrochloride, folic acid, manganese sulfate, phylloquinone, biotin, beta-carotene, sodium selenite, vitamin D3, cyanocobalamin, calcium phosphate, potassium phosphate, sodium chloride, potassium hydroxide and nucleotides (adenosine 5'-monophosphate, cytidine 5'-monophosphate, disodium guanosine 5'-monophosphate, disodium uridine 5'-monophosphate).

G. Similac® NeoSure® Advance® Infant Formula with Iron:
- Usage: A special formula for conditions such as prematurity.
- Features:
- Well absorbed fat blend that contains 25% added medium-chain triglycerides (MCTs).
- Higher levels of protein, vitamins and minerals per 100 Cal than standard term formula.
- More calcium and phosphorus than standard term formula.
- Ingredients: nonfat milk, corn syrup solids, lactose, soy oil, high oleic safflower oil, whey protein concentrate, medium chain triglycerides, coconut oil, *C. cohnii* oil, *M. alpina* oil, potassium citrate, calcium phosphate, m-inositol, ascorbic acid, magnesium chloride, calcium carbonate, taurine, ferrous sulfate, choline bitartrate, choline chloride, ascorbyl palmitate, L-carnitine, potassium chloride, sodium chloride, zinc sulfate, mixed tocopherols, d-alpha-tocopheryl acetate, sodium citrate, niacinamide, potassium phosphate, calcium pantothenate, cupric sulfate, vitamin A palmitate, thiamine chloride hydrochloride, riboflavin, pyridoxine hydrochloride, beta carotene, folic acid, manganese sulfate, phylloquinone, biotin, sodium selenite, vitamin D3, cyanocobalamin and nucleotides (adenosine 5'-monophosphate, cytidine 5'-monophosphate, disodium guanosine 5'-monophosphate, disodium uridine 5'-monophosphate).

H. Similac Natural Care Advance Low-Iron Human Milk Fortifier Ready to Use, 24 Cal/Fl Oz.:
- Usage: Designed to be mixed with human milk or to be fed alternatively with human milk to low-birth-weight infants.
- Ingredients: Water, nonfat milk, corn syrup solids, lactose, medium-chain triglycerides, whey protein concentrate, soy oil, coconut oil, *C. cohnii* oil, *M. alpina* oil, calcium phosphate, potassium citrate, ascorbic acid, calcium carbonate, magnesium chloride, soy lecithin, mono and diglycerides, m-inositol, sodium citrate, carrageenan, choline bitartrate, taurine, choline chloride, niacinamide, d-alpha tocopheryl acetate, L-carnitine, zinc sulfate, potassium chloride, potassium phosphate dibasic, calcium pantothenate, ferrous sulfate, cupric sulfate, riboflavin, vitamin A palmitate, thiamine chloride hydrochloride, pyridoxine hydrochloride, biotin, folic acid, beta carotene, manganese sulfate, phylloquinone, vitamin D3, sodium selenite, cyanocobalamin and nucleotides (adenosine 5'-monophosphate, cytidine 5'-monophosphate, disodium guanosine 5'-monophosphate, disodium uridine 5'-monophosphate).

The various PUFAs of the present invention can be substituted and/or added to the infant formulae described above and to other infant formulae known to those in the art.

II. Nutritional Formulations

A. Ensure®
- Usage: Rich, creamy-tasting ENSURE provides a source of complete, balanced nutrition for supplemental use between or with meals and for interim sole-source feeding. ENSURE can benefit people who are at nutrition risk, experiencing involuntary weight loss, recovering from illness or surgery, or on modified or low-residue diets. For oral feeding. For interim sole-source feeding. Retail product for supplemental oral nutrition
- Ingredients: Water, Sugar (Sucrose), Corn Maltodextrin, Milk Protein Isolate, Soy Oil, Corn Oil, Canola Oil, Soy Protein Concentrate, Potassium Citrate, Natural & Artificial Flavor, Magnesium Phosphate, Sodium Citrate, Soy Lecithin, Calcium Phosphate, Magnesium Chloride, Salt (Sodium Chloride), Choline Chloride, Carrageenan, Ascorbic Acid, dl-Alpha-Tocopheryl Acetate, Ferrous Sulfate, Zinc Sulfate, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Sodium Selenate, Phylloquinone, Potassium Iodide, Vitamin D3 and Cyanocobalamin.

B. Ensure® High Protein:
- Usage: ENSURE HIGH PROTEIN is useful for people who need extra protein and nutrition in their diet. ENSURE HIGH PROTEIN is suitable for use by people recovering from general surgery or hip or other bone fractures, and is a good source of nutrition for those who have or are at risk for pressure ulcers. For supplemental oral nutrition.
- Ingredients: Water, Sugar (Sucrose), Corn Maltodextrin, Calcium and Sodium Caseinates, Soy Oil, Soy Protein Isolate, Corn Oil, Potassium Citrate, Canola Oil, Calcium Phosphate, Sodium Citrate, Magnesium Chloride, Magnesium Phosphate, Artificial Flavor, Salt (Sodium Chloride), Soy Lecithin, Choline Chloride, Ascorbic Acid, Carrageenan, Zinc Sulfate, dl-Alpha-Tocopheryl Acetate, Ferrous Sulfate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

C. Ensure Plus®
- Usage: ENSURE PLUS is a source of complete, balanced nutrition that provides concentrated calories and protein to help patients gain or maintain healthy weight. It can be used with or between meals or as a meal replacement. For oral feeding. For interim sole-source feeding. For patients with fluid restrictions or require volume-limited feedings.
- Features:
- 650 mg omega-3 fatty acid ALA (40% of 1.6 g RDI) to support heart health.
- Excellent source of 24 essential vitamins and minerals.
- Source of antioxidants selenium and vitamins C and E to strengthen the immune system.
- Low in cholesterol.
- Kosher.
- Gluten-free.
- Lactose-free.
- Ingredients: Vanilla: Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

D. Ensure® Powder:

Usage: ENSURE® POWDER (reconstituted with water) is complete, balanced nutrition for supplemental use with or between meals. It may benefit people who are on modified diets, at nutrition risk, experiencing involuntary weight loss, recovering from illness or surgery, or on low-residue diets.

Features:

Convenient, easy to mix

Low residue

Lactose and gluten free

Ingredients: Corn Syrup, Corn Maltodextrin, Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate, Potassium Chloride, Soy Lecithin, Ascorbic Acid, Choline Chloride, Zinc Sulfate, dl-Alpha-Tocopheryl Acetate, Niacinamide, Ferrous Sulfate, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

E. Ensure® Pudding

Usage: ENSURE PUDDING is a nutritious alternative to other snacks or desserts. It provides complete, balanced nutrition in a delicious easy-to-eat form. It is appropriate for those who are underweight or undernourished, or are on a fluid-restricted or volume-limited diet. For people on consistency-modified diets (eg, soft, pureed, or full liquid). For people with swallowing impairments. For supplemental oral nutrition.

Features:

Good source of 24 essential vitamins and minerals.

Convenient-needs no refrigeration.

Gluten-free.

Includes 1 g or FOS per serving (FOS are prebiotics that stimulate the growth of beneficial bacterial in the colon).

Ingredients:

Vanilla: Water, Sugar (Sucrose), Modified Corn Starch, Partially Hydrogenated Soybean Oil, Milk Protein Concentrate, Nonfat Milk, Fructooligosaccharides, Magnesium Sulfate, Potassium Phosphate, Sodium Phosphate, Sodium Stearoyl Lactylate, Artificial Flavor, Sodium Ascorbate, Zinc Sulfate, dl-Alpha-Tocopheryl Acetate, Ferrous Sulfate, Niacinamide, Manganese Sulfate, Calcium Pantothenate, FD&C Yellow #5 & #6, Cupric Sulfate, Thiamine Chloride Hydrochloride, Pyridoxine Hydrochloride, Vitamin A Palmitate, Riboflavin, Folic Acid, Chromium Chloride, Biotin, Sodium Molybdate, Potassium Iodide, Sodium Selenite, Phylloquinone, Vitamin D3 and Cyanocobalamin.

F. Ensure® with Fiber:

Usage: ENSURE FIBER is a source of complete, balanced nutrition for people who can benefit from increased dietary fiber and nutrients. The fiber blend with FOS, a prebiotic, helps maintain digestive-tract health. ENSURE FIBER is suitable for people who do not require a low-residue diet. It can be fed orally or by tube. ENSURE FIBER can benefit people who are on modified diets, are at nutritional risk, are experiencing involuntary weight loss, or are recovering from illness or surgery. For oral feeding. For interim sole-source feeding.

Features:

Includes 1 g of FOS/8 fl oz. FOS fiber (nondigestable carbohydrate) helps promote natural defenses in the colon.

Excellent source of 24 essential vitamins and minerals.

Provides 2.8 g total dietary fiber per 8-fl-oz serving.

Lactose and gluten-free.

Ingredients:

Vanilla: Water; Corn Maltodextrin, Sugar (Sucrose), Sodium and Calcium Caseinates, Soy Oil, Soy Protein Isolate, Corn Oil, Oat Fiber, Fructooligosacchardies, Canola Oil, Soy Fiber, Calcium Phosphate, Magnesium Chloride, Potassium Citrate, Cellulose Gel, Soy Lecithin, Potassium Phosphate, Sodium Citrate, Natural and Artificial Flavors, Choline Chloride, Magnesium Phosphate, Ascorbic Acid, Cellulose Gum, Potassium Chloride, Carrageenan, Ferrous Sulfate, dl-Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

The various nutritional supplements described above and known to others of skill in the art can be substituted and/or supplemented with the PUFAs produced in accordance with the present invention.

G. Oxepa™ Nutritional Product

Oxepa™ is clinically shown to modulate the inflammatory response in critically ill, mechanically ventilated patients. It is appropriate for patients who have sepsis, SIRS (systemic inflammatory response syndrome), ALI (acute lung injury), or ARDS (acute respiratory distress syndrome). For tube feeding. For sole-source nutrition.

Caloric Distribution: The distribution of Calories in Oxepa is shown in Table C.

TABLE C

Caloric Distribution of Oxepa

|  | per 8 fl oz. | per liter | % of Cal |
|---|---|---|---|
| Calories | 355 | 1,500 | — |
| Fat (g) | 22.2 | 93.8 | 55.2 |
| Carbohydrate(g) | 25 | 105.3 | 28.1 |
| Protein (g) | 14.8 | 62.5 | 16.7 |
| Water (g) | 186 | 785 | — |

Ingredients: Water, Calcium and Sodium Caseinates, Sugar (Sucrose), Canola Oil, Medium Chain Triglycerides, Sardine Oil, Borage Oil, Magnesium Chloride, Calcium Phosphate, Soy Lecithin, Potassium Citrate, Sodium Citrate, Ascorbic Acid, Potassium Phosphate, Natural and Artificial Flavor, Choline Chloride, Taurine, d-Alpha-Tocopheryl Acetate, L-Carnitine, Salt (Sodium Chloride), Gellan Gum, Zinc Sulfate, Ferrous Sulfate, Niacinamide, Calcium Pantothenate, Manganese Sulfate, Cupric Sulfate, Thiamine Chloride Hydrochloride, Pyridoxine Hydrochloride, Riboflavin, Beta-Carotene, Vitamin A Palmitate, Folic Acid, Chromium Chloride, Biotin, Sodium Molybdate, Potassium Iodide, Sodium Selenite, Phylloquinone, Vitamin D3 and Cyanocobalamin.

The various fatty acid components of Oxepa™ nutritional product can be substituted and/or supplemented with the PUFAs produced in accordance with this invention.

F. Pharmaceutical Compositions

The present invention also encompasses a pharmaceutical composition comprising one or more of the acids and/or resulting oils produced using the Δ8-desaturase gene described herein, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% ARA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin D F et al., (1993) Am. J. Clin. Nutr. Vol. 57 (Suppl.) 732S-737S). Altered fatty acid metabolism and composition have been demonstrated in diabetic animals.

Furthermore, the compositions of the present invention, comprising PUFAs produced either directly or indirectly through the use of the Δ8-desaturase enzyme, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., (1976) Adv. Exp. Med. Biol. Vol. 83, p. 85-101), reduction or prevention of gastrointestinal bleeding and other side effects of non-steroidal anti-inflammatory drugs (See, U.S. Pat. No. 4,666,701), prevention or treatment of endometriosis and premenstrual syndrome (See, U.S. Pat. No. 4,758,592), and treatment of myalgic encephalomyelitis and chronic fatigue after viral infections (See, U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to preexisting cosmetic compositions such that a mixture is formed or may be used as a sole composition.

G. Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal or aquaculture feed supplements, animal feed substitutes, animal vitamins or in animal topical ointments.

The present invention may be illustrated by the use of the following non-limiting examples.

Example 1

Design of Degenerate Oligonucleotides for the Isolation of a Δ8-Desaturase from *Emiliana huxleyi* CCMP 378 and cDNA Library Construction Analysis of the fatty acid composition of some marine algae revealed the presence of a considerable amount of docosahexaenoic acid (DHA, 22:6 n-3) (40% by weight of total lipids) in *Emiliana huxleyi* CCMP 378 (See, Table 1). In addition, this organism displayed intermediates of the alternate 'Δ8-desaturase-Δ9-elongase' pathway (See, FIG. 1), indicating that this pathway is active in this organism. Thus, it is predicted that this organism would contain an active Δ9-elongase capable of converting linoleic acid (LA, 18:2 n-6) to Eicosadienoic acid (EDA, 20:2 n-6), or alpha-linolenic acid (ALA, 18:3, n-3) to Eicosatrienoic acid (ETrA, 20:3n-3), as well as an active Δ8-desaturase that would convert Eicosadienoic acid (EDA, 20:2 n-6) to Dihomo-gamma-linolenic acid (DGLA, 20:3 n-6), or ω3-Eicosatrienoic acid (ω3-EtrA, 20:3n-3) to ω3-Eicosatetraenoic acid (ω3-ETA, 20:4n-3) (See, FIG. 1).

TABLE 1

Fatty Acid profile of Emiliana huxleyi CCMP378

| Fatty Acid | % Total Lipid |
| --- | --- |
| 18:0 | 0.23 |
| 18:1 n-9 | 2.98 |
| 18:2 n-6 | 1.05 |
| 18:3 n-6 | 0.13 |
| 18:3 n-3 | 3.58 |
| 18:4 n-3 | 14.03 |
| 20:2 n-6 | 0.10 |
| 20:3 n-6 | 0.09 |
| 20:4 n-6 | 0.11 |
| 20:3 n-3 | 6.21 |
| 20:4 n-3 | 0.18 |
| 20:5 n-3 | 1.30 |
| 22:4 n-6 | 0.08 |
| 22:5 n-6 | 0.12 |
| 22:4 n-3 | 0.11 |
| 22:5 n-3 | 1.09 |
| 22:6 n-3 | 40.88 |

The goal of this study was to isolate the predicted full-length Δ8-desaturase gene from *Emiliana huxleyi* CCMP 378 and verify its functionality by expression in *Saccharomyces cerevisiae*. To do so, a normalized cDNA library was constructed for *Emiliana huxleyi* CCMP 378. Cell pellets of *Emiliana huxleyi* CCMP 378 were obtained from Provasoli-Guillard-National Center for Marine Phytoplankton (CCMP-Bigelow Laboratories, West Boothbay, Me.). Total RNA was purified from it using the Qiagen RNeasy Maxi kit (Qiagen, Valencia, Calif.) as per manufacturer's protocol. Briefly, frozen cell pellets were crushed in liquid nitrogen using a mortar and pestle, suspended in RLT buffer (Qiagen RNeasy Plant Mini kit), and passed through a QiaShredder. The RNA was purified using RNeasy maxi columns as per manufacturer's protocol.

Primary and normalized cDNA libraries from *Emiliana huxleyi* CCMP 378 were constructed by Agencourt Biosciences (Waltham, Mass.), using their proprietary technology. Agencourt uses several unique and proprietary steps during first strand that ultimately yields a 25 to 30% increased efficiency over commonly used techniques. During the proprietary process, the RNA is reverse transcribed into ssDNA using conditions designed to reduce or eliminate internal priming events. The combination of this and a specialized cycling program increases the number of full-length clones. Following second strand synthesis, the cDNA clones are then size selected at greater than 1.2 kb to decrease preferential cloning of small, truncated cDNAs. For the large insert library, the insert size selected is >4 kb to enhance for the larger insert clones. Following size selection, cDNA ends are polished and the cDNAs are digested using the rare cutting enzyme. A "rare-cutter" restriction enzyme, the site for which is introduced into the clones during the cDNA priming step, is then used to prepare the clones for directional cloning into the pAGEN vector. The "rare-cutter" restriction enzyme is 20 times less likely to cut within the cDNA clones, thus yielding many more full-length clones versus other cDNA library construction processes, which utilize more common restriction enzymes that cut at random intervals along the clone. The result is an insert with a 5' blunt end and a 3' overhang created from the rare cutting restriction enzyme. Because of this process, no additional adapter ligation is required to ensure directional cloning. This improves the overall efficiency of the cloning process. The vector is specially engineered for directional cloning without the use of 5' adaptors, further enhancing the transformation efficiency due to a reduced number of manipulations of the cDNA during cloning. After the primary cDNA library is complete, it is tested for the number of independent clones, the percentage of recombinant clones and the average insert size.

The normalization process is initiated by dividing the standard library into two populations. The first population is linearized and transcribed from cDNA into RNA, incorporating biotinylated nucleotides. The second population is made into single stranded DNA plasmids via phagemid production. Double stranded DNA in the cell lysate is digested with DNAse I. This eliminates double stranded DNA plasmid contamination from the single stranded DNA prep.

The two populations are then mixed, and any over-represented clones from the ssDNA plasmid will hybridize with their mates from the biotinylated RNA population. Agencourt uses oligo dT and primer extension to pre-block the poly-A region prior to hybridization. This prevents hybridization of the poly-A clone and the poly-U of the RNA. Using a streptavadin/phenol extraction procedure, all biotinylated hybridized pairs and linearized biotinylated RNAs are removed, thus leaving behind the single stranded, under-represented DNA plasmids. Using an oligo which hybridizes only to the clones containing insert, DNA synthesis is primed to re-create the double stranded cDNA clones. The clones are then transformed into bacteria to create the finished normalized cDNA library. Using this protocol, a normalized cDNA library with a titer of $2.6 \times 10^7$ cfu/ml was generated, total number of colonies obtained was $1.8 \times 10^8$, with an average insert size of 1.05 kb.

To isolate Δ8-desaturase-like candidates from the library, degenerate oligonucleotides (i.e., primers) were designed that encoded conserved amino acid motifs present in known Δ8-desaturases. These primers were then used in a PCR reaction to identify DNA fragments that contained these conserved regions in the putative Δ8-desaturase.

Known Δ8-desaturase amino acid sequences from the following organisms were used for alignment and design of primers: *Euglena gracialis* (Accession # AF139720, SEQ ID NO:1; FIG. 3A), *Pavlova lutheri* CCMP 459 (WO 2007/127381A2, SEQ ID NO:2; FIG. 3B), *Pavlova salina* (Accession # DQ995518, SEQ ID NO:3; FIG. 4A), *Perkinsus marinus* (Accession # DQ508730, SEQ ID NO:4; FIG. 4B) and *Acanthamoenba castellani* (Accession # CS608483, SEQ ID NO:5; FIG. 4C).

The degenerate primers used were as follows:

```
Protein motif 1: (SEQ ID NO: 38):
NH3-R D A T D/E A/Q F E/M S/V Y/M H-COOH
Primer RO 1714 (Forward) (SEQ ID NO: 6):
5'-CGC GAC GCG ACG GAS SMG TTC RWG KYK WWS CAC-3'
```

This primer contained the conserved sequence motif in the putative cytochrome b$_5$ domain.

```
Protein Motif 2: (SEQ ID NO: 39):
NH3-G W L A/S H D Y/I L/S H H-COOH
Primer RO 1715 (Forward) (SEQ ID NO: 7):
5'-GGC TGG CTT KCK CAC GAC WWC YYG CAT CAC-3'
```

This primer contained the 'Histidine-box 1' conserved sequence motif.

```
Protein Motif 3: (SEQ ID NO: 40):
NH3-W K/R A/L R H N T/A H H-COOH
Primer RO 1716 (Forward) (SEQ ID NO: 8)
5'-TGG MRS SYG CGC CAT AAC RCG CAC CAC GTG KSC AGC AAC-3'
```

This primer contained the 'Histidine-box 2' conserved sequence motif.

```
Protein Motif 4: (SEQ ID NO: 41):
NH3-F A/G T A/G I/V V V F A T H Y-COOH
Primer RO 1717 (Reverse) (SEQ ID NO:9)
5'-ATA GTG GGT TGC AAA GAC AAC SAY SSC CGT CSC GAA-3'
```

```
Protein Motif 5: (SEQ ID NO: 42):
NH3-Q I/T H H L F P T/M M P-COOH
Primer RO 1718 (Reverse) (SEQ ID NO: 10)
5'-GGG CAT SRT GGG GAA GAG GTG ATG CTC GRT CTG-3'
```

This primer contained the 'Histidine-box 3' conserved sequence motif.

Standard MixBase definition for the oligonucleotide synthesis was: K=G,T; R=A,G; S=C,G; M=A,C; W=A,C; Y=C,T; B=C,G,T; H=A,C,T; V=A,C,G; D=A,T,C; X=A,C,G,T.

Example 2

Isolation of a Putative Δ8-Desaturase Gene from *Emiliana huxleyi* CCMP 378

To isolate a Δ8-desaturase gene from *Emiliana*, various permutations and combinations of the above mentioned degenerate oligonucleotides (See, Example 1) were used in PCR reactions. PCR amplification was carried out in a 50 µl volume containing: 2 µl of the plasmid DNA isolated from the normalized cDNA library as template, 1×PCR buffer minus MgCL$_2$ (20 mM Tris-HCl, pH 8.4, 50 mM KCl), 1.5 mM MgSO$_4$, 200 µM each dNTPs, 2 pmoles of each primer and platinum Taq DNA polymerase (Invitrogen). Amplification was carried out as follows: An initial denaturation at 94° C./3 min, followed by 35 cycles of the following (94° C./30 seconds; 55° C./30 seconds; 72° C./1 minute), a final extension at 72° C./5 minutes, and the reaction was terminated at 4° C. The entire PCR reaction was purified using the Qiagen MinElute Reaction Cleanup Kit (Qiagen Valencia, Calif.) and the reaction was resolved on a 0.8% agarose gel. Bands of appropriate size (based on known Δ8-desaturases) were gel purified using the QiaQuick Gel Extraction Kit (Qiagen), and these DNA fragments were cloned into the TOPO-TA cloning vector (Invitrogen, Carlsbad, Calif.), as per manufacturer's protocol. The recombinant plasmids were transformed into TOP10 supercompetent cells (Invitrogen, Carlsbad, Calif.), and clones were sequenced. Of the various primer sets tried, the only primer combination to generate DNA fragments with sequence similarity to known Δ8-desaturases were RO 1715 and RO 1717.

One clone was thus isolated that showed sequence homology to previously identified Δ8-desaturases. This clone (ED3-8) was 531 bp in length and the deduced amino acid sequence derived from it displayed 62% amino acid sequence identity with the Δ8-desaturase from *Pavlova lutheri* CCMP 459 (See, WO 2007/127381A2, SEQ ID NO: 2; FIG. 3B) as the highest scoring match in a BLAST search. The DNA and deduced amino acid sequence of this clone are indicated (SEQ ID NOS:11 and 12; FIGS. 5 and 6, respectively).

To isolate the 5' end of the ED3-8 fragment, PCR amplification was carried out using plasmid DNA purified from the cDNA library as the template and oligonucleotides (primers): RO 1720 (SEQ ID NO:13) (5'-GAT CAC CGG GCT GTT GCG CAC GAA G-3') and RO 899 (SEQ ID NO:14) (5'-AGCGGATAACAATTTCACACAGGAAACAGC-3').
Primer RO 1720 was designed based on the ED3-8 fragment of this putative Δ8-desaturase, and primer RO 899 corresponded to sequence from the pAGEN vector used for preparation of the cDNA library. Amplification was carried out using 10 pmols of each primer, 1 µl of DNA template, 1.5 µl of 50 mM MgSO$_4$, 1×PCRx buffer (Qiagen), 0.5× enhancer solution (final concentration), 1 µl of 10 mM dNTP, and 0.5 µl platinum Taq DNA polymerase (Qiagen) in a final volume of 50 µl as per manufacturer's instructions. Samples were denatured initially at 94° C. for 2 minutes, followed by 35 cycles of the following: 94° C. for 45 seconds, 55° C. for 30 seconds, 68° C. for 1 minute. A final extension cycle at 68° C. for 7 minutes was carried out before the reaction was terminated at 4° C. The PCR fragments were resolved on a 0.8% agarose gel and gel-purified using the Qiagen Mini-elute Gel Extraction Kit. DNA fragments were cloned into the TOPO-TA cloning vector (Invitrogen). The recombinant plasmids were transformed into TOP10 supercompetent cells (Invitrogen), and clones were sequenced.

Clone PK15 contained a 692 bp insert (SEQ ID NO: 15; FIG. 7A) which was identified to contain the 5'-end of the putative Δ8-desaturase gene based on amino acid sequence homology with known Δ8-desaturases and the presence of the 'ATG' 'Met' start codon. The encoded amino acid sequence of this PK15 clone that contains the 5' end of the putative Δ8-desaturase is indicated (SEQ ID NO: 16; FIG. 7B).

To isolate the 3'-end of this Δ8-desaturase from *Emiliana huxleyi* the following primers were used:

```
Forward primers RO 1719 (SEQ ID NO: 17):
5'-GTA CCA GTG GCT GCT GCT GAC GAT G-3')
or Forward primers RO 1724 (SEQ ID NO: 18):
5'-CTG GCG CTT CGA GTC GAT GCA GTA CCT-3'
or
```

```
Forward primers RO 1727 (SEQ ID NO: 19):
5'-CTT CGT GCG CAA CAG CCC GGT GAT C-3'
and Reverse primer RO 898 (SEQ ID NO: 20):
5'-CCCAGTCACGACGTTGTAAAACGACGGCCAG-3'
```

RO 1719, RO 1724 and RO 1727 were designed based on the sequence of the ED3-8 fragment identified earlier. RO 898 was designed based on the sequence of the pAGEN vector used for cDNA library construction, indicated to PCR amplify the 3'-end of the Δ8-desaturase from the cDNA library. The same PCR conditions were utilized as those described for isolating the 5'-end of ED3-8. However, none of the PCR products thus generated contained the 3'-end of the ED3-8 putative Δ8-desaturase.

PCR was also carried out using the platinum Taq High Fidelity (HF) enzyme (Invitrogen) as per manufacturer's specifications using 1×HF PCR buffer (final concentration) provided, 10 pmols of each primer, 1 µl of DNA template, 1.5 µl of 50 mM MgSO₄, 1 µl of 10 mM dNTP, and 0.5 µl platinum Taq HF DNA polymerase (Qiagen) in a final volume of 50 µl. Samples were denatured initially at 94° C. for 2 minutes, followed by 30 cycles of the following: 94° C. for 30 seconds, 55° C. for 30 seconds, 68° C. for 2 minutes. A final extension cycle at 68° C. for 7 minutes was carried out before the reaction was terminated at 4° C. However, none of the PCR products thus generated contained the 3'-end of the ED3-8 putative Δ8-desaturase.

A final PCR amplification using primers RO 1727 and RO 898 along with the AccuPrime pfx DNA polymerase (Invitrogen) was carried out as per manufacturers' protocol. The PCR reaction included 2 µl of cDNA library DNA template, 1× final concentration of AccuPrime Pfx buffer, 20 pmols of each primer and 1 µl of AccuPrime pfx DNA polymerase in a 50 µl total reaction. Samples were denatured initially at 95° C. for 2 minutes, followed by 30 cycles of the following: 95° C. for 15 seconds, 55° C. for 30 seconds, 68° C. for 1 minute. The reaction was terminated at 4° C. However, none of the PCR products thus generated contained the 3'-end of the ED3-8 putative Δ8-desaturase.

A new strategy was then undertaken to isolate the 3'-end of the putative Δ8-desaturase gene, ED3-8. RACE (Rapid Amplification of cDNA-ends) was carried out using the GeneRace Kit (Invitrogen) to isolate the 3' end. 5 µg of total RNA isolated from *Emiliana* was used, together with GeneRacer Oligo dT primer (5'-GCT GTC AAC GAT ACG CTA CGT AAC GGC ATG ACA GTG (T)₂₄-3' (SEQ ID NO:43)) to generate the first strand cDNA as per manufacturer's specifications.

PCR amplification of the RACE ready cDNA generated above was carried out using 30 pmols of GeneRacer 3' primer (5'-GCT GTC AAC GAT ACG CTA CGT AAC G-3'(SEQ ID NO:22)) and 10 pmols of RO 1724 forward primer (SEQ ID NO:18) that was specific for the putative Δ8-desaturase (ED3-8), as per manufacturer's specifications. The PCR reaction contained 2 µl cDNA template, 1×HF PCR buffer (Invitrogen), 1 µl of 10 mM dNTP, 2 µl of 50 mM MgSO₄, 0.5 µl platinum Taq HF DNA polymerase along with above mentioned primers in a 50 µl total reaction. PCR amplification was carried out as follows: Initial denaturation at 94° C./2 minutes; 5 cycles of denaturation at 94° C./30 seconds; extension at 72° C./1 minute; 5 cycles of denaturation at 94° C./30 seconds; extension at 70° C./1 minute; 20 cycles of denaturation at 94° C./30 seconds; extension at 65° C./30 seconds; final extension at 65° C./10 minute; reaction terminated at 4° C. Analysis of the PCR products revealed very faint bands, probably due to the low proportion of the gene in the cDNA pool. Hence nested PCR was carried out using 1 µl of the above generated PCR reaction as template, along with 10 pmoles of the gene specific primer RO 1719 (SEQ ID NO:17) and 10 pmoles of the GeneRacer 3' nested primer (5'-CGC TAC GTA ACG GCA TGA CAG TG-3' (SEQ ID NO:23)). The PCR reaction was identical to that described for the primary reaction with the RACE ready cDNA template (above). Amplification conditions were as follows: denaturation at 94° C./2 minutes; 25 cycles of denaturation at 94° C./30 seconds, annealing at 65° C./30 seconds, extension at 68° C./1 minute; final extension at 68° C./10 minutes and the reaction terminated at 4° C. Analysis of the PCR fragments on a 0.8% agarose gel revealed the presence of distinct bands. These were gel-purified using the Qiagen Mini-elute Gel Extraction Kit. The ends of the DNA fragments were filled-in using T4 polymerase and resulting blunt-ended fragments were cloned into the TOPO-Blunt cloning vector (Invitrogen). The recombinant plasmids were transformed into TOP10 supercompetent cells (Invitrogen), and clones were sequenced. Sequencing revealed a 589 bp insert (SEQ ID NO:24; FIG. 8A) whose encoded amino acid sequence (SEQ ID NOS: 25 and 44-46; FIG. 8B) contained the putative 3'-end of ED3-8, based on amino acid sequence homology with known Δ8-desaturases and the presence of the 'TAG' stop codon and poly A tail.

The full-length gene of the putative Δ8-desaturase, ED3-8, was isolated by PCR amplification using the following primers:

```
RO 1736 (SEQ ID NO: 26):
(Forward, containing ATG start codon (bold) and an
EcoRI cloning site (underlined)
5'-AAA GAA TTC ATG GGC AAG GGC GGC AAC GCG AAC C-
3'

RO1737 (SEQ ID NO: 27):
(Reverse, containing TGA stop codon (bold) and a
HindIII cloning site (underlined)
5'-AAA AAG CTT CTA GTG CGG CAT CTC TGC CCA CTC G-
3'
```

Templates used for the PCR reaction included either the RACE-ready cDNA or DNA isolated from the normalized cDNA library of *Emiliana*, as follows:
PCR Conditions:

| Template: | cDNA library (2 µl) | RACE-ready cDNA (1 µl) |
|---|---|---|
| 10x Accuprime Pfx Rxn mix (Buffer 1): | 5 ul | 5 ul |
| Primer 1 (10 pmols/ul): | 2 ul | 2 ul |
| Primer 2 (10 pmols/ul) | 2 ul | 2 ul |
| Accuprime Pfx pol (Invitrogen): | 1 ul | 1 ul |
| Water: | 38 ul | 39 ul |
| Total: | 50 ul | 50 ul |

Amplification was carried out as follows: Initial denaturation at 95° C./2 minutes; 30 cycles of (denaturation 95° C./15 seconds; annealing 55° C./30 seconds; extension 68° C./1.5 minutes); final extension at 68° C./4 minutes; reaction terminated at 4° C. PCR resulted in a single band of ~1254 bp, which was cloned into TOPO-Blunt vector (Invitrogen) as per manufacturer's protocol. Both templates resulted in the same size DNA band. Sequencing of the PCR product (ED3-8-EP2-5) obtained from by using the cDNA library as template, revealed the full-length 1254 bp gene sequence of the putative Δ8-desaturase from *Emiliana huxleyi* CCMP 378 (SEQ ID NO:28; FIG. 9), encoding a protein containing 417 amino acids (SEQ ID NO:29; FIG. 10). This gene was designated ED3-8, and was used for expression studies.

In addition to ED3-8, additional variant clones were identified during sequencing that displayed some sequence variations in certain regions of the full-length gene (See, Table 2). These variations are probably caused by mutations that commonly occur during the process of PCR amplification, due to low specificity of the DNA polymerase used. The clones were also obtained when either the cDNA library was used as template (designated ED3-8-EP-X) or when the RACE-ready cDNA was used as template (designated ED3-8-ER-X). These genes were also evaluated for Δ8-desaturase activity, as will be described for the original ED3-8 clone.

The nucleotide sequence encoding the Δ8-desaturase ED3-8 was cloned into pUC57 cloning vector and designated pRSP61. This vector has been deposited with the American Type Culture Collection (ATCC), 10801 University Boulevard, Manassas, Va. 20110 under the terms of the Budapest Treaty on Sep. 9, 2008 and has been accorded ATCC Patent Designation Number PTA-9477.

TABLE 2

Variant clones that display changes in their encoded amino acid sequences in comparison to the original ED3-8-encoded protein

| Clone Name | Sequence/Codon Change | Amino Acid Variation |
|---|---|---|
| ED3-8-EP1-4 | $C_{73} \Rightarrow T_{73}$/CAT$\Rightarrow$ TAT | $H_{25} \Rightarrow Y_{25}$ |
| | $A_{674} \Rightarrow G_{674}$/AAC$\Rightarrow$ AGC | $N_{224} \Rightarrow S_{224}$ |
| | $A_{1001} \Rightarrow T_{1001}$/CAC$\Rightarrow$ CTC | $H_{334} \Rightarrow L_{334}$ |
| | $C_{1230} \Rightarrow T_{1230}$/GGC$\Rightarrow$ GGT | $G_{410} \Rightarrow G_{410}$ (Silent) |
| ED3-8-EP2-1 | $T_{65} \Rightarrow C_{65}$/GTC$\Rightarrow$ GCC | $V_{22} \Rightarrow A_{22}$ |
| | $C_{73} \Rightarrow T_{73}$/CAT$\Rightarrow$ TAT | $H_{25} \Rightarrow Y_{25}$ |
| | $A_{674} \Rightarrow G_{674}$/AAC$\Rightarrow$ AGC | $N_{224} \Rightarrow S_{224}$ |
| | $A_{1001} \Rightarrow T_{1001}$/CAC $\Rightarrow$ CTC | $H_{334} \Rightarrow L_{334}$ |
| | $A_{1037} \Rightarrow G_{1037}$/AAC $\Rightarrow$ AGC | $N_{346} \Rightarrow S_{346}$ |
| ED3-8-ER3-4 | $C_{73} \Rightarrow T_{73}$/CAT$\Rightarrow$ TAT | $H_{25} \Rightarrow Y_{25}$ |
| | $T_{84} \Rightarrow C_{84}$/GCT $\Rightarrow$ GCC | $A_{28} \Rightarrow A_{28}$ (Silent) |
| | $A_{674} \Rightarrow G_{674}$/AAC$\Rightarrow$ AGC | $N_{224} \Rightarrow S_{224}$ |
| | $A_{698} \Rightarrow G_{698}$/AAC$\Rightarrow$ AGC | $N_{233} \Rightarrow S_{233}$ |
| | $A_{1001} \Rightarrow T_{1001}$/CAC$\Rightarrow$ CTC | $H_{334} \Rightarrow L_{334}$ |
| | $G_{1059} \Rightarrow A_{1059}$/TCG$\Rightarrow$ TCA | $S_{353} \Rightarrow S_{353}$ (Silent) |
| ED3-8-ER4-6 | $C_{73} \Rightarrow T_{73}$/CAT$\Rightarrow$ TAT | $H_{25} \Rightarrow Y_{25}$ |
| | $A_{674} \Rightarrow G_{674}$/AAC$\Rightarrow$ AGC | $N_{224} \Rightarrow S_{224}$ |
| | $T_{851} \Rightarrow C_{851}$/GTC$\Rightarrow$ GCC | $V_{284} \Rightarrow A_{284}$ |
| | $A_{1001} \Rightarrow T_{1001}$/CAC$\Rightarrow$ CTC | $H_{334} \Rightarrow L_{334}$ |

Blast analysis revealed that the amino acid sequence encoded by the full-length gene ED3-8 (SEQ ID NO:29) displayed highest amino acid sequence homology to known Δ8-desaturases. These included Δ8-desaturases from *Pavlova lutheri* CCMP 459 ((SEQ ID NO:2; FIG. 3B), *Pavlova salina* (SEQ ID NO: 3; FIG. 4A), *Perkinsus marinus* (SEQ ID NO:4; FIG. 4B) and *Euglena gracialis* (SEQ ID NO:1; FIG. 3A). This encoded protein displayed highest (52.3%) amino acid sequence identity to *Pavlova lutheri* CCMP 459 Δ8-desaturase. It also contained the three conserved 'histidine boxes' found in all known membrane-bound desaturases (Okuley, et al. (1994) *The Plant Cell* 6: 147-158; Pereira S L et al (2003) *Prostaglandins Leukot Essent Fatty Acids.* 68:97-106), that are known to be essential for enzymatic activity (Sayanova O et al. (2001) *J Exp Bot.* 52:1581-1585; Sayanova O et al. (2000) *Biochem Soc Trans.* 28:636-638). The conserved histidine boxes in the protein encoded by ED3-8 were present at amino acid positions 155-160 (HDYLH (SEQ ID NO:32)), 197-201 (HNTHH (SEQ ID NO:33)), and 355-359 (QTEHH (SEQ ID NO:34)) (See, FIG. 2). This sequence also contained a cytochrome $b_5$-like domain at the 5'-end, with the conserved Heme-binding HPGG motif (amino acid position 38-41) (See, FIG. 2). The overall G+C content of this gene is ~65%.

Example 3

Characterization of the Enzymatic Activity of the Putative Δ8-Desaturase Encoded by the Gene ED3-8

The ED3-8 gene encoding the putative Δ8-desaturase was cloned into EcoRI/HindIII sites of the yeast expression vector, pYX242 (Novagen) to generate clone pRSP60, which was then transformed into competent *Saccharomyces cerevisiae* strain SC334. Yeast transformation was carried out using the Alkali-Cation Yeast Transformation Kit (QBioGene) according to conditions specified by the manufacturer. Transformants were selected for leucine auxotrophy on media lacking leucine (DOB [-Leu]).

To determine the specific desaturase activity of the enzyme encoded by ED3-8, transformants were grown in the presence of 50 μM specific fatty acid substrates (listed below) and conversion to specific product was used to determine substrate specificity:

For Δ8-Desaturase Activity:
Eicosadienoic acid (EDA, 20:2 n-6)$\Rightarrow$dihomogamma-linolenic acid (DGLA, 20:3 n-6)
Eicosatrienoic acid (ETrA, 20:3 n-3)$\Rightarrow$to ω3-Eicoastetraenoic acid (ω3-ETA, 20:4 n-3)

For Δ6-Desaturase Activity:
Linoleic acid (18:2 n-6)$\Rightarrow$Gamma-linolenic acid (GLA, 18:3 n-6)
Alpha-linolenic acid (18:3 n-3)$\Rightarrow$Stearidonic acid (SDA, 18:4 n-3)

For Δ5-Desaturase Activity:
Dihomo-gamma-linolenic acid (20:3 n-6)$\Rightarrow$Arachidonic acid (ARA, 20:4 n-6)
ω3-Eicoastetraenoic acid (ω3-ETA, 20:4 n-3)$\Rightarrow$Eicosapentaenoic acid (EPA, 20:5n-3)

For Δ4-Desaturase Activity:
ω6-adrenic acid (ADA, 22:4 n-6)$\Rightarrow$ω6-Docosapentaenoic acid (ω6-DPA, 22:5 n-6)
ω3-Docosapentaenoic acid (ω3-DPA, 22:5 n-3)$\Rightarrow$Docosahexaenoic acid (DHA, 22:6 n-3)

The negative control strain consisted of pYX242 vector expressed in *S. cerevisiae* 334.

The transformed colonies isolated from selective DOB [-Leu] media were grown overnight in 10 ml of YPD liquid broth at 30° C., with vigorous agitation. 5 ml of this overnight culture was then added to 45 ml of selective media (DOB [-Leu]) containing 50 or 25 μM (final concentration) of various fatty acid substrates (as specified), and these were vigorously agitated (250 rpm) for 48 to 72 hours (as indicated) at 24° C.

For total lipid extraction, yeast cells were spun down at 2000 rpm/15 minutes and 0.5 ml water was added, samples vortexed, followed by addition of 10 ml methanol with gentle swirling. 20 ml chloroform was then added, samples were vortexed for 1 minute at high speed and allowed to stand for 2 hours at room temperature. 6 ml saline was then added to the sample followed by centrifugation at 2200 rpm for 10 minutes. The upper chloroform layer was removed to a clean/dry 30 ml vial and chloroform evaporated to dryness at 40° C. under a stream of nitrogen. Once the solvents had completely evaporated, 2 ml chloroform was added to each vial and samples were derivatized.

For derivatization of lipids to Fatty acid methyl esters (FAME), each tube was spiked with 100 μl internal standard (17.216 μg/100 μl) Triheptadecanoin. Chloroform was evaporated to dryness under nitrogen at 40° C., 2 ml Boron Trifluoride in 14% Methanol was added, followed by addition of 2 drops (~50 μl) Toluene. Each vial was flushed with nitrogen, and heated for 15 minutes at 95° C. After vials had cooled, 2 ml saline was added and lipids were extracted with 4 ml hexane by vigorously vortexing for 1 minute. The hexane extract was then transferred into a 20 ml clean/dry screw-cap tube, 5 ml di-$H_2O$ was added and sample vortexed, and centrifuged at 1500 rpm for 4 minutes. The washed hexane was then transferred into a 20 ml reagent tube. Hexane was evaporated to dryness and each sample reconstituted with 0.5 ml fresh hexane. The reconstituted final hexane was vortexed to disperse the lipids. The entire sample was then loaded into the GC auto sampler vials and 4 μl was injected for analysis. The GC was calibrated with the NuChek Std. 461.

The percent conversion of substrate to product was calculated using the formula:

$$\frac{[\text{product}]}{[\text{product}] + [\text{substrate}]} \times 100$$

Table 3 represents the enzyme activity of the ED3-8-encoded protein based on the percent conversion of substrate added. The pRSP60 clone that contained the ED3-8 gene from *Emiliana* converted 1.68% of EDA (20:2 n-6) substrate to DGLA (20:3n-6), and 0.58% of ETrA (20:3n-3) substrate to ETA (20:4n-3). This indicated that the ED3-8 gene encodes a Δ8-desaturase that can recognize both n-6 and n-3 fatty acid substrates, with a preference for the n-6 substrate, EDA. No background (non-specific conversion of substrate) activity was detected with the vector-only control (See, Table 2). The ED3-8 encoded enzyme did not have activity on any of the other substrates tested (data not shown), indicating that it does not have Δ6-, Δ5- or Δ4-desaturase activity.

TABLE 3

Δ8-desaturase activity of ED3-8-encoded protein expressed in *Saccharomyces cerevisiae*

| % Total Fatty Acid | pRSP60 (ED3-8 + pYX242) | pYX242 |
|---|---|---|
| EDA (20:2n-6, Δ11, 14)[a] | 6.91 | 5.10 |
| DGLA (20:3n-6, Δ8, 11, 14)[b] | 0.118 | 0 |
| % Conversion[c] | 1.68 | — |
| ETrA (20:3 n-3, Δ11, 14, 17)[a] | 6.82 | 8.55 |
| ETA (20:4 n-3, Δ8, 11, 14, 17)[b] | 0.04 | 0 |
| % Conversion[c] | 0.58 | — |

[a]Cultures grown in presence of 50 μM substrate at 24° C. for 48 hrs. Numbers represent an average of 3 different experiments.
[b]Amount of product formed
[c]% Conversion = ([product]/{[product] + [substrate]}) × 100

In addition, the other variants of the ED3-8-encoded protein (See, Table 2) were expressed in *S. cerevisiae* under those same growth conditions (See, Table 4). Results indicated that the variants had either lower Δ8-desaturase activity or no activity in comparison to the original ED3-8-encoded protein (See, Table 4). Thus minor changes in the amino acid sequence of ED3-8 can influence enzymatic activity, depending on its location. It is possible that these changes affect the catalytic centers of the enzyme, or the stability of the enzyme resulting in lower activity. Since the crystal structure of these membrane-bound desaturases has not been deciphered as yet, it is not possible to predict every region in the enzyme that is essential for enzymatic activity. It is well known that the 'Histidine-box' regions and the cytochrome $b_5$ region are essential for activity. However none of these ED3-8 variants have changes in the 'Histidine-boxes' or the cytochrome $b_5$ regions (See, Table 2). Thus additional regions in this Δ8-desaturase encoded by ED3-8 were identified that are important for enzyme activity.

TABLE 4

Δ8-desaturase activity of ED3-8 variants expressed in *Saccharomyces cerevisiae*

| Clone | % Conversion[a] (20:2n-6[b] → 20:3n-6) |
|---|---|
| EP3-8-EP1-4 | 0.90 |
| EP3-8-EP2-1 | 0 |
| EP3-8-ER3-4 | 0.37 |
| EP3-8-ER4-6 | 0.49 |
| pYX242 vector | 0 |

[a]% Conversion = ([product]/{[product] + [substrate]}) × 100
[b]Cultures grown in presence of 50 μM substrate at 24° C. for 48 hrs Since the Δ8-desaturase activity of ED3-8 was low under the culturing conditions tested, culturing conditions were modified to determine if activity could be improved in any way, either by changing the amount of substrate added or changing the temperature and time during expression. Thus pRSP60-transformed yeast culture was grown in the presence of 25 μM substrate at 24° C. for 48 hrs or, either 50 μM or 25 μM substrate at 20° C. for 72 hours. Table 5 indicates that changing the culturing conditions can improve expression in yeast. The percent conversion of substrate to product increased from ~1.7% to ~4.5%.

TABLE 5

Δ8-desaturase activity of ED3-8 (pRSP60) when expressed in *Saccharomyces cerevisiae* under differing culturing conditions

| Conditions for expression of pRSP60 | Substrate[a] 20:2n-6 | Product[a] 20:3n-6 | % Conversion[b] |
|---|---|---|---|
| 50 μM substrate at 24° C. for 48 hrs | 6.91 | 0.118 | 1.68% |
| 25 μM substrate at 24° C. for 48 hrs | 8.77 | 0.164 | 1.83% |

TABLE 5-continued

Δ8-desaturase activity of ED3-8 (pRSP60) when expressed in
Saccharomyces cerevisiae under differing culturing conditions

| Conditions for expression of pRSP60 | Substrate[a] 20:2n-6 | Product[a] 20:3n-6 | % Conversion[b] |
|---|---|---|---|
| 50 μM substrate at 20° C. for 72 hrs | 12.05 | 0.535 | 4.2% |
| 25 μM substrate at 20° C. for 72 hrs | 6.283 | 0.368 | 5.53% |

[a]Numbers represent percent of total fatty acids. Average of 3 different experiments.
[b]% Conversion = ([product]/{[product] + [substrate]}) × 100

Example 4

Codon-Optimization of ED3-8 and Expression of its' Encoded Protein in *Saccharomyces cerevisiae*

Since the G+C content of ED3-8 is high (~65%), this could possibly account for the relatively low Δ8-desaturase activity exhibited upon expression in yeast. Thus the codon-usage of ED3-8, the Δ8-desaturase from *Emiliana huxleyi* CCMP 378 (SEQ ID NO:28; FIG. 9) was optimized for expression in *Saccharomyces cerevisiae*. The *Saccharomyces cerevisiae* codon usage pattern was determined from the Codon Usage Database (See, Nakamura, Y., Gojobori, T. and Ikemura, T. (2000) *Nucl. Acids Res.* 28, 292) and this was applied to the ED3-8 gene sequence using the Vector NTI program (Invitrogen). A total of 412 bp of the 1254 bp coding region (~33%) was modified to align the codon-usage with that of *Saccharomyces cerevisiae*. In addition, an internal HindIII site was eliminated to facilitate cloning of the gene into the HindIII site of the multiple cloning site of various expression vectors. Thus a total of 414 bp of the 1254 by coding region were modified. The new codon-optimized sequence shared 66.98% sequence identity with the original ED3-8 gene sequence. None of the modifications in the codon-optimized gene changed the amino acid sequence of the encoded protein (SEQ ID NO:29; FIG. 10). In addition, 'AAA' was added 5' to the ATG translation initiation codon, which is thought to facilitate expression in yeast. This sequence was designated 'ED3-8-EP2-5-SC' (SEQ ID NO:30; FIG. 11). Flanking restriction sites were also added to facilitate cloning into various expression vectors. The designed 'ED3-8-EP2-5-SC' gene was synthesized by GenScript corporation (Piscataway, N.J.) and cloned into the 'TA' cloning region of the pUC57 cloning vector. This gene was then sub-cloned into the EcoRI/SpeI site of the pESC-Ura yeast expression vector (Stratagene) to generate a construct, designated pRSP62.

The clone containing the ED3-8-EP2-5-SC gene (SEQ ID NO:30) cloned into pESC-Ura vector, designated as pRSP62 was deposited with the American Type Culture Collection (ATCC), 10801 University Boulevard, Manassas, Va. 20110 under the terms of the Budapest Treaty on Sep. 26, 2008 and was accorded ATCC patent deposit designation PTA-9532.

pRSP62 was transformed into *Saccharomyces cerevisiae* using the same protocol described in Example 3, and transformants were selected for Uracil auxotrophy using media lacking uracil (DOB[-Ura]) (QBioGene). The transformed colonies isolated from selective DOB[-Ura] media were grown overnight in 10 ml of YPD liquid broth at 30° C., with vigorous agitation. 5 ml of this overnight culture was then added to 45 ml of selective media (Dextrose free-DOB[-Ura]) with 2% galactose (final concentration) added to induce expression of pRSP62 and 50 μM (final concentration) of various fatty acid substrates (as specified). Cultures were vigorously agitated (250 rpm) for 48 hours (as indicated) at 24° C. Isolation and analysis of total fatty acids were also carried out as described in Example 3.

Table 6 represents the enzyme activity of the 'ED3-8-EP2-5-SC'-encoded protein based on the percent conversion of substrate added. The Δ8-desaturase activity of the codon-optimized ED3-8 gene was much higher that of the original ED3-8-encoded protein. Results indicate a 12.51% conversion of EDA (20:2 n-6) substrate to DGLA (20:3n-6), and 8.45% conversion of ETrA (20:3n-3) substrate to ETA (20:4n-3). No background (non-specific conversion of substrate) activity was detected with the pESC-Ura vector-only control (See, Table 6). The codon-optimized ED3-8-encoded enzyme did not demonstrate Δ6-, Δ5- or Δ4-desaturase activity on any of the other substrates tested (data not shown).

TABLE 6

Δ8-desaturase activity of 'ED3-8-EP2-5-SC'-encoded
protein expressed in *Saccharomyces cerevisiae*

| % Total Fatty Acid | pRSP62 (ED3-8-EP2-5-SC) | PESC-Ura vector |
|---|---|---|
| EDA (20:2n-6, Δ11, 14)[a] | 12.90 | 9.95 |
| DGLA (20:3n-6, Δ8, 11, 14)[b] | 1.84 | 0 |
| % Conversion[c] | 12.51 | — |
| ETrA (20:3 n-3, Δ11, 14, 17)[a] | 19.40 | 12.22 |
| ETA (20:4 n-3, Δ8, 11, 14, 17)[b] | 1.79 | 0 |
| % Conversion[c] | 8.45 | — |

[a]Cultures grown in presence of 50 μM substrate at 24° C. for 48 hrs. Numbers represent an average of 2 different experiments.
[b]Amount of product formed.
[c]% Conversion = ([product]/{[product] + [substrate]}) × 100

Example 5

Co-Expression of the Codon-Optimized Δ8-Desaturase 'ED3-8-EP2-5-SC' and the Isochrysis Δ9-Elongase in Yeast The codon-optimized Δ8-desaturase 'ED3-8-EP2-5-SC was co-expressed with a Δ9-elongase nucleic acid sequence derived from *Isochrysis galbana* (IsoD9) (Accession # CQ831422, SEQ ID NO:31; FIG. 12). A synthetic gene construct of IsoD9 gene was made by GenScript (Piscataway, N.J.) and cloned into pUC57 cloning vector. This gene was subcloned into EcoRI/BamHI sites of the pYX242 yeast expression vector and the construct was designated pIsoD9.

Constructs pRSP62 (ED3-8-EP2-5-SC in pESC-Ura) and pIsoD9 were co-transformed into *Saccharomyces cerevisiae* strain SC334 as per protocol described in Example 3. Selection of co-transformants was made using both leucine and uracil auxotrophy (DOB[-Leu-Ura] media). The transformed colonies were grown overnight in 10 ml of YPD liquid broth at 30° C., with vigorous agitation. 5 ml of this overnight culture was then added to 45 ml of selective media (Dextrose free-DOB[-Leu-Ura]+2% Galactose) containing 50 μM (final concentration) of LA (18:2n-6) or ALA (18:3n-3) (as specified), and these were vigorously agitated (250 rpm) for 48 to 72 hours (as indicated) at 24° C. or 20° C. Isolation and analysis of total fatty acids were also carried out as described in Example 3.

TABLE 7

Co-expression of the codon-optimized Δ8-desaturase gene 'ED3-8-EP2-5-SC' (pRSP62) and *Isochrysis* Δ9-elongase gene 'IsoD9' (pIsoD9) in *Saccharomyces cerevisiae*

| % Total Fatty Acid | pRSP62 + pIsoD9 | PESC-Ura + pYX242 |
|---|---|---|
| LA (18:2 n-6) | 13.7 | 19.05 |
| EDA (20:2n-6, Δ11, 14)[b] | 4.97 | 0.100 |
| % Conversion[c] (% Δ9-elongation) | 26.62 | 0.52 |
| EDA (20:2n-6, Δ11, 14)[a] | 2.36 | 0.100 |
| DGLA (20:3n-6, Δ8, 11, 14)[b] | 2.61 | — |
| % Conversion[c] (% Δ8-desaturation) | 52.5 | — |
| LA (18:2 n-6) | 13.7 | 19.05 |
| DGLA (20:3n-6, Δ8, 11, 14)[b] | 2.61 | 0 |
| % Conversion[c] (Δ9-elongation + Δ8-desaturation) | 16.0 | — |

[a]Cultures grown in presence of 50 μM substrate at 24° C. for 72 hrs. Numbers represent an average of 3 different experiments.
[b]Amount of product formed
[c]% Conversion = ([product]/{[product] + [substrate]}) × 100

The Δ8-desaturase and the Δ9-elongase are capable of functioning in concert resulting in the conversion of LA (18:2 n-6) to DGLA (20:3 n-3). The Δ9-elongase (IsoD9) converts LA to EDA (20:2 n-6) and the Δ8-desaturase (ED3-8-EP2-5-SC-encoded enzyme) converts EDA to DGLA. This demonstrates that the Δ8-desaturase encoded by ED3-8 isolated from *Emiliana huxleyi* can function in the alternate (Δ8-desaturase/Δ9-elongase) pathway leading to arachidonic acid (ARA) or EPA/DHA biosynthesis. These enzymes can be thus used in combination with additional desaturases and elongases (i.e. Δ5-desaturase, C20-elongase and Δ4-desaturase) to generate ARA from LA or EPA/DHA from ALA in various hosts.

Example 6

Expression in Plants

The codon-optimized Δ8-desaturase gene 'ED3-8-EP2-5-SC' was co-expressed with a Δ9-elongase gene derived from *Isochrysis galbana* (IsoD9) (Accession # CQ831422, SEQ ID NO:31; FIG. 12), as well as a Δ9-elongase gene derived from *Euglenoid deses* Ehr. CCMP2916 (EugMO7ELO, SEQ ID No:35) (described more fully in U.S. patent application Ser. No. 12/505,293, filed on Jul. 17, 2009, which is incorporated herein by reference to the extent it is consistent herewith) in a model oil-seed plants *Arabidopsis*.

The EugMO7ELO coding sequence (SEQ ID NO: 35) was amplified by PCR from a plasmid containing the corresponding gene with the sense and antisense oligonucleotides: 5'-TATAGAATTCAAATGGACGTCGCGACTACGCTG-3' (SEQ ID NO. 36) and 5'-TATT CTCGAGTTCTAGTCCACTTTCTTCTCATCCTTC-3' (SEQ ID NO 37) (added restriction enzyme recognition sequences are underlined). The PCR reaction was conducted with high-fidelity Phusion polymerase (New England Biolabs). Following restriction enzyme digestion with EcoRI and XhoI, the product was linked on its 5'-end to the seed-specific glycinin-1 promoter from soybean and on its 3'-end to the glycinin-1 3' untranslated region in the binary vector pBinGlyRed2 to generate the plasmid pEugMO7ELO. The glycinin-1 regulatory elements have been previously described (Nielsen, N. C. et al. (1989) Characterization of the glycinin gene family in soybean. *Plant Cell*, 1, 313-328). This vector also contains a Ds-Red transgene under control of the cassaya mosaic virus promoter for selection of transformed seeds by fluorescence and a kanamycin resistance marker for bacterial selection. This vector also contains several unique restriction enzyme sites (e.g., MluI) that enable cloning of other transgenes for multigene gene expression in the host plant. As a control for these experiments, the *Isochrysis galbana* Δ9-ELO (SEQ ID NO: 31) was also cloned as an EcoRI/XhoI fragment under control of the glycinin-1 promoter in pBinGlyRed2 to generate the plasmid pIsoD9.

The ED3-8-EP2-5-SC coding sequence (SEQ ID NO: 30) was synthesized with NotI restriction enzyme sites that flanked the open-reading frame. The ED3-8-EP2-5-SC coding sequence was cloned as a NotI fragment into the corresponding sites of the pBCon vector that contains the seed-specific promoter for the soybean α'-subunit of β-conglycinin gene and the 3' unstranslated region for the phaseolin gene from *Phaseolus vulgaris*. The ED3-8-EP2-5-SC was flanked on its 5' end by the sequence of the β-conglycinin promoter and on its 3' end by the 3' phaseolin untranslated region. The resulting cassette containing the promoter, ED3-8-EP2-5-SC coding sequence, and the 3' untranslated region were removed from the pBCon vector using AscI restriction enzyme sites that flank the cassette. The AscI cassette was subsequently cloned into the compatible MluI site of the pEugELO to generate plasmid pEugMO7ELO-'ED3-8-EP2-5-SC' that contains transgenes for seed-specific co-expression of the EugMO7ELO and ED3-8-EP2-5-SC desaturase. The AscI cassette containing the seed-specific transgene for the ED3-8-EP2-5-SC desaturase was also cloned into the MluI site of pIsoD9 to generate pIsoD9-'ED3-8-EP2-5-SC'.

pEugMO7ELO-'ED3-8-EP2-5-SC' and pIsoD9-'ED3-8-EP2-5-SC' were introduced into *Agrobacterium tumefaciens* strain C58MP90 by electroporation. Kanamycin-resistant *Agrobacterium* was then used for transformation of *Arabidopsis thaliana* ecotype Col-0 by the floral dip method (Clough, S. J. and Bent, A. F. (1998) Floral dip: a simplified method for *Agrobacterium*-mediated transformation of *Arabidopsis thaliana*. *Plant J*, 16, 735-743). Following the *Agrobacterium* floral dip, plants were maintained at 22° C. with 16 h day length until reaching maturity and dry down. For these experiments, a fad3/fae1 mutant of *Arabidopsis* was used that contains low levels of α-linolenic acid and very-long chain fatty acids (≧C20) but elevated levels of linoleic acid in its seed oil (Cahoon, E. B. et al (2006) Conjugated fatty acids accumulate to high levels in phospholipids of metabolically engineered soybean and *Arabidopsis* seeds. *Phytochemistry*, 67, 1166-1176). This genetic background approximates the fatty acid profile of seed oils from crops such as safflower and low linolenic acid soybean. Transgenic seeds obtained from the *Agrobacterium*-dipped *Arabidopsis* plants were identified by fluorescence of the DsRed marker protein using known methodology (Pidkowich, M. S. et al (2007) Modulating seed beta-ketoacyl-acyl carrier protein synthase II level converts the composition of a temperate seed oil to that of a palm-like tropical oil. *Proc Natl Acad Sci USA*, 104, 4742-4747). Single transgenic and non-transgenic control seeds were subjected to direct transesterication of the constituent lipids, including triacylglycerols, by use of trimethylsulfonium hydroxide (TMSH) reagent (Cahoon, E. B. and Shanklin, J. (2000) Substrate-dependent mutant complementation to select fatty acid desaturase variants for metabolic engineering of plant seed oils. *Proc Natl Acad Sci USA*, 97, 12350-12355). Fatty acid methyl esters obtained from the single seeds were analyzed by gas chromatography with flame ionization detection by use of an Agilent 7890 gas chromatograph fitted with an INNOWax column (30 m length×0.25 mm inner diameter) and oven temperature programming from 185° C. (1 min hold) to 230° C. (2 min hold) at 7° C./min. Component fatty acid methyl esters were identified based on their retention times relative to fatty acid methyl esters of known identity from seeds of wild-type Arabidopsis thaliana Col-0 and by comparison of retention times with those of standard fatty acid methyl esters.

Shown in Table 8 are the fatty acid compositions of single $T_1$ seeds from five independent transformation events from plants transformed with pEugMO7ELO-'ED3-8-EP2-5-SC'. Also shown are the fatty acid compositions of single $T_1$ seeds representing independent events from plants transformed with pIsoD9-'ED3-8-EP2-5-SC' (Table 9). Seeds from pEugMO7ELO-'ED3-8-EP2-5-SC' transformants that co-express the Euglena-MO7-elongase and ED3-8 Δ8 desaturase accumulated primarily Δ8,11,14-eicosatrienoic acid (20:3Δ8,11,14) and lesser amounts of Δ11,14-eicosadienoic acid. In these seeds, 20:3Δ8,11,14 was the most abundant fatty acid, and its relative amounts ranged from 28% to 37% of the total fatty acids. Relative amounts of 20:2Δ11,14 in these seeds ranged from 10.8% to 14.5% of the total fatty acids. By comparison, 20:3Δ8,11,14 and 20:2Δ11,4 were not detected or found in only trace amounts in seeds of non-transformed Arabidopsis fad3/fae1 plants (Table 10). In seeds co-expressing the Isochrysis galbana Δ9 ELO and ED3-8 Δ8 desaturase, 20:3Δ8,11,14 accounted for up to 37% of the total fatty acids and 20:2Δ11,14 composed up to 6% of the total fatty acids (Table 9). Overall, these finding show that seeds rich in 18:2 that co-express the Euglena-MO7-elongase and ED3-8 Δ8 desaturase or the Isochrysis galbana Δ9 ELO and ED3-8 Δ8 desaturase can produce substantial amounts of 20:3Δ8,11,14, an immediate biosynthetic precursor of arachidonic acid (20:4Δ5,8,11,14). These findings also demonstrate the viability of co-expression of an 18:2-specific elongase such as the EugMO7ELO and a 20:2 Δ8 desaturase such as the ED3-8 Δ8 desaturase for engineering essential steps in ARA or EPA/DHA production in oilseeds. It is feasible to co-express these genes with a d5-desaturase to achieve the end goal of production of ARA or EPA oils in transgenic oilseeds.

TABLE 8

Fatty acid composition of single $T_1$ transgenic Arabidopsis fad3/fae1 seeds co-expressing genes encoding the Δ9 elongase, EugMO7ELO (SEQ ID NO: 35) and the Δ8-desaturase, ED3-8-EP2-5-SC (SEQ ID NO: 30). Each seed represents an independent transgenic event. Values shown are the wt % of the total fatty acids in the seed.

| Fatty acid | Line 1 | Line 2 | Line 3 | Line 4 | Line 5 |
|---|---|---|---|---|---|
| 16:0 | 6.6 | 9.2 | 5.5 | 8.9 | 9.5 |
| 18:0 | 4.6 | 4.3 | 4.9 | 4.9 | 4.2 |
| 18:1 | 14.5 | 19.7 | 13.0 | 17.8 | 21.1 |
| 18:2 | 18.5 | 20.0 | 23.4 | 25.3 | 19.4 |
| 18:3 | 1.0 | 1.3 | 0.9 | 1.1 | 0.4 |
| 20:0 | 1.0 | 1.2 | 1.1 | 1.2 | 1.1 |
| 20:1 | 1.3 | 2.2 | 1.6 | 1.5 | 2.0 |
| 20:2 | 14.5 | 10.8 | 15.1 | 12.8 | 14.1 |
| 20:3 | 37.1 | 31.1 | 34.3 | 26.4 | 28.3 |

TABLE 9

Fatty acid composition of single $T_1$ transgenic Arabidopsis fad3/fae1 seeds co-expressing genes encoding the Isochrysis galbana Δ9 elongase (IsoD9) (SEQ ID NO: 31) and the Δ8 desaturase, ED3-8-EP2-5-SC.

| Fatty acid | Line 1 | Line 2 | Line 3 |
|---|---|---|---|
| 16:0 | 8.4 | 8.9 | 9.0 |
| 18:0 | 4.2 | 4.6 | 3.3 |
| 18:1 | 32.8 | 23.6 | 17.8 |
| 18:2 | 16.0 | 24.8 | 27.4 |
| 18:3 | 1.0 | 1.3 | 1.4 |
| 20:0 | 1.1 | 1.0 | 1.1 |
| 20:1 | 1.0 | 1.1 | 0.7 |
| 20:2 | 6.1 | 3.5 | 2.6 |
| 20:3 | 27.5 | 31.2 | 36.6 |

Each seed represents an independent transgenic event. Values shown are the wt % of the total fatty acids in the seed.

TABLE 10

Fatty acid composition of single non-transformed Arabidopsis fad3/fae1 seeds (Control).

| Fatty acid | Seed 1 | Seed 2 | Seed 3 | Seed 4 |
|---|---|---|---|---|
| 16:0 | 7.2 | 8.4 | 6.9 | 8.9 |
| 18:0 | 4.2 | 3.9 | 3.2 | 5.3 |
| 18:1 | 31.0 | 34.7 | 40.6 | 32.5 |
| 18:2 | 53.6 | 49.6 | 46.8 | 50.9 |
| 18:3 | 1.8 | 1.8 | 1.0 | 1.3 |
| 20:0 | 1.0 | 0.7 | 0.8 | 1.0 |
| 20:1 | 0.5 | 0.4 | 0.4 | 0.2 |
| 20:2 | ≧0.1 | ≧0.1 | ≧0.1 | ≧0.1 |
| 20:3 | n.d. | n.d. | n.d. | n.d. |

Values shown are the wt % of the total fatty acids in the seed.

The invention illustratively described herein suitably may be practiced in the absence of any element or elements, limitation or limitations which is not specifically disclosed herein. The terms and expressions which have been employed are used as terms of description and not of limitation and there is no intention in the use of such terms and expressions of excluding any equivalents of the features shown and described or portions thereof. It is recognized that various modifications are possible within the scope of the invention as claimed. Thus, it should be understood that although the present invention has been specifically disclosed by preferred embodiments, optional features, modifications and variations of the concepts herein disclosed may be resorted to by those skilled in the art and such modifications and variations are considered to be within the scope of this invention as defined by the appended claims.

SEQUENCE LISTING

<160> NUMBER OF SEQ ID NOS: 46

<210> SEQ ID NO 1

<211> LENGTH: 419
<212> TYPE: PRT
<213> ORGANISM: Euglena gracialis

<400> SEQUENCE: 1

```
Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Pro Leu Ala Trp Ser Glu Asp Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400
```

Arg Tyr Leu Ala Val Phe Ala Arg Met Ala Glu Lys Gln Pro Ala Gly
                405                 410                 415

Lys Ala Leu

<210> SEQ ID NO 2
<211> LENGTH: 423
<212> TYPE: PRT
<213> ORGANISM: Pavlova lutheri

<400> SEQUENCE: 2

Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Glu Arg Asp Ala Thr
    50                  55                  60

Glu Gln Phe Glu Ser Tyr His Ser Pro Lys Ala Ile Lys Met Met Glu
65              70                  75                  80

Gly Met Leu Lys Lys Ser Glu Asp Ala Pro Ala Ser Val Pro Leu Pro
            85                  90                  95

Ser Arg Ser Thr Met Gly Thr Glu Phe Lys Glu Met Ile Glu Arg His
        100                 105                 110

Lys Arg Ala Gly Leu Tyr Asp Pro Cys Pro Leu Asp Glu Leu Phe Lys
    115                 120                 125

Leu Thr Ile Val Leu Ala Pro Ile Phe Val Gly Ala Tyr Leu Val Arg
130                 135                 140

Ser Gly Val Ser Pro Leu Ala Gly Ala Leu Ser Met Gly Phe Gly Phe
145                 150                 155                 160

Tyr Leu Asp Gly Trp Leu Ala His Asp Tyr Leu His His Ala Val Phe
                165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
        195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225                 230                 235                 240

Ala Lys Arg Leu Asn Phe Phe Gln Arg Trp Gln Gln Tyr Tyr Tyr Val
                245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Ala Leu
        275                 280                 285

Ala Ala His Tyr Ala Leu Leu Cys Trp Val Phe Ala Ala His Leu Asn
    290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
                325                 330                 335

Glu Gly Met Thr Leu Val Glu Gln Thr Ala Lys Thr Ser Arg Asn Ile
            340                 345                 350

```
Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
                405                 410                 415

Ala Phe Glu His Leu Leu His
                420

<210> SEQ ID NO 3
<211> LENGTH: 427
<212> TYPE: PRT
<213> ORGANISM: Pavlova salina

<400> SEQUENCE: 3

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
290                 295                 300
```

```
Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425

<210> SEQ ID NO 4
<211> LENGTH: 457
<212> TYPE: PRT
<213> ORGANISM: Perkinsus marinus

<400> SEQUENCE: 4

Met Thr Thr Ser Thr Thr Thr Val Gln Leu Gln Glu Asp Leu Ser Ser
1               5                   10                  15

Gly Asp Gln Asn Ala His Pro Ser Pro Ser Arg Ala Thr Pro Ser Val
            20                  25                  30

Gly Asp Thr Lys Glu Asp Ala Arg Val Val Ile Lys Leu Phe Gly Thr
        35                  40                  45

Trp Val Asp Val Thr Ala Trp Leu Asn Asp His Pro Gly Gly Ser Lys
    50                  55                  60

Val Leu Arg Ala Phe Asn Lys Lys Asp Ala Thr Asp Ala Val Met Ala
65                  70                  75                  80

Met His Thr Asp Glu Ala Ile Lys Arg Ile Ile Arg Phe Ser Asn Val
                85                  90                  95

Val Ser Ser Ala Pro Ile Asn Ala Ser Ile Gly Asp Val Gln Val Ile
            100                 105                 110

Glu Lys Ser Leu Ser Arg Glu Gln Leu Met Tyr Tyr Lys Leu Arg Thr
        115                 120                 125

Leu Ala Arg Asn Gln Gly Trp Phe Gln Ser Asn Leu Leu Tyr Glu Gly
    130                 135                 140

Val Lys Ala Met Ile Ala Phe Gly Leu Leu Ile Ile Gly Phe Ala Thr
145                 150                 155                 160

Leu Tyr Phe Asp Tyr Gly Ile Trp Ser Thr Ala Leu Ile Gly Phe Ala
                165                 170                 175

Trp Phe Gln Leu Gly Trp Leu Gly His Asp Trp Ser His His Thr Ala
            180                 185                 190

Leu Pro Lys Ser Thr Thr Asn Cys Ala Asn Tyr Asn Asp Tyr Leu Gly
        195                 200                 205

Trp Leu Thr Gly Leu Ala Arg Gly Asn Thr Leu Leu Trp Trp Lys Leu
    210                 215                 220

Arg His Asn Thr His His Val Leu Thr Asn Gln Tyr Glu Asn Asp Pro
225                 230                 235                 240

Asp Ile Leu Thr Gln Pro Pro Leu His Phe Phe Glu Asp Phe Asp Val
                245                 250                 255

-continued

```
Gly Asn Val Asn Arg Tyr Gln Ala Val Tyr Tyr Leu Pro Met Leu Thr
            260                 265                 270

Leu Leu His Leu Phe Trp Leu Tyr Glu Ser Val Leu Val Cys Leu Arg
        275                 280                 285

Gln Ser Lys Ser Ile Asn Arg Tyr Asn Arg Met His Ala Arg Arg Asp
    290                 295                 300

Thr Val Ala Leu Val Leu His Ile Leu Ile Val Gly Ile Ile Ser Tyr
305                 310                 315                 320

Thr Ser Gly Lys Tyr Leu Leu Ile Leu Leu Ala Tyr Met Leu Ser Gly
                325                 330                 335

Phe Leu Thr Ala Val Val Val Phe Ala Ser His Tyr Asn Glu Pro Arg
            340                 345                 350

Val Ala Ser Gly Glu Ser Leu Ser Leu Val Arg Gln Thr Leu Leu Thr
        355                 360                 365

Thr Ile Asn Ile Gly Ser Phe Ser Asp Thr His Trp Glu Lys Lys Leu
    370                 375                 380

Trp Phe Tyr Leu Thr Gly Gly Leu Asn Met Gln Ile Glu His His Leu
385                 390                 395                 400

Phe Pro Thr Met Pro Arg His Asn Leu Pro Lys Thr Thr Phe Leu Val
                405                 410                 415

Lys Ser Leu Ala Gln Glu Leu Gly Leu Pro Tyr Lys Glu Thr Asn Ile
            420                 425                 430

Val Ser Leu Thr Lys Ala Ala Val Thr Thr Leu His His Asn Ala Leu
        435                 440                 445

Arg Asn Ile Glu Arg Leu Leu Ala Arg
    450                 455

<210> SEQ ID NO 5
<211> LENGTH: 456
<212> TYPE: PRT
<213> ORGANISM: Acanthamoenba castellani

<400> SEQUENCE: 5

Met Val Leu Thr Thr Pro Ala Leu Asn Leu Lys Lys Glu Arg Thr Ser
1               5                   10                  15

Phe Thr Gln Glu Ile Ser Lys Leu Trp Val Leu His Gly Gln Val Tyr
            20                  25                  30

Asp Phe Thr Asp Phe Val Lys Tyr His Pro Ala Gly Ser Arg Ala Ile
        35                  40                  45

Leu Leu Gly Arg Gly Arg Asp Cys Thr Val Leu Phe Glu Ser Tyr His
    50                  55                  60

Thr Val Leu Pro Ser Asp Ala Leu Asp Glu Lys Tyr Arg Val Ser Ala
65                  70                  75                  80

Pro Asn Ala Lys Leu Glu Glu Ser Arg Ser Ala Lys Leu Phe Ser Phe
                85                  90                  95

Glu Glu Gly Ser Phe Tyr Arg Thr Leu Lys Gln Arg Thr Arg Glu Tyr
            100                 105                 110

Phe Lys Thr Asn Asn Leu Ser Thr Lys Ala Thr Thr Met Glu Val Ile
        115                 120                 125

Tyr Phe Val Ala Thr Ile Leu Ser Ile Tyr Phe Cys Thr Trp Ala Ala
    130                 135                 140

Phe Val Gln Gly Ser Leu Ile Ala Ala Val Leu His Gly Val Gly Arg
145                 150                 155                 160

Ala Ile Cys Ile Ile Gln Pro Ile His Ala Thr Ser His Tyr Ala Met
                165                 170                 175
```

Phe Arg Ser Val Trp Leu Asn Gln Trp Ala Tyr Arg Ile Ser Met Ala
            180                 185                 190

Val Ser Gly Ser Ser Pro Ala Gln Trp Thr Thr Lys His Val Ile Asn
        195                 200                 205

His His Val Glu Thr Asn Leu Cys Pro Thr Asp Asp Thr Asn Tyr
    210                 215                 220

Pro Ile Lys Arg Ile Leu His Glu Phe Pro Arg Ile Phe Phe His Lys
225                 230                 235                 240

Tyr Gln His Ile Tyr Ile Trp Leu Val Tyr Pro Tyr Thr Thr Ile Leu
                245                 250                 255

Trp His Phe Ser Asn Leu Ala Lys Leu Ala Leu Gly Ala Ala Arg Gly
            260                 265                 270

Gln Met Tyr Glu Gly Ile Ala Lys Val Ser Gln Glu Thr Ser Gly Asp
        275                 280                 285

Trp Val Glu Thr Ala Met Thr Leu Phe Phe Thr Phe Ser Arg Leu
    290                 295                 300

Leu Leu Pro Phe Leu Cys Leu Pro Phe Thr Thr Ala Ala Ala Val Phe
305                 310                 315                 320

Leu Leu Ser Glu Trp Thr Cys Ser Thr Trp Phe Ala Ile Gln Phe Ala
                325                 330                 335

Val Ser His Glu Val Asp Glu Cys Val Glu His Glu Lys Ser Val Leu
            340                 345                 350

Asp Thr Ile Lys Ala Asn Glu Ala Lys Gly Ile Val Asn Gln Gly Gly
        355                 360                 365

Leu Val Asp Trp Gly Ala His Gln Val Arg Ala Ser His Asn Tyr Ser
    370                 375                 380

Ala Asp Ser Leu Leu Ser Leu His Phe Ser Gly Gly Leu Asn Leu Gln
385                 390                 395                 400

Ile Glu His His Leu Phe Pro Ser Val His Tyr Thr His Tyr Pro Ala
                405                 410                 415

Pro Ser Lys Leu Val Gln Gln Thr Cys Lys Glu Phe Asn Leu Pro Cys
            420                 425                 430

Thr Leu Ser Pro Ser Met Met Gly Ala Val Thr Lys His Tyr His Gln
        435                 440                 445

Leu Lys Lys Met Gly Ala Glu Asn
    450                 455

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgcgacgcga cggassmgtt crwgkykwws cac                              33

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggctggcttk ckcacgacww cyygcatcac                                  30

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggmrssygc gccataacrc gcaccacgtg kscagcaac                               39

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atagtgggtt gcaaagacaa csayssccgt cscgaa                                  36

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggcatsrtg gggaagaggt gatgctcgrt ctg                                     33

<210> SEQ ID NO 11
<211> LENGTH: 531
<212> TYPE: DNA
<213> ORGANISM: Emiliana huxleyi

<400> SEQUENCE: 11
gcccttggga gggtgcgcca taacgcgcac cacgtgggca gcaacgaaga aggcaacgac        60
cccgacatca tgaccgcgcc tgtgctcatc ttcgtgcgca acagcccggt gatcgccgct       120
gccctcaacg cggcgcagcg gtggcagcag tactactacg tgcccgcgat gagcctcatg       180
gacatgtact ggcgcttcga gtcgatgcag tacctggccg cgcggcccct caacaaggtc       240
tgggcctcgt gggcgctcct cgcgctgcac tactcctttg tcggctacat gttccacgga       300
cagtaccagt ggctgctgct gacgatgctg gtgcgcggct tcctcacggg catcgtcgtc       360
ttctcgacgc attatggcga ggaggtcatc ccgggcgacc acggcatgac actcgtcgag       420
cagacggcgc tcacctctcg caacatcacc ggcgggtacc tcgtcaacct gctcacgggc       480
tacatctcgc tgcagaccga gcatcacctc ttccccatga tgcccaaggg c                531

<210> SEQ ID NO 12
<211> LENGTH: 177
<212> TYPE: PRT
<213> ORGANISM: Emiliana huxleyi

<400> SEQUENCE: 12

Ala Leu Trp Arg Val Arg His Asn Ala His His Val Gly Ser Asn Glu
 1               5                  10                  15

Glu Gly Asn Asp Pro Asp Ile Met Thr Ala Pro Val Leu Ile Phe Val
             20                  25                  30

Arg Asn Ser Pro Val Ile Ala Ala Ala Leu Asn Ala Ala Gln Arg Trp

```
                35                  40                  45
Gln Gln Tyr Tyr Tyr Val Pro Ala Met Ser Leu Met Asp Met Tyr Trp
 50                  55                  60
Arg Phe Glu Ser Met Gln Tyr Leu Ala Ala Arg Pro Phe Asn Lys Val
 65                  70                  75                  80
Trp Ala Ser Trp Ala Leu Leu Ala Leu His Tyr Ser Phe Val Gly Tyr
                 85                  90                  95
Met Phe His Gly Gln Tyr Gln Trp Leu Leu Leu Thr Met Leu Val Arg
            100                 105                 110
Gly Phe Leu Thr Gly Ile Val Val Phe Ser Thr His Tyr Gly Glu Glu
        115                 120                 125
Val Ile Pro Gly Asp His Gly Met Thr Leu Val Glu Gln Thr Ala Leu
    130                 135                 140
Thr Ser Arg Asn Ile Thr Gly Gly Tyr Leu Val Asn Leu Leu Thr Gly
145                 150                 155                 160
Tyr Ile Ser Leu Gln Thr Glu His His Leu Phe Pro Met Met Pro Lys
                165                 170                 175
Gly
```

```
<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatcaccggg ctgttgcgca cgaag                                         25

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcggataac aatttcacac aggaaacagc                                    30

<210> SEQ ID NO 15
<211> LENGTH: 672
<212> TYPE: DNA
<213> ORGANISM: Emiliana huxleyi
<220> FEATURE:
<221> NAME/KEY: modified_base
<222> LOCATION: (572)..(573)
<223> OTHER INFORMATION: a, c, g, or t

<400> SEQUENCE: 15
atgggcaagg gcggcaacgc gaacccgcgg gagctcaaag gcggcaaggc cgagcagctg    60
acagtctacc tgtatggcaa ggctgtcgac gtctcgaagt tcgcgaagct gcacccggga   120
ggcgccaagg cgctgcgcat cttcaacaac cgtgacgcca ccgagcagtt cgagatgtac   180
cactcgcccg ccgcccacaa gatgatgcgt gcgatgtcga agagcgcgcc ggaggccccg   240
agggagagcg aggtcgcgac gtcggtcgtt ggacggact tcgccaagct gacgcagacg    300
ctgcacgacg tcgatgcgtt cgaccctcac tacccagacg aggccttcaa gctcggcctc   360
acgctgctgc ccggattcct cggcttctac ctgctgcgga gcggcatgcc ggcgctcgga   420
```

```
tccttcctga tcgctttctc gtactacatg tctgggtgga cctcccacga ttacttgcac    480
cacggctgcc tcaagggcgg ccaaaagcag ctggtgcact ggaacaacgc cgtcggctac    540
gcaatcggcg cttggcaggg ctacgcggtc gnntggtggc gagcgcgcca caacacgcac    600
cacctcgtca cgaacgaaga aggcaacgac cccgacatca tgaccgcgcc tgtgctcatc    660
ttcgtgcgca ac                                                       672
```

<210> SEQ ID NO 16
<211> LENGTH: 224
<212> TYPE: PRT
<213> ORGANISM: Emiliana huxleyi
<220> FEATURE:
<221> NAME/KEY: MOD_RES
<222> LOCATION: (191)..(191)
<223> OTHER INFORMATION: Any amino acid

<400> SEQUENCE: 16

Met Gly Lys Gly Gly Asn Ala Asn Pro Arg Glu Leu Lys Gly Lys
1               5                   10                  15

Ala Glu Gln Leu Thr Val Tyr Leu Tyr Gly Lys Ala Val Asp Val Ser
            20                  25                  30

Lys Phe Ala Lys Leu His Pro Gly Gly Ala Lys Ala Leu Arg Ile Phe
        35                  40                  45

Asn Asn Arg Asp Ala Thr Glu Gln Phe Glu Met Tyr His Ser Pro Ala
    50                  55                  60

Ala His Lys Met Met Arg Ala Met Ser Lys Ser Ala Pro Glu Ala Pro
65                  70                  75                  80

Arg Glu Ser Glu Val Ala Thr Ser Val Val Gly Thr Asp Phe Ala Lys
                85                  90                  95

Leu Thr Gln Thr Leu His Asp Val Gly Cys Phe Asp Pro His Tyr Pro
            100                 105                 110

Asp Glu Ala Phe Lys Leu Gly Leu Thr Leu Leu Pro Gly Phe Leu Gly
        115                 120                 125

Phe Tyr Leu Leu Arg Ser Gly Met Pro Ala Leu Gly Ser Phe Leu Ile
    130                 135                 140

Ala Phe Ser Tyr Tyr Met Ser Gly Trp Thr Ser His Asp Tyr Leu His
145                 150                 155                 160

His Gly Cys Leu Lys Gly Gly Gln Lys Gln Leu Val His Trp Asn Asn
                165                 170                 175

Ala Val Gly Tyr Ala Ile Gly Ala Trp Gln Gly Tyr Ala Val Xaa Trp
            180                 185                 190

Trp Arg Ala Arg His Asn Thr His His Leu Val Thr Asn Glu Glu Gly
        195                 200                 205

Asn Asp Pro Asp Ile Met Thr Ala Pro Val Leu Ile Phe Val Arg Asn
    210                 215                 220

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
gtaccagtgg ctgctgctga cgatg                                         25
```

<210> SEQ ID NO 18
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggcgcttc gagtcgatgc agtacct                                        27

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttcgtgcgc aacagcccgg tgatc                                          25

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccagtcacg acgttgtaaa acgacggcca g                                   31

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gctgtcaacg atacgctacg taacggcatg acagtgt                             37

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgtcaacg atacgctacg taacg                                          25

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgctacgtaa cggcatgaca gtg                                            23

<210> SEQ ID NO 24
<211> LENGTH: 589
<212> TYPE: DNA
<213> ORGANISM: Emiliana huxleyi
```

-continued

<400> SEQUENCE: 24

```
gtaccagtgg ctgctgctga cgatgctggt gcgcggcttc ctcacgggca tcgtcgtctt     60
ctcgacgcat tatggcgagg aggtcatccc gggcgaccac ggcatgacac tcgtcgagca    120
gacggcgctc acctctcgca acatcaccgg cgggtacctc gtcaacctgc tcacgggcta    180
catctcgctg cagacggagc accacctctg gccgatgatg cccaccgcgc gcctcgaggc    240
ggcgcagccc tacgcgcgcg ccttcttcaa gaagcacggc ttcgtctacc gcgagtcgaa    300
cctcgtcgag tgcgtcaagt acaacatcgc cgccctcgac atcaccacgc gcaacggcga    360
gtgggcagag atgccgcact agccggcggg ctccgcctct ccaggccgga cgtgaccgcg    420
ccgcgggcga cagcgaccgc gcgggccgca cgggccacct gttgagggga gcggcgtcgc    480
aacaggcaga gagataataa tagagaggca tgtgtgctgg gacgctattg gctatttcgg    540
tatatggaca ggcaggtagc gcgcaaaaaa aaaaaaaaaa aaaaaaaa                 589
```

<210> SEQ ID NO 25
<211> LENGTH: 126
<212> TYPE: PRT
<213> ORGANISM: Emiliana huxleyi

<400> SEQUENCE: 25

```
Tyr Gln Trp Leu Leu Leu Thr Met Leu Val Arg Gly Phe Leu Thr Gly
1               5                   10                  15

Ile Val Val Phe Ser Thr His Tyr Gly Glu Glu Val Ile Pro Gly Asp
            20                  25                  30

His Gly Met Thr Leu Val Glu Gln Thr Ala Leu Thr Ser Arg Asn Ile
        35                  40                  45

Thr Gly Gly Tyr Leu Val Asn Leu Leu Thr Gly Tyr Ile Ser Leu Gln
    50                  55                  60

Thr Glu His His Leu Trp Pro Met Met Pro Thr Ala Arg Leu Glu Ala
65                  70                  75                  80

Ala Gln Pro Tyr Ala Arg Ala Phe Phe Lys Lys His Gly Phe Val Tyr
                85                  90                  95

Arg Glu Ser Asn Leu Val Glu Cys Val Lys Tyr Asn Ile Ala Ala Leu
            100                 105                 110

Asp Ile Thr Thr Arg Asn Gly Glu Trp Ala Glu Met Pro His
        115                 120                 125
```

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
aaagaattca tgggcaaggg cggcaacgcg aacc                                 34
```

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
aaaaagcttc tagtgcggca tctctgccca ctcg                                 34
```

<210> SEQ ID NO 28
<211> LENGTH: 1254
<212> TYPE: DNA
<213> ORGANISM: Emiliana huxleyi

<400> SEQUENCE: 28

```
atgggcaagg gcggcaacgc gaacccgcgg gagctcaaag gcggcaaggc cgagcagctg        60
acagtctacc tgcatggcaa ggctgtcgac gtctcgaagt tcgcgaagct gcacccggga       120
ggcgccaagg cgctgcgcat cttcaacaac cgtgacgcca ccgagcagtt cgagatgtac       180
cactcgcccg ccgcccacaa gatgatgcgt gcgatgtcga agagcgcgcc ggaggccccg       240
agggagagcg aggtcgcgac gtcggtcgtt gggacggact cgccaagct gacgcagacg        300
ctgcacgacg tcggatgctt cgaccctcac tacccagacg aggccttcaa gctcggcctc       360
acgctgctgc ccggattcct cggcttctac ctgctgcgga gcggcatgcc ggcgctcgga       420
tccttcctga tcgctttctc gtactacatg tctgggtgga cctcccacga ttacttgcac       480
cacggctgcc tcaagggcgg ccaaaagcag ctggtgcact ggaacaacgc cgtcggctac       540
gcaatcggcc cttggcaggg ctacgcggtc ggctggtggc gagcgcgcca caacacgcac       600
cacctcgtca cgaacgaaga aggcaacgac cccgacatca tgaccgcgcc tgtgctcatc       660
ttcgtgcgca caacccggt gatcgccgct gccctcaacg cggcgcagcg gtggcagcag        720
tactactacg tgcccgcgat gagcctcatg gacatgtact ggcgcttcga gtcgatgcag       780
tacctggccg cgcggcccct taacaaggtc tgggcctcgt gggcgctcct cgcgctgcac       840
tactcctttg tcggctacat gttccacgga cagtaccagt ggctgctgct gacgatgctg       900
gtgcgcggct tcctcacggg catcgtcgtc ttctcgacgc attatggcga ggaggtcatc       960
ccgggcgacc acggcatgac actcgtcgag cagacggcgc acacctctcg caacatcacc      1020
ggcgggtacc tcgtcaacct gctcacgggc tacatctcgc tgcagacgga gcaccacctc      1080
tggccgatga tgcccaccgc gcgcctcgag gcggcgcagc cctacgcgcg cgccttcttc      1140
aagaagcacg gcttcgtcta ccgcgagtcg aacctcgtcg agtgcgtcaa gtacaacatc      1200
gccgccctcg acatcaccac gcgcaacggc gagtgggcag agatgccgca ctag            1254
```

<210> SEQ ID NO 29
<211> LENGTH: 417
<212> TYPE: PRT
<213> ORGANISM: Emiliana huxleyi

<400> SEQUENCE: 29

```
Met Gly Lys Gly Gly Asn Ala Asn Pro Arg Glu Leu Lys Gly Gly Lys
1               5                   10                  15

Ala Glu Gln Leu Thr Val Tyr Leu His Gly Lys Ala Val Asp Val Ser
            20                  25                  30

Lys Phe Ala Lys Leu His Pro Gly Gly Ala Lys Ala Leu Arg Ile Phe
        35                  40                  45

Asn Asn Arg Asp Ala Thr Glu Gln Phe Glu Met Tyr His Ser Pro Ala
    50                  55                  60

Ala His Lys Met Met Arg Ala Met Ser Lys Ser Ala Pro Glu Ala Pro
65                  70                  75                  80

Arg Glu Ser Glu Val Ala Thr Ser Val Val Gly Thr Asp Phe Ala Lys
                85                  90                  95

Leu Thr Gln Thr Leu His Asp Val Gly Cys Phe Asp Pro His Tyr Pro
            100                 105                 110
```

Asp Glu Ala Phe Lys Leu Gly Leu Thr Leu Leu Pro Gly Phe Leu Gly
            115                 120                 125

Phe Tyr Leu Leu Arg Ser Gly Met Pro Ala Leu Gly Ser Phe Leu Ile
130                 135                 140

Ala Phe Ser Tyr Tyr Met Ser Gly Trp Thr Ser His Asp Tyr Leu His
145                 150                 155                 160

His Gly Cys Leu Lys Gly Gly Gln Lys Gln Leu Val His Trp Asn Asn
                165                 170                 175

Ala Val Gly Tyr Ala Ile Gly Ala Trp Gln Gly Tyr Ala Val Gly Trp
            180                 185                 190

Trp Arg Ala Arg His Asn Thr His His Leu Val Thr Asn Glu Glu Gly
            195                 200                 205

Asn Asp Pro Asp Ile Met Thr Ala Pro Val Leu Ile Phe Val Arg Asn
210                 215                 220

Asn Pro Val Ile Ala Ala Leu Asn Ala Ala Gln Arg Trp Gln Gln
225                 230                 235                 240

Tyr Tyr Tyr Val Pro Ala Met Ser Leu Met Asp Met Tyr Trp Arg Phe
                245                 250                 255

Glu Ser Met Gln Tyr Leu Ala Ala Arg Pro Phe Asn Lys Val Trp Ala
            260                 265                 270

Ser Trp Ala Leu Leu Ala Leu His Tyr Ser Phe Val Gly Tyr Met Phe
275                 280                 285

His Gly Gln Tyr Gln Trp Leu Leu Leu Thr Met Leu Val Arg Gly Phe
            290                 295                 300

Leu Thr Gly Ile Val Val Phe Ser Thr His Tyr Gly Glu Glu Val Ile
305                 310                 315                 320

Pro Gly Asp His Gly Met Thr Leu Val Glu Gln Thr Ala His Thr Ser
                325                 330                 335

Arg Asn Ile Thr Gly Gly Tyr Leu Val Asn Leu Leu Thr Gly Tyr Ile
            340                 345                 350

Ser Leu Gln Thr Glu His His Leu Trp Pro Met Met Pro Thr Ala Arg
355                 360                 365

Leu Glu Ala Ala Gln Pro Tyr Ala Arg Ala Phe Phe Lys Lys His Gly
            370                 375                 380

Phe Val Tyr Arg Glu Ser Asn Leu Val Glu Cys Val Lys Tyr Asn Ile
385                 390                 395                 400

Ala Ala Leu Asp Ile Thr Thr Arg Asn Gly Glu Trp Ala Glu Met Pro
                405                 410                 415

His

<210> SEQ ID NO 30
<211> LENGTH: 1257
<212> TYPE: DNA
<213> ORGANISM: Emiliana huxleyi

<400> SEQUENCE: 30
aaaatgggta aggtggtaa tgctaatcca agagaattga aaggtggtaa agctgaacaa    60
ttgactgttt atttgcatgg taaagctgtt gatgtttcta aatttgctaa attgcatcca   120
ggtggtgcta aagcattgag aattttaat aatagagatg ctactgaaca atttgaaatg   180
tatcattctc cagctgctca taaaatgatg agagctatgt ctaaatctgc tccagaaagct  240 ccaagagaat ctgaagttgc tacttctgtt gttggtactg attttgctaa attgactcaa   300
actttgcatg atgttggttg ttttgatcca cattatccag atgaagcatt taaattgggt   360
ttgactttgt tgccaggttt tttgggtttt tatttgttga gatctggtat gccagctttg   420

```
ggttcttttt tgattgcttt ttcttattat atgtctggtt ggacttctca tgattatttg      480
catcatggtt gtttgaaagg tggtcaaaaa caattggttc attggaataa tgctgttggt      540
tatgctattg gtgcttggca aggttatgct gttggttggt ggagagctag acataatact      600
catcatttgg ttactaatga agaaggtaat gatccagata ttatgactgc tccagttttg      660
atttttgtta gaaataatcc agttattgct gctgctttga atgctgctca aagatggcaa      720
caatattatt atgttccagc tatgtctttg atggatatgt attggagatt tgaatctatg      780
caatatttgg ctgctagacc atttaataaa gtttgggctt cttgggcttt gttggctttg      840
cattattctt ttgttggtta tatgtttcat ggtcaatatc aatggttgtt gttgactatg      900
ttggttagag ttttttgac tggtattgtt gttttttcta ctcattatgg tgaagaagtt      960
attccaggtg atcatggtat gactttggtt gaacaaactg ctcatacttc tagaaatatt     1020
actggtggtt atttggttaa tttgttgact ggttatattt ctttgcaaac tgaacatcat     1080
ttgtggccaa tgatgccaac tgctagattg gaagctgctc aaccatatgc tagagctttt     1140
tttaaaaaac atggttttgt ttatagagaa tctaatttgg ttgaatgtgt taaatataat     1200
attgctgctt tggatattac tactagaaat ggtgaatggg ctgaaatgcc acattaa       1257

<210> SEQ ID NO 31
<211> LENGTH: 792
<212> TYPE: DNA
<213> ORGANISM: Isochrysis galbana

<400> SEQUENCE: 31
atggccctcg caaacgacgc gggagagcgc atctgggcgg ctgtgaccga cccggaaatc       60
ctcattggca ccttctcgta cttgctactc aaaccgctgc tccgcaattc cgggctggtg      120
gatgagaaga agggcgcata caggacgtcc atgatctggt acaacgttct gctggcgctc      180
ttctctgcgc tgagcttcta cgtgacggcg accgccctcg gctgggacta tggtacgggc      240
gcgtggctgc gcaggcaaac cggcgacaca ccgcagccgc tcttccagtg cccgtccccg      300
gtttgggact cgaagctctt cacatggacc gccaaggcat tctattactc caagtacgtg      360
gagtacctcg acacggcctg gctggtgctc aagggcaaga gggtctcctt tctccaggcc      420
ttccaccact tggcgcgcc gtgggatgtg tacctcggca ttcggctgca caacgagggc      480
gtatggatct tcatgttttt caactcgttc attcacacca tcatgtacac ctactacggc      540
ctcaccgccg ccgggtataa gttcaaggcc aagccgctca tcaccgcgat gcagatctgc      600
cagttcgtgg gcggcttcct gttggtctgg gactacatca acgtcccctg cttcaactcg      660
gacaaaggga agttgttcag ctgggctttc aactatgcat acgtcggctc ggtcttcttg      720
ctcttctgcc acttttccta ccaggacaac ttggcaacga gaaatcggc caaggcgggc      780 aagcagctct ag                                                           792

<210> SEQ ID NO 32
<211> LENGTH: 5
<212> TYPE: PRT
<213> ORGANISM: Emiliana huxleyi

<400> SEQUENCE: 32

His Asp Tyr Leu His
1               5

<210> SEQ ID NO 33
<211> LENGTH: 5
<212> TYPE: PRT
```

<213> ORGANISM: Emiliana huxleyi

<400> SEQUENCE: 33

His Asn Thr His His
1               5

<210> SEQ ID NO 34
<211> LENGTH: 5
<212> TYPE: PRT
<213> ORGANISM: Emiliana huxleyi

<400> SEQUENCE: 34

Gln Thr Glu His His
1               5

<210> SEQ ID NO 35
<211> LENGTH: 789
<212> TYPE: DNA
<213> ORGANISM: Euglenoid deses

<400> SEQUENCE: 35

```
atggacgtcg cgactacgct ggctggcatc gcggcggacg tgctgccccg cgtggactac    60
gcgcggcttg ggcgcgacgc cgccgcctgc gaggttctat acctttcgct gttcttcatc   120
gccatgaagt tcatccttcg cccccctcgg gacaaggggc aggcccgcct caagtcgctc   180
ttcaccctct acaacctcgt gatgtccatc tactccctcg gatctttcgt tgtaatgggc   240
tacgccttgg cggatatcgg agtgctcggt ggtgattgcg ggaaagcatt ctcaaatccc   300
atgttccgcc tcaccgctca gttgttctac atcagcaagt acgttgagta catcgattcc   360
ttctacgtgc ttctcaccaa caagcccctg acctacctgc agttcttcca ccacctcgga   420
gcccccgtcg acctctggct cttcctgcag tacgaaaacg aggcgctgtg gatcttcgtc   480
ttcctcaacg gcttcatcca cttcatcatg tacgggtact actgggcccg gctggtgaag   540
ctcccgttcc ccgtgccgaa gtcgttcatc acctccatgc agatcatcca gttcaacctg   600
ggcttctacc tcgtgtggcg gtaccacaca atcccgtgct accgacagga cccaatgcga   660
atgttcgctt ggctcttcaa ctacttctac gtgggagtgg tcttactgct gttttttgaat   720 ttctacgtgc acacgtacgt gatcaagaaa gcgcggcggc tggcgaagga tgagaagaaa   780
gtggactag                                                            789
```

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tatagaattc aaatggacgt cgcgactacg ctg                                  33

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tattctcgag ttctagtcca ctttcttctc atccttc                              37

```
<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(6)
<223> OTHER INFORMATION: Ala or Gln
<220> FEATURE:
<221> NAME/KEY: MOD_RES
<222> LOCATION: (8)..(8)
<223> OTHER INFORMATION: Glu or Met
<220> FEATURE:
<221> NAME/KEY: MOD_RES
<222> LOCATION: (9)..(9)
<223> OTHER INFORMATION: Ser or Val
<220> FEATURE:
<221> NAME/KEY: MOD_RES
<222> LOCATION: (10)..(10)
<223> OTHER INFORMATION: Tyr or Met

<400> SEQUENCE: 38

Arg Asp Ala Thr Xaa Xaa Phe Xaa Xaa Xaa His
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Ser
<220> FEATURE:
<221> NAME/KEY: MOD_RES
<222> LOCATION: (7)..(7)
<223> OTHER INFORMATION: Tyr or Ile
<220> FEATURE:
<221> NAME/KEY: MOD_RES
<222> LOCATION: (8)..(8)
<223> OTHER INFORMATION: Leu or Ser

<400> SEQUENCE: 39

Gly Trp Leu Xaa His Asp Xaa Xaa His His
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Ala or Leu
<220> FEATURE:
<221> NAME/KEY: MOD_RES
<222> LOCATION: (7)..(7)
<223> OTHER INFORMATION: Thr or Ala
```

<400> SEQUENCE: 40

Trp Xaa Xaa Arg His Asn Xaa His His
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Ala or Gly
<220> FEATURE:
<221> NAME/KEY: MOD_RES
<222> LOCATION: (5)..(5)
<223> OTHER INFORMATION: Ile or Val

<400> SEQUENCE: 41

Phe Xaa Thr Xaa Xaa Val Val Phe Ala Thr His Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Thr
<220> FEATURE:
<221> NAME/KEY: MOD_RES
<222> LOCATION: (9)..(9)
<223> OTHER INFORMATION: Thr or Met

<400> SEQUENCE: 42

Gln Xaa Glu His His Leu Phe Pro Xaa Met Pro
1               5                   10

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gctgtcaacg atacgctacg taacggcatg acagtgtttt tttttttttt tttttttttt      60

<210> SEQ ID NO 44
<211> LENGTH: 10
<212> TYPE: PRT
<213> ORGANISM: Emiliana huxleyi

<400> SEQUENCE: 44

Pro Ala Gly Ser Ala Ser Pro Gly Arg Thr
1               5                   10

<210> SEQ ID NO 45

```
<211> LENGTH: 47
<212> TYPE: PRT
<213> ORGANISM: Emiliana huxleyi

<400> SEQUENCE: 45

Pro Arg Arg Gly Arg Gln Arg Pro Arg Gly Pro His Gly Pro Pro Val
1               5                   10                  15

Glu Gly Ser Gly Val Ala Thr Gly Arg Glu Ile Ile Ile Glu Arg His
            20                  25                  30

Val Cys Trp Asp Ala Ile Gly Tyr Phe Gly Ile Trp Thr Gly Arg
        35                  40                  45

<210> SEQ ID NO 46
<211> LENGTH: 17
<212> TYPE: PRT
<213> ORGANISM: Emiliana huxleyi

<400> SEQUENCE: 46

Arg Lys Lys Lys Lys Lys Lys Lys His Met Pro Leu Arg Ser Glu
1               5                   10                  15

Gly
```

What is claimed is:

1. An isolated nucleic acid comprising a nucleotide sequence encoding a polypeptide comprising the amino acid sequence of SEQ ID NO:29.

2. An isolated nucleic acid comprising a nucleotide sequence at least 90% identical to SEQ ID NO:30, wherein the nucleotide sequence encodes a polypeptide having Δ8-desaturase activity.

3. The isolated nucleic acid of claim 2, wherein the nucleotide sequence encodes a functionally active Δ8-desaturase enzyme which utilizes ω6-eicosadienoic acid or ω3-eicosatrienoic acid as a substrate.

4. An expression vector comprising: a nucleotide sequence operably linked to a regulatory sequence, wherein the nucleotide sequence is at least 90% identical to SEQ ID NO:30.

5. A host cell comprising the vector of claim 4.

6. The host cell of claim 5, wherein the host cell is an eukaryotic cell, wherein the eukaryotic cell is selected from the group consisting of: a mammalian cell, an insect cell, a plant cell and a fungal cell.

7. A plant cell, plant seed, plant or plant tissue comprising the vector of claim 4, wherein expression of the nucleotide sequence of the vector results in production of at least one polyunsaturated fatty acid by the plant cell, plant seed, plant or plant tissue.

8. The plant cell, plant seed, plant or plant tissue of claim 7, wherein the polyunsaturated fatty acid is selected from the group consisting of: arachidonic acid (ARA), eicosapentaenoic acid (EPA), docosahexaenoic acid (DHA), dihomo-gamma-linolenic acid (DGLA) or ω3-eicosatetraenoic acid (ω3-ETA) and combinations thereof.

9. A method of producing an Δ8-desaturase enzyme, the method comprising the steps of:
a) isolating a nucleotide sequence at least 90% identical to SEQ ID NO:30;
b) constructing an expression vector comprising the isolated nucleotide sequence from step a) operably linked to a regulatory sequence; and
c) introducing the expression vector into a host cell for a time and under conditions sufficient for production of the Δ8-desaturase enzyme.

10. A method for producing a polyunsaturated fatty acid comprising the steps of:
a) isolating a nucleotide sequence at least 90% identical to SEQ ID NO:30;
b) constructing an expression vector comprising the isolated nucleotide sequence from step a) operably linked to a regulatory sequence;
c) introducing the expression vector into a host cell for a time and under conditions sufficient for production of an Δ8-desaturase enzyme; and
d) exposing the expressed Δ8-desaturase enzyme to a substrate selected from the group consisting of: ω6-eicosadienoic acid, ω3-eicosatrienoic acid and combinations thereof in order to convert the substrate to a product polyunsaturated fatty acid.

11. The method of claim 10, wherein the product polyunsaturated fatty acid is dihomo-gamma-linolenic acid (DGLA), ω3-eicosatetraenoic acid (ω3-ETA) or any combinations thereof.

12. The method of claim 10, further comprising the step of: exposing the product polyunsaturated fatty acid to at least one additional desaturase or to an elongase in order to convert the product polyunsaturated fatty acid to another or additional polyunsaturated fatty acid.

13. A method for producing a polyunsaturated fatty acid in a host cell comprising the steps of:
a) isolating a nucleotide sequence at least 90% identical to SEQ ID NO:30;
b) constructing an expression vector comprising the isolated nucleotide sequence from step a) operably linked to a regulatory sequence;
c) introducing the expression vector from b) and at least one additional recombinant DNA construct comprising an isolated nucleotide sequence operably linked to at least one regulatory sequence encoding a delta-9 elongase into a host cell;
d) exposing the expressed Δ8-desaturase enzyme and delta-9 elongase to a substrate selected from the group consisting of: linoleic acid (LA), alpha-linolenic acid (ALA) and combinations thereof in order to convert the substrate to a product polyunsaturated fatty acid.

14. The method of claim 13, wherein the product polyunsaturated fatty acid is dihomo-gamma-linolenic acid (DGLA) or ω3-eicosatetraenoic acid (ω3-ETA) or any combinations thereof.

15. The method of claim 13, further comprising the step of: exposing the product polyunsaturated fatty acid to at least one additional desaturase or to an elongase in order to convert the product polyunsaturated fatty acid to another or additional polyunsaturated fatty acid.

16. The method of claim 15, wherein the product polyunsaturated fatty acid is arachidonic acid (ARA), eicosapentaenoic acid (EPA), docosapentaenoic acid (DPA), docosahexaenoic acid (DHA) or any combinations thereof.

17. An isolated nucleic acid comprising a nucleotide sequence comprising SEQ ID NO:28, wherein the nucleotide sequence encodes a polypeptide having Δ8-desaturase activity.

18. An expression vector comprising the nucleotide sequence of claim 17 operably linked to a regulatory sequence.

19. A plant cell, plant seed, plant or plant tissue comprising the vector of claim 18, wherein expression of the nucleotide sequence of the vector results in production of at least one polyunsaturated fatty acid by the plant cell, plant seed, plant or plant tissue.

20. A method for producing a polyunsaturated fatty acid comprising the steps of:
a) introducing the expression vector of claim 18 into a host cell for a time and under conditions sufficient for production of an Δ8-desaturase enzyme; and
b) exposing the expressed Δ8-desaturase enzyme to a substrate selected from the group consisting of: ω6-eicosadienoic acid, ω3-eicosatrienoic acid and combinations thereof in order to convert the substrate to a product polyunsaturated fatty acid.

21. A method for producing a polyunsaturated fatty acid in a host cell comprising the steps of:
a) introducing the expression vector of claim 18 and at least one additional recombinant DNA construct comprising an isolated nucleotide sequence operably linked to at least one regulatory sequence encoding a delta-9 elongase into a host cell; and
b) exposing the expressed Δ8-desaturase enzyme and delta-9 elongase to a substrate selected from the group consisting of: linoleic acid (LA), alpha-linolenic acid (ALA) and combinations thereof in order to convert the substrate to a product polyunsaturated fatty acid.

* * * * *